US009211327B2

(12) United States Patent
Nilles

(10) Patent No.: US 9,211,327 B2
(45) Date of Patent: Dec. 15, 2015

(54) USE OF YSCF, TRUNCATED YSCF AND YSCF HOMOLOGS AS ADJUVANTS

(75) Inventor: Matthew Nilles, Grand Forks, ND (US)

(73) Assignee: University of North Dakota, Grand Forks, ND (US)

( * ) Notice: Subject to any disclaimer, the term of this patent is extended or adjusted under 35 U.S.C. 154(b) by 0 days.

(21) Appl. No.: 14/126,405

(22) PCT Filed: Jun. 22, 2012

(86) PCT No.: PCT/US2012/043838
§ 371 (c)(1),
(2), (4) Date: Dec. 13, 2013

(87) PCT Pub. No.: WO2012/178078
PCT Pub. Date: Dec. 27, 2012

(65) Prior Publication Data
US 2014/0120128 A1    May 1, 2014

Related U.S. Application Data

(60) Provisional application No. 61/499,924, filed on Jun. 22, 2011.

(51) Int. Cl.
*A61K 39/00* (2006.01)
*A61K 39/39* (2006.01)
*G01N 33/50* (2006.01)
*A61K 39/02* (2006.01)

(52) U.S. Cl.
CPC ............ *A61K 39/39* (2013.01); *A61K 39/0291* (2013.01); *G01N 33/5055* (2013.01); *A61K 2039/55544* (2013.01)

(58) Field of Classification Search
None
See application file for complete search history.

(56) References Cited

U.S. PATENT DOCUMENTS

| | | | |
|---|---|---|---|
| 4,879,213 A | 11/1989 | Fox et al. | |
| 5,985,285 A | 11/1999 | Titball et al. | |
| 6,261,561 B1 | 7/2001 | Stewart, Jr. et al. | |
| 6,331,388 B1 | 12/2001 | Malkovsky et al. | |
| 7,344,718 B2 | 3/2008 | Nilles et al. | |
| 7,608,266 B2 | 10/2009 | Nilles et al. | |
| 2004/0151727 A1* | 8/2004 | Nilles et al. | 424/184.1 |
| 2008/0025999 A1* | 1/2008 | Nilles et al. | 424/190.1 |
| 2009/0327170 A1* | 12/2009 | Donati et al. | 706/12 |
| 2010/0209541 A1* | 8/2010 | Dugger, III | 424/682 |
| 2014/0120128 A1* | 5/2014 | Nilles | 424/190.1 |

FOREIGN PATENT DOCUMENTS

| | | | |
|---|---|---|---|
| WO | 95/18231 A1 | 7/1995 | |
| WO | 96/28551 A1 | 9/1996 | |
| WO | 98/24912 A2 | 6/1998 | |
| WO | 02/077249 A2 | 10/2002 | |
| WO | 2004082596 A2 | 1/2004 | |
| WO | 2012178078 A2 | 12/2012 | |

OTHER PUBLICATIONS

Matson et al, BMC Microbiology 2005, 5:38 doi:10.1186/1471-2180-5-38.*
Plano et al, Immunol Res (2013) 57:237-245.*
Valentina et al, Expert Rev. Vaccines, 2009, 8/12:1721-1738.*
Benner et at, Immune Response to Yersinia Outer Proteins and Other Yersinia pestis Antigens After Experimental Plague Infection in Mice, Infection and Immunity, 1999, pp. 1922-1928, vol. 67, No. 4.
Cole et al., a plague o'both your hosts, Nature, Oct. 2001, pp. 467-470, vol. 413.
Edqvist et al., YscP and YscU Regulate Substrate Specificity of the Yersinia Type III Secretion System, Journal of Bacteriology, Apr. 2003, pp. 2259-2266, vol. 185, No. 7.
Hill et al., Immunological characterization of sub-units of the Yersinia type III secretion apparatus. Abstract at the 8th International Symposium on Yersinia, Sep. 4-8, 2002, Turku, Finland.
Hoiczyk et al., Polymerization of a single protein of the pathogen Yersinia enterocolitica into needles punctures eukaryotic cells, PNAS, Apr. 10, 2001, pp. 26669-26674, vol. 98, No. 8.
Hu et al., Structural Organization of Virulence-Associated Plasmids of Yersinia pestis, Journal of Bacteriology, Oct. 1998, pp. 5192-5202, vol. 180, No. 19.
Michiels et al., Analysis of virC, an Operon Involved in the Secretion of Yop Proteins by Yersinia; enterocolitica, Journal of Bacteriology, Aug. 1991, pp. 4994-5009, vol. 173, No. 16.
Oyston et al., Yersinia: an update, Dec. 2002, the 8th International Symposium on Yersinia held in Turku, Finland, Sep. 4-8, 2009. Published online: Oct. 24, 2002, published in Trends in Microbiology, vol. 10, No. 12, Dec. 2002, pp. 550-551.
Parkhill et l., Genome sequence of Yersinia pestis, the causative agent of plague, Nature, Oct. 4, 2001, pp. 523-527, vol. 413.
PCT International Search Report, PCT/US04/02852, dated Apr. 7, 2005.
Perry et al., "DNA Sequencing and Analysis of the Low-Ca2+—Response Plasmid pCD1 of Yersinia pestis KIM5," Infection and Immunity, vol. 66, No. 10, pp. 4611-4623, Oct. 1998.
Plotkin et al., Vaccines, W.B. Saunders Co., 1988, p. 571.
Supplementary Partial European Search Report, EP 04 74 9309, dated Mar. 29, 2007.

(Continued)

*Primary Examiner* — Nita M Minnifield
(74) *Attorney, Agent, or Firm* — TraskBritt, P.C.

(57) ABSTRACT

An antigenic composition comprising an antigen and an effective adjuvant, the adjuvant comprising isolated or recombinant YscF, a YscF fragment, truncated YscF (trYscF), or homologs thereof. A method of inducing an enhanced immune response comprising administering an antigen and an effective adjuvant comprising isolated or recombinant YscF, a YscF fragment, trYscF, or homologs thereof. An antigenic composition produced by a process comprising providing a host cell with an expression vector containing a nucleotide sequence encoding YscF, a YscF fragment, trYscF, or YscF homolog capable of acting as an adjuvant; expressing the nucleotide sequence in the host cell to produce the protein; and mixing the collected protein with a suitable excipient.

25 Claims, 36 Drawing Sheets

(56) References Cited

OTHER PUBLICATIONS

Titball et al., Vaccination agains bubonic and pneumonic plague, Vaccine, 2001, pp. 4175-4184, vol. 19.

Williamson, E.D., Plague vaccine research and development, Journal of Applied Microbiology, 2001, pp. 606-608, vol. 91.

Wilson, et al., Role of EscF, a putative needle complex protein, in the type III protein translocation system of enteropathogenic *Escherichia coli*, Cellular Microbiology, 2001, pp. 753-762, vol. 3, No. 11.

Ali, R., et al., Humoral and mucosal immune response to immunodominant peptides of YscF antigen of Yersinia pestis: An Immunoprophylactic approach to plague infection, 14th International Congress of Immunology Abstract Book, 2010, pp. 049-23 (abstract).

Matson, J., et al., Immunization of mice with YscF provides protection from Yersinia pestis infections, BMC Microbiology, 2005, vol. 5, Article No. 38, ISSN 1471-2180.

International Search Report and Written Opinion for International Application No. PCT/US2012/043838, mailed Dec. 27, 2012, 14 pages.

International Preliminary Report on Patentability for International Application No. PCT/US2012/043838, mailed Jan. 9, 2014, 9 pages.

Swietnicki, W., et al., Yersinia pestis Yop secretion protein F: Purification, characterization, and protective efficacy against bubonic plague, Protein Expression and Purification, vol. 42, No. 1, 2005, pp. 166-172.

Osei-Owusu et al., The N Terminus of Type III Secretion Needle Protein YscF from Yersinia pestis Functions to Modulate Innate Immune Responses, with Supplemental Drawings, Infection and Immunity, Apr. 2015, pp. 1507-1522, vol. 83, No. 4.

Jessen et al., Type III Secretion Needle Proteins Induce Cell Signaling and Cytokine Secretion via Toll-Like Receptors, with Supplemental Drawings, Infection and Immunity, Jun. 2014, pp. 2300-2309, vol. 82, No. 6.

\* cited by examiner

```
5' AAGGGCGAGCTCAACGATCCGGCTGCTAACAAAGCCCGAAAGGAAGCTGAGTTGGCTGCT
   ++++|++++|++++|++++|++++|++++|++++|++++|++++|++++|++++|++++| 60
        T.2>                    T7 transcription termination region
3' K  G  R  A  Q  R  S  G  C  .  Q  S  P  K  G  S  .  V  G  C 5' GCCACCGCTGAGCAATAACTAGCATAACCCCTTGGGGCCTCTAAACGGGTCTTGAGGAGT
   ++++|++++|++++|++++|++++|++++|++++|++++|++++|++++|++++|++++| 120
           T7 reverse priming site
                    T7 transcription termination region
3' C  H  R  .  A  I  T  S  I  T  P  W  G  L  .  T  G  L  E  E 5' TTTTTGCTGAAAGGAGGAACTATATCCGGATATCCCGCAAGAGGCCCGGCAGTACCGGCA
   ++++|++++|++++|++++|++++|++++|++++|++++|++++|++++|++++|++++| 180
        T7 transcription termination region
3' F  F  A  E  R  R  N  Y  I  R  I  S  R  K  R  P  G  S  T  G 5' TAACCAAGCCTATGCCTACAGCATCCAGGGTGACGGTGCCGAGGATGACGATGAGCGCAT
   ++++|++++|++++|++++|++++|++++|++++|++++|++++|++++|++++|++++| 240
3' I  T  K  P  M  P  T  A  S  R  V  T  V  P  R  M  T  M  S  A 5' TGTTAGATTTCATACACGGTGCCTGACTGCGTTAGCAATTTAACTGTGATAAACTACCGC
   ++++|++++|++++|++++|++++|++++|++++|++++|++++|++++|++++|++++| 300
3' L  L  D  F  I  H  G  A  .  L  R  .  Q  F  N  C  D  K  L  P 5' ATTAAAGCTTATCGATGATAAGCTGTCAAACATGAGAATTAATTCTTGAAGACGAAAGGG
   ++++|++++|++++|++++|++++|++++|++++|++++|++++|++++|++++|++++| 360
3' H  .  S  L  S  M  I  S  C  Q  T  .  E  L  I  L  E  D  E  R 5' CCTCGTGATACGCCTATTTTTATAGGTTAATGTCATGATAATAATGGTTTCTTAGACGTC
   ++++|++++|++++|++++|++++|++++|++++|++++|++++|++++|++++|++++| 420
3' A  S  .  Y  A  Y  F  Y  R  L  M  S  .  .  W  F  L  R  R 5' AGGTGGCACTTTTCGGGGAAATGTGCGCGGAACCCCTATTTGTTTATTTTCTAAATACA
   ++++|++++|++++|++++|++++|++++|++++|++++|++++|++++|++++|++++| 480
3' Q  V  A  L  F  G  E  M  C  A  E  P  L  F  V  Y  F  S  K  Y 5' TTCAAATATGTATCCGCTCATGAGACAATAACCCTGATAAATGCTTCAATAATATTGAAA
   ++++|++++|++++|++++|++++|++++|++++|++++|++++|++++|++++|++++| 540
3' I  Q  I  C  I  R  S  .  D  N  N  P  D  K  C  F  N  N  I  E
```

FIG. 2A

```
5' AAGGAAGAGTATGATTGAACAAGATGGATTGCACGCAGGTTCTCCGGCCGCTTGGGTGGA
                                                                    600
                        Kanamycin resistance gene
3  K  G  R  V  .  L  N  K  M  D  C  T  Q  V  L  R  P  L  G  W 5' GAGGCTATTCGGCTATGACTGGGCACAACTGACAATCGGCTGCTCTGATGCCGCCGTGTT
                                                                    660
                        Kanamycin resistance gene
3  R  G  Y  S  A  M  T  G  H  N  .  Q  S  A  A  L  M  P  P  C 5' CCGGCTGTCAGCGCAGGGGCGCCCGGTTCTTTTTGTCAAGACCGACCTGTCCGGTGCCCT
                                                                    720
                        Kanamycin resistance gene
3  S  G  C  Q  R  R  G  A  R  F  F  L  S  R  P  T  C  P  V  P 5' GAATGAACTGCAGGACGAGGCAGCGCGGCTATCGTGGCTGGCCACGACGGGCGTTCCTTG
                                                                    780
                        Kanamycin resistance gene
3  .  M  N  C  R  T  R  Q  R  G  Y  R  G  W  P  R  R  A  F  L 5' CGCAGCTGTGCTCGACGTTGTCACTGAAGCGGGAAGGGACTGGCTGCTATTGGGCGAAGT
                                                                    840
                        Kanamycin resistance gene
3  A  Q  L  C  S  T  L  S  L  K  R  E  G  T  G  C  Y  W  A  K 5' GCCGGGGCAGGATCTCCTGTCATCTCACCTTGCTCCTGCCGAGAAAGTATCCATCATGGC
                                                                    900
                        Kanamycin resistance gene
3  C  R  G  R  I  S  C  H  L  T  L  L  L  P  R  K  Y  P  S  W 5' TGATGCAATGCGGCGGCTGCATACGCTTGATCCGGCTACCTGCCCATTCGACCACCAAGC
                                                                    960
                        Kanamycin resistance gene
3  L  M  Q  C  G  G  C  I  R  L  I  R  L  P  A  H  S  T  T  K 5' GAAACATCGCATCGAGCGGGCACGTACTCGGATGGAAGCCGGTCTTGTCGATCAGGATGA
                                                                    1020
                        Kanamycin resistance gene
3  R  N  I  A  S  S  G  H  V  L  G  W  K  P  V  L  S  I  R  M
```

FIG. 2B

```
5' TCTGGACGAAGAGCATCAGGGGCTCGCGCCAGCCGAACTGTTCGCCAGGCTCAAGGCGCG
   ++++|++++|++++|++++|++++|++++|++++|++++|++++|++++|++++|++++  1080
                        Kanamycin resistance gene
3   I  W  T  K  S  I  R  G  S  R  Q  P  N  C  S  P  G  S  R  R 5' CATGCCCGACGGCGAGGATCTCGTCGTGACACATGGCGATGCCTGCTTGCCGAATATCAT
   ++++|++++|++++|++++|++++|++++|++++|++++|++++|++++|++++|++++  1140
                        Kanamycin resistance gene
3   A  C  P  T  A  R  I  S  S  .  H  M  A  M  P  A  C  R  I  S 5' GGTGGAAAATGGCCGCTTTTCTGGATTCATCGACTGTGGCCGGCTGGGTGTGGCGGACCG
   ++++|++++|++++|++++|++++|++++|++++|++++|++++|++++|++++|++++  1200
                        Kanamycin resistance gene
3   W  W  K  M  A  A  F  L  D  S  S  T  V  A  G  W  V  W  R  T 5' CTATCAGGACATAGCGTTGGCTACCCGTGATATTGCTGAAGAGCTTGGCGGCGAATGGGC
   ++++|++++|++++|++++|++++|++++|++++|++++|++++|++++|++++|++++  1260
                        Kanamycin resistance gene
3   A  I  R  T  .  R  W  L  P  V  I  L  L  K  S  L  A  A  N  G 5' TGACCGCTTCCTCGTGCTTTACGGTATCGCCGCTCCCGATTCGCAGCGCATCGCCTTCTA
   ++++|++++|++++|++++|++++|++++|++++|++++|++++|++++|++++|++++  1320
                        Kanamycin resistance gene
3   L  T  A  S  S  C  F  T  V  S  P  L  P  I  R  S  A  S  P  S 5' TCGCCTTCTTGACGAGTTCTTCTGAGCGGGACTCTGGGGTTCGAAATGACCGACCAAGCG
   ++++|++++|++++|++++|++++|++++|++++|++++|++++|++++|++++|++++  1380
       Kanamycin resistance gene
3   I  A  F  L  T  S  S  S  E  R  D  S  G  V  R  N  D  R  P  S 5' ACGCCTAACTGTCAGACCAAGTTTACTCATATATACTTTAGATTGATTTAAAACTTCATT
   ++++|++++|++++|++++|++++|++++|++++|++++|++++|++++|++++|++++  1440
3   D  A  .  L  S  D  Q  V  Y  S  Y  I  L  .  I  D  L  K  L  H 5' TTTAATTTAAAAGGATCTAGGTGAAGATCCTTTTTGATAATCTCATGACCAAAATCCCTT
   ++++|++++|++++|++++|++++|++++|++++|++++|++++|++++|++++|++++  1500
3   F  .  F  K  R  I  .  V  K  I  L  F  D  N  L  M  T  K  I  P 5' AACGTGAGTTTTCGTTCCACTGAGCGTCAGACCCCGTAGAAAAGATCAAAGGATCTTCTT
   ++++|++++|++++|++++|++++|++++|++++|++++|++++|++++|++++|++++  1560
3   .  R  E  F  S  F  H  .  A  S  D  P  V  E  K  I  K  G  S  S
```

FIG. 2C

```
5' GAGATCCTTTTTTTCTGCGCGTAATCTGCTGCTTGCAAACAAAAAAACCACCGCTACCAG
                                                                1620
                            pBR322 origin
3'  . D P F F L R V I C C L Q T K K P P L P 5' CGGTGGTTTGTTTGCCGGATCAAGAGCTACCAACTCTTTTTCCGAAGGTAACTGGCTTCA
                                                                1680
                            pBR322 origin
3'   A V V C L P D Q E L P T L F P K V T G F 5' GCAGAGCGCAGATACCAAATACTGTCCTTCTAGTGTAGCCGTAGTTAGGCCACCACTTCA
                                                                1740
                            pBR322 origin
3'   S R A Q I P N T V L L V . P . L G H H F 5' AGAACTCTGTAGCACCGCCTACATACCTCGCTCTGCTAATCCTGTTACCAGTGGCTGCTG
                                                                1800
                            pBR322 origin
3'   K N S V A P P T Y L A L L I L L P V A A 5' CCAGTGGCGATAAGTCGTGTCTTACCGGGTTGGACTCAAGACGATAGTTACCGGATAAGG
                                                                1860
                            pBR322 origin
3'   A S G D K S C L T G L D S R R . L P D K 5' CGCAGCGGTCGGGCTGAACGGGGGGTTCGTGCACACAGCCCAGCTTGGAGCGAACGACCT
                                                                1920
                            pBR322 origin
3'   A Q R S G . T G G S C T Q P S L E R T T 5' ACACCGAACTGAGATACCTACAGCGTGAGCTATGAGAAAGCGCCACGCTTCCCGAAGGGA
                                                                1980
                            pBR322 origin
3'   Y T E L R Y L Q R E L . E S A T L P E G 5' GAAAGGCGGACAGGTATCCGGTAAGCGGCAGGGTCGGAACAGGAGAGCGCACGAGGGAGC
                                                                2040
                            pBR322 origin
3'   R K A D R Y P V S G R V G T G E R T R E
```

FIG. 2D

```
5' TTCCAGGGGGAAACGCCTGGTATCTTTATAGTCCTGTCGGGTTTCGCCACCTCTGACTTG
   +++++++++++++++++++++++++++++++++++++++++++++++++++++++++++ 2100
                          pBR322 origin
3  L P G G N A W Y L Y S P V G F R H L . L 5' AGCGTCGATTTTTGTGATGCTCGTCAGGGGGGCGGAGCCTATGGAAAAACGCCAGCAACG
   +++++++++++++++++++++++++++++++++++++++++++++++++++++++++++ 2160
                          pBR322 origin
3  E R R F L . C S S G G R S L W K N A S N 5' CGGCCTTTTTACGGTTCCTGGCCTTTTGCTGGCCTTTTGCTCACATGTTCTTTCCTGCGT
   +++++++++++++++++++++++++++++++++++++++++++++++++++++++++++ 2220
                          pBR322 origin ──────▶
3  A A F L R F L A F C W P F A H M F F P A 5' TATCCCCTGATTCTGTGGATAACCGTATTACCGCCTTTGAGTGAGCTGATACCGCTCGCC
   +++++++++++++++++++++++++++++++++++++++++++++++++++++++++++ 2280
3  L S P D S V D N R I T A F E . A D T A R 5' GCAGCCGAACGACCGAGCGCAGCGAGTCAGTGAGCGAGGAAGCGGAAGAGCGCCTGATGC
   +++++++++++++++++++++++++++++++++++++++++++++++++++++++++++ 2340
3  R S R T T E R S E S V S E E A E E R L M 5' GGTATTTTCTCCTTACGCATCTGTGCGGTATTTCACACCGCAATGGTGCACTCTCAGTAC
   +++++++++++++++++++++++++++++++++++++++++++++++++++++++++++ 2400
3  R Y F L L T H L C G I S H R N G A L S V 5' AATCTGCTCTGATGCCGCATAGTTAAGCCAGTATACACTCCGCTATCGCTACGTGACTGG
   +++++++++++++++++++++++++++++++++++++++++++++++++++++++++++ 2460
3  Q S A L M P H S . A S I H S A I A T . L 5' GTCATGGCTGCGCCCCGACACCCGCCAACACCCGCTGACGCGCCCTGACGGGCTTGTCTG
   +++++++++++++++++++++++++++++++++++++++++++++++++++++++++++ 2520
3  G H G C A P T P A N T R . R A L T G L S 5' CTCCCGGCATCCGCTTACAGACAAGCTGTGACCGTCTCCGGGAGCTGCATGTGTCAGAGG
   +++++++++++++++++++++++++++++++++++++++++++++++++++++++++++ 2580
                                                    ◀── RO_RF
3  A P G I R L Q T S C D R L R E L H V S E
```

FIG. 2E

```
5' TTTTCACCGTCATCACCGAAACGCGCGAGGCAGCTGCGGTAAAGCTCATCAGCGTGGTCG
   ++++|++++|++++|++++|++++|++++|++++|++++|++++|++++|++++|++++|  2640
                        ROP ORF
3  V F T V I T E T R E A A A V K L I S V V

5' TGAAGCGATTCACAGATGTCTGCCTGTTCATCCGCGTCCAGCTCGTTGAGTTTCTCCAGA
   ++++|++++|++++|++++|++++|++++|++++|++++|++++|++++|++++|++++|  2700
                        ROP ORF
3  V K R F T D V C L F I R V Q L V E F L Q

5' AGCGTTAATGTCTGGCTTCTGATAAAGCGGGCCATGTTAAGGGCGGTTTTTTCCTGTTTG
   ++++|++++|++++|++++|++++|++++|++++|++++|++++|++++|++++|++++|  2760
                        ROP ORF
3  K R . C L A S D K A G H V K G G F F L F

5' GTCACTGATGCCTCCGTGTAAGGGGGATTTCTGTTCATGGGGGTAATGATACCGATGAAA
   ++++|++++|++++|++++|++++|++++|++++|++++|++++|++++|++++|++++|  2820
   R..F
3  G H . C L R V R G I S V H G G N D T D E

5' CGAGAGAGGATGCTCACGATACGGGTTACTGATGATGAACATGCCCGGTTACTGGAACGT
   ++++|++++|++++|++++|++++|++++|++++|++++|++++|++++|++++|++++|  2880
3  T R E D A H D T G Y . . T C P V T G T

5' TGTGAGGGTAAACAACTGGCGGTATGGATGCGGCGGGACCAGAGAAAAATCACTCAGGGT
   ++++|++++|++++|++++|++++|++++|++++|++++|++++|++++|++++|++++|  2940
3  L . G . T T G G M D A A G P E K N H S G

5' CAATGCCAGCGCTTCGTTAATACAGATGTAGGTGTTCCACAGGGTAGCCAGCAGCATCCT
   ++++|++++|++++|++++|++++|++++|++++|++++|++++|++++|++++|++++|  3000
3  S M P A L R . Y R C R C S T G . P A A S

5' GCGATGCAGATCCGGAACATAATGGTGCAGGGCGCTGACTTCCGCGTTTCCAGACTTTAC
   ++++|++++|++++|++++|++++|++++|++++|++++|++++|++++|++++|++++|  3060
3  C D A D P E H N G A G R . L P R F Q T L

5' GAAACACGGAAACCGAAGACCATTCATGTTGTTGCTCAGGTCGCAGACGTTTTGCAGCAG
   ++++|++++|++++|++++|++++|++++|++++|++++|++++|++++|++++|++++|  3120
3  R N T E T E D H S C C C S G R R R F A A

5' CAGTCGCTTCACGTTCGCTCGCGTATCGGTGATTCATTCTGCTAACCAGTAAGGCAACCC
   ++++|++++|++++|++++|++++|++++|++++|++++|++++|++++|++++|++++|  3180
3  A V A S R S L A Y R . F I L L T S K A T
```

FIG. 2F

```
5' CGCCAGCCTAGCCGGGTCCTCAACGACAGGAGCACGATCATGCGCACCCGTGGCCAGGAC
                                                                3240
3   P P A . P G P Q R Q E H D H A H P W P G

5' CCAACGCTGCCCGAGATGCGCCGCGTGCGGCTGCTGGAGATGGCGGACGCGATGGATATG
                                                                3300
3   P N A A R D A P R A A A G D G G R D G Y

5' TTCTGCCAAGGGTTGGTTTGCGCATTCACAGTTCTCCGCAAGAATTGATTGGCTCCAATT
                                                                3360
3   V L P R V G L R I H S S P Q E L I G S N

5' CTTGGAGTGGTGAATCCGTTAGCGAGGTGCCGCCGGCTTCCATTCAGGTCGAGGTGGCCC
                                                                3420
3   S W S G E S V S E V P P A S I Q V E V A

5' GGCTCCATGCACCGCGACGCAACGCGGGGAGGCAGACAAGGTATAGGGCGGCGCCTACAA
                                                                3480
3   R L H A P R R N A G R Q T R Y R A A P T

5' TCCATGCCAACCCGTTCCATGTGCTCGCCGAGGCGGCATAAATCGCCGTGACGATCAGCG
                                                                3540
3   I H A N P F H V L A E A A . I A V T I S

5' GTCCAATGATCGAAGTTAGGCTGGTAAGAGCCGCGAGCGATCCTTGAAGCTGTCCCTGAT
                                                                3600
3   G P M I E V R L V R A A S D P . S C P .

5' GGTCGTCATCTACCTGCCTGGACAGCATGGCCTGCAACGCGGGCATCCCGATGCCGCCGG
                                                                3660
3   W S S S T C L D S M A C N A G I P M P P

5' AAGCGAGAAGAATCATAATGGGGAAGGCCATCCAGCCTCGCGTCGCGAACGCCAGCAAGA
                                                                3720
3   E A R R I I M G K A I Q P R V A N A S K

5' CGTAGCCCAGCGCGTCGGCCGCCATGCCGGCGATAATGGCCTGCTTCTCGCCGAAACGTT
                                                                3780
3   T . P S A S A A M P A I M A C F S P K R

5' TGGTGGCGGGACCAGTGACGAAGGCTTGAGCGAGGGCGTGCAAGATTCCGAATACCGCAA
                                                                3840
3   L V A G P V T K A . A R A C K I P N T A
```

FIG. 2G

```
5'  GCGACAGGCCGATCATCGTCGCGCTCCAGCGAAAGCGGTCCTCGCCGAAAATGACCCAGA
    +++++|++++|++++|++++|++++|++++|++++|++++|++++|++++|++++|++++| 3900
3    S  D  R  P  I  I  V  A  L  Q  R  K  R  S  S  P  K  M  T  Q

5'  GCGCTGCCGGCACCTGTCCTACGAGTTGCATGATAAAGAAGACAGTCATAAGTGCGGCGA
    +++++|++++|++++|++++|++++|++++|++++|++++|++++|++++|++++|++++| 3960
3    S  A  A  G  T  C  P  T  S  C  M  I  K  K  T  V  I  S  A  A

5'  CGATAGTCATGCCCCGCGCCCACCGGAAGGAGCTGACTGGGTTGAAGGCTCTCAAGGGCA
    +++++|++++|++++|++++|++++|++++|++++|++++|++++|++++|++++|++++| 4020
3    T  I  V  M  P  R  A  H  R  K  E  L  T  G  L  K  A  L  K  G

5'  TCGGTCGAGATCCCGGTGCCTAATGAGTGAGCTAACTTACATTAATTGCGTTGCGCTCAC
    +++++|++++|++++|++++|++++|++++|++++|++++|++++|++++|++++|++++| 4080
                                                              ⇐
3    I  G  R  D  P  G  A  .  .  V  S  .  L  T  L  I  A  L  R  S

5'  TGCCCGCTTTCCAGTCGGGAAACCTGTCGTGCCAGCTGCATTAATGAATCGGCCAACGCG
    +++++|++++|++++|++++|++++|++++|++++|++++|++++|++++|++++|++++| 4140
                            ══════════ lacI ORF ══════════
3    L  P  A  F  Q  S  G  N  L  S  C  Q  L  H  .  .  I  G  Q  R 5'  CGGGGAGAGGCGGTTTGCGTATTGGGCGCCAGGGTGGTTTTTCTTTTCACCAGTGAGACG
    +++++|++++|++++|++++|++++|++++|++++|++++|++++|++++|++++|++++| 4200
                            ══════════ lacI ORF ══════════
3    A  G  R  G  G  L  R  I  G  R  Q  G  G  F  S  F  H  Q  .  D 5'  GGCAACAGCTGATTGCCCTTCACCGCCTGGCCCTGAGAGAGTTGCAGCAAGCGGTCCACG
    +++++|++++|++++|++++|++++|++++|++++|++++|++++|++++|++++|++++| 4260
                            ══════════ lacI ORF ══════════
3    G  Q  Q  L  I  A  L  H  R  L  A  L  R  E  L  Q  Q  A  V  H 5'  CTGGTTTGCCCCAGCAGGCGAAAATCCTGTTTGATGGTGGTTAACGGCGGGATATAACAT
    +++++|++++|++++|++++|++++|++++|++++|++++|++++|++++|++++|++++| 4320
                            ══════════ lacI ORF ══════════
3    A  G  L  P  Q  Q  A  K  I  L  F  D  G  G  .  R  R  D  I  T 5'  GAGCTGTCTTCGGTATCGTCGTATCCCACTACCGAGATATCCGCACCAACGCGCAGCCCG
    +++++|++++|++++|++++|++++|++++|++++|++++|++++|++++|++++|++++| 4380
                            ══════════ lacI ORF ══════════
3    .  A  V  F  G  I  V  V  S  H  Y  R  D  I  R  T  N  A  Q  P
```

FIG. 2H

```
5' GACTCGGTAATGGCGCGCATTGCGCCCAGCGCCATCTGATCGTTGGCAACCAGCATCGCA
                                                                         4440
                              lacI ORF
3'   G  L  G  N  G  A  H  C  A  Q  R  H  L  I  V  G  N  Q  H  R 5' GTGGGAACGATGCCCTCATTCAGCATTTGCATGGTTTGTTGAAAACCGGACATGGCACTC
                                                                         4500
                              lacI ORF
3'   S  G  N  D  A  L  I  Q  H  L  H  G  L  L  K  T  G  H  G  T 5' CAGTCGCCTTCCCGTTCCGCTATCGGCTGAATTTGATTGCGAGTGAGATATTTATGCCAG
                                                                         4560
                              lacI ORF
3'   P  V  A  F  P  F  R  Y  R  L  N  L  I  A  S  E  I  F  M  P 5' CCAGCCAGACGCAGACGCGCCGAGACAGAACTTAATGGGCCCGCTAACAGCGCGATTTGC
                                                                         4620
                              lacI ORF
3'   A  S  Q  T  Q  T  R  R  D  R  T  .  W  A  R  .  Q  R  D  L 5' TGGTGACCCAATGCGACCAGATGCTCCACGCCCAGTCGCGTACCGTCTTCATGGGAGAAA
                                                                         4680
                              lacI ORF
3'   L  V  T  Q  C  D  Q  M  L  H  A  Q  S  R  T  V  F  M  G  E 5' ATAATACTGTTGATGGGTGTCTGGTCAGAGACATCAAGAAATAACGCCGGAACATTAGTG
                                                                         4740
                              lacI ORF
3'   N  N  T  V  D  G  C  L  V  R  D  I  K  K  .  R  R  N  I  S 5' CAGGCAGCTTCCACAGCAATGGCATCCTGGTCATCCAGCGGATAGTTAATGATCAGCCCA
                                                                         4800
                              lacI ORF
3'   A  G  S  F  H  S  N  G  I  L  V  I  Q  R  I  V  N  D  Q  P 5' CTGACGCGTTGCGCGAGAAGATTGTGCACCGCCGCTTTACAGGCTTCGACGCCGCTTCGT
                                                                         4860
                              lacI ORF
3'   T  D  A  L  R  E  K  I  V  H  R  R  F  T  G  F  D  A  A  S
```

FIG. 2I

```
5' TCTACCATCGACACCACCACGCTGGCACCCAGTTGATCGGCGCGAGATTTAATCGCCGCG
                                                                  4920
                              lacl ORF
3   F  Y  H  R  H  H  H  A  G  T  Q  L  I  G  A  R  F  N  R  R 5' ACAATTTGCGACGGCGCGTGCAGGGCCAGACTGGAGGTGGCAACGCCAATCAGCAACGAC
                                                                  4980
                              lacl ORF
3   D  N  L  R  R  R  V  Q  G  Q  T  G  G  G  N  A  N  Q  Q  R 5' TGTTTGCCCGCCAGTTGTTGTGCCACGCGGTTGGGAATGTAATTCAGCTCCGCCATCGCC
                                                                  5040
                              lacl ORF
3   L  F  A  R  Q  L  L  C  H  A  V  G  N  V  I  Q  L  R  H  R 5' GCTTCCACTTTTTCCCGCGTTTTCGCAGAAACGTGGCTGGCCTGGTTCACCACGCGGGAA
                                                                  5100
                              lacl ORF
3   R  F  H  F  F  P  R  F  R  R  N  V  A  G  L  V  H  H  A  G 5' ACGGTCTGATAAGAGACACCGGCATACTCTGCGACATCGTATAACGTTACTGGTTTCACA
                                                                  5160
                              lacl ORF
3   N  G  L  I  R  D  T  G  I  L  C  D  I  V  .  R  Y  W  F  H 5' TTCACCACCCTGAATTGACTCTCTTCCGGGCGCTATCATGCCATACCGCGAAAGGTTTTG
                                                                  5220
    lacl ORF
3   I  H  H  P  E  L  T  L  F  R  A  L  S  C  H  T  A  K  G  F 5' CGCCATTCGATGGTGTCCGGGATCTCGACGCTCTCCCTTATGCGACTCCTGCATTAGGAA
                                                                  5280
3   A  P  F  D  G  V  R  D  L  D  A  L  P  Y  A  T  P  A  L  G 5' GCAGCCCAGTAGTAGGTTGAGGCCGTTGAGCACCGCCGCCGCAAGGAATGGTGCATGCAA
                                                                  5340
3   S  S  P  V  V  G  .  G  R  .  A  P  P  P  Q  G  M  V  H  A 5' GGAGATGGCGCCCAACAGTCCCCCGGCCACGGGGCCTGCCACCATACCCACGCCGAAACA
                                                                  5400
3   R  R  W  R  P  T  V  P  R  P  R  G  L  P  P  Y  P  R  R  N
```

```
5' cgctacttgctgacttacaacattcaattaataaatggtcggtaatttacaatataaact
   +--+--+--+--+--+--+--+--+--+--+--+--+--+--+--+--+--+--+--+--+ 5880
   ─────────────────────────Reading Frame─────────────────────────
   ─────────────────────────── tr yscF ───────────────────────────
3'  A  L  L  A  D  L  Q  H  S  I  N  K  W  S  V  I  Y  N  I  N 5' caaccatagttcgtagcatgaaagacttaatgcaaggcatcctacagaagttcccataa
   +--+--+--+--+--+--+--+--+--+--+--+--+--+--+--+--+--+--+--+--+ 5939
   ─────────────────────────Reading Frame─────────────────────────
   ─────────────────────────── tr yscF ───────────────────────────
3'  S  T  I  V  R  S  M  K  D  L  M  Q  G  I  L  Q  K  F  P  .
```

USE OF YSCF, TRUNCATED YSCF AND YSCF HOMOLOGS AS ADJUVANTS

PRIORITY CLAIM

This application is a national phase entry under 35 U.S.C. §371 of International Patent Application PCT/US2012/043838, filed Jun. 22, 2012, designating the United States of America and published in English as International Patent Publication WO 2012/178078 A2 on Dec. 27, 2012, which claims the benefit under 35 U.S.C. §119(e) of U.S. Provisional Patent Application Ser. No. 61/499,924, filed Jun. 22, 2011, for "USE OF YSCF, TRUNCATED YSCF, AND YSCF HOMOLOGS AS ADJUVANTS," the disclosure of each of which is hereby incorporated herein by this reference in its entirety.

TECHNICAL FIELD

Embodiments of the disclosure relate generally to the field of biotechnology, and more particularly to compositions and methods for enhancing an immune response by providing an adjuvant of isolated or recombinant YscF, an isolated or recombinant fragment or truncation thereof, or a homolog thereof.

BACKGROUND

Plague is one of the most deadly infectious diseases on the planet, yet there is currently no available vaccine against *Yersinia pestis* approved for human use. Development of vaccines against the plague is especially important, because *Y. pestis* has the potential to be used as a bioterrorist weapon. *Y. pestis* is highly virulent, requiring only a small number of bacteria to initiate host infection (Titball et al., 1997). Although killed whole cell and attenuated live plague vaccines have been used in the past, the current focus of vaccine development against *Y. pestis* has shifted toward protein subunit vaccines, mainly because of cost and safety concerns.

Some of the most promising experimental protein subunits for use as subunit vaccines have been the F1 capsular antigen and the V antigen (LcrV), either used separately or as part of recombinant fusion proteins. However, acapsular, virulent strains of *Y. pestis* have been isolated. These spontaneous strains, without the F1 capsule, could evade immunity induced by F1 vaccinations. In such cases, a vaccine against F1 alone would not be effective. LcrV is another potential target for experimental vaccination protocols because of its important role in regulation of the Type III secretion system and its critical role in delivery of virulence proteins into the host eukaryotic cell. LcrV, in combination with F1 antigen, has been found to be protective against both bubonic and pneumonic plague. (Titball and Williamson, 2001). However, LcrV is known to have potent immunomodulatory effects that may not be desirable in a vaccine against *Y. pestis*, in that it may cause immunosuppression. Furthermore, LcrV exhibits serologic diversity, limiting the use of an LcrV vaccine produced against *Y. pestis* for protection against other *Yersinia* species.

The type III secretion apparatus is a conserved virulence mechanism required for virulence of *Y. pestis*. (Perry and Fetherson 1999). The type III secretion needle protein YscF has been suggested as an effective antigen for immunizing against *Yersinia* pathogens. See, e.g., U.S. Pat. Nos. 7,344,718 and 7,608,266 to Nilles, et al., the contents of which are incorporated herein by this reference. YscF protein is a surface-localized protein required both to secrete Yops, and to translocate toxins into the eukaryotic target cell. (Hoiczyk and Blobel, 2001).

DISCLOSURE

The following embodiments are meant to be exemplary and illustrative, and not limiting in scope.

In one aspect, a composition is provided comprising an antigen and an effective adjuvanting amount of either wild type YscF (wtYscF), truncated YscF (trYscF), or a fragment of YscF (frYscF).

In some embodiments, the antigen may be a *Yersinia* antigen. In certain embodiments, the antigen may be a *Yersinia pestis* antigen. In certain embodiments, the *Yersinia pestis* antigen may comprise LcrV, the F1 antigen, or combinations thereof. In other embodiments, the antigen may comprise a YscF homolog, such as PrgI, MxiH, SsaG, truncated forms, or fragments thereof. In other embodiments, a YscF homolog, truncated form, or fragment thereof, may be used as an adjuvant.

In one aspect, a composition is provided comprising a *Yersinia* antigen and a means for increasing the immunogenicity of the antigen.

In another aspect, a process for producing a composition is disclosed, wherein the process comprises providing a host cell with an expression vector encoding either YscF, frYscF, or trYscF, the host cell expressing the YscF, frYscF, or trYscF. In certain embodiments, the YscF, frYscF, or trYscF may be mixed with a suitable carrier, diluent, or excipient. The YscF, frYscF, or trYscF may be isolated or purified from the host cells prior to mixing with a carrier, diluent, or excipient. In some embodiments, the process may comprise mixing LcrV, the F1 antigen, or combinations of these with the diluent, carrier, or excipient. In other embodiments, the composition produced by the process may comprise mixing PrgI, MxiH, SsaG, fragments or truncated forms thereof, or combinations of these, with a suitable diluent, carrier, or excipient.

In another aspect, a method is provided for inducing an enhanced immune response using an antigenic composition comprising an antigen and an effective adjuvanting amount of wtYscF, frYscF, trYscF, or a YscF homolog.

In another aspect, an improved method for vaccinating an animal against *Yersinia* infection is provided, wherein a vaccine composition of the type having an adjuvant and a *Yersinia* antigen is administered, and the adjuvant comprises YscF, an effective fragment of YscF, truncated YscF, or YscF homolog.

In another aspect, a method is provided for screening for an immunological response to a *Yersinia* pathogen, wherein mammalian cells are exposed to a *Yersinia* antigen, and wtYscF, frYscF, trYscF, a YscF homolog, fragments or truncated forms thereof, or combinations thereof, are introduced.

BRIEF DESCRIPTION OF THE DRAWINGS

Figure 2K:
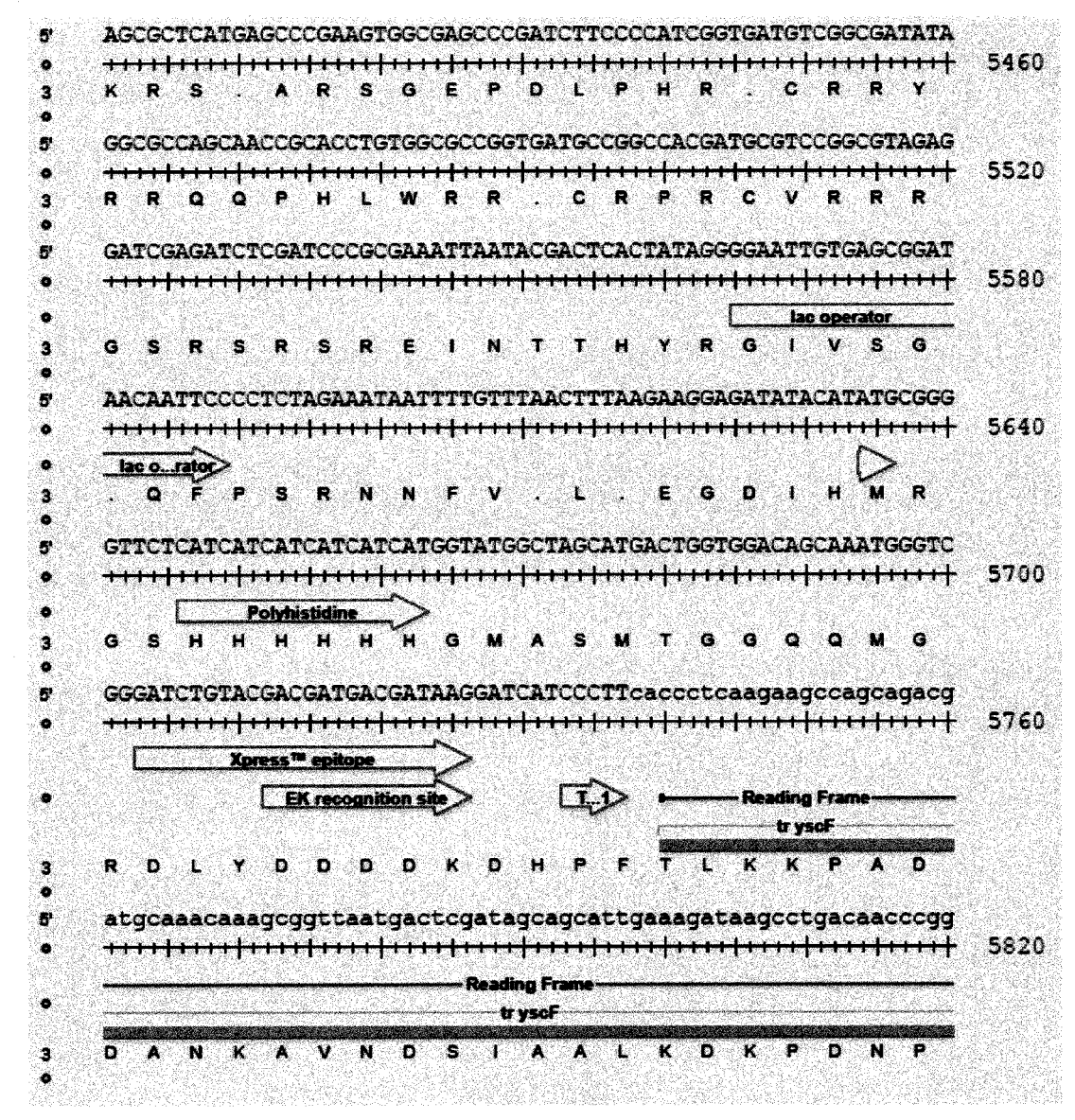

FIGS. 2A through 2L contain the sequence of the pMNT67 plasmid for use in some embodiments (SEQ ID NO:5).

FIG. 4 is a histogram showing pooled mouse serum G-CSF, GM-CSF, IFN-γ, MIP-1b and IL-5 levels in mice vaccinated with YscF or trYscF.

Figure 14:
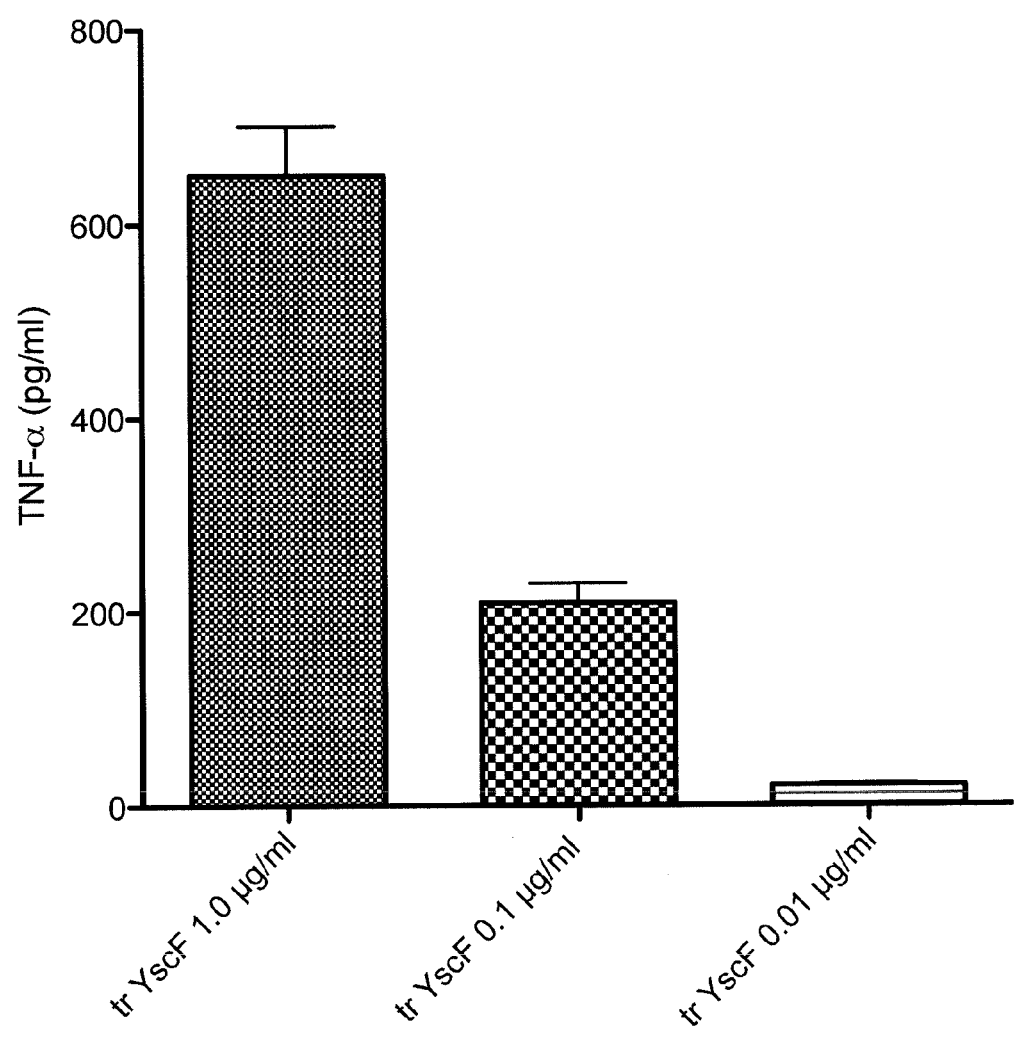

FIG. 14 is a histogram showing TNF-α levels in THP-1 cell supernatants of cells treated with varying doses of trYscF.

SEQUENCES USED

The following amino acid or nucleotide sequences may be used in various aspects and embodiments:
SEQ ID NO:1 is the wtYscF amino acid sequence;
SEQ ID NO:2 is the trYscF amino acid sequence;
SEQ ID NO:3 is the TrncYscFStartMT primer;
SEQ ID NO:4 is the TrnctYscFStopMT primer;
SEQ ID NO:5 is the pMNT67 plasmid sequence;
SEQ ID NO:6 is the tr-yscF coding sequence from pMNT67;
SEQ ID NO:7 is the wtPrgI amino acid sequence;
SEQ ID NO:8 is the trPrgI amino acid sequence;
SEQ ID NO:9 is the wtMxiH amino acid sequence;
SEQ ID NO:10 is the trMxiH amino acid sequence;
SEQ ID NO:11 is the wtSsaG amino acid sequence;
SEQ ID NO:12 is the His6-trSsaG amino acid sequence;
SEQ ID NO:13 is the His6-trYscF amino acid sequence;
SEQ ID NO:14 is the His6-tr-yscF coding sequence from pET200;
SEQ ID NO:15 is the wt-prgI coding sequence;
SEQ ID NO:16 is the prgI DNA construct from pET200;
SEQ ID NO:17 is the wtPrgI forward primer;
SEQ ID NO:18 is the wtPrgI reverse primer;
SEQ ID NO:19 is the His6-PrgI amino acid sequence;
SEQ ID NO:20 is the wt-mxiH coding sequence;
SEQ ID NO:21 is the tr-mxiH coding sequence;
SEQ ID NO:22 is the wt-ssaG coding sequence;
SEQ ID NO:23 is the His6-SsaG amino acid sequence;
SEQ ID NO:24 is the His6-ssaG coding sequence;
SEQ ID NO:25 is the His6-tr-ssaG DNA construct; and
SEQ ID NO:26 is a Type III needle protein minor epitope amino acid sequence.

DETAILED DESCRIPTION

In embodiments, an antigenic composition is provided comprising an antigen and an effective adjuvanting amount of a Type III needle protein.

In some embodiments, the Type III needle protein may comprise a YscF protein (SEQ ID NO:1). A consensus sequence for YscF is disclosed in U.S. Pat. No. 7,608,266 to Nilles et al. As used herein, the terms "YscF," "wtYscF," "wild type YscF," and "whole YscF," unless otherwise indicated, refer to SEQ ID NO:1.

Figure 1A:
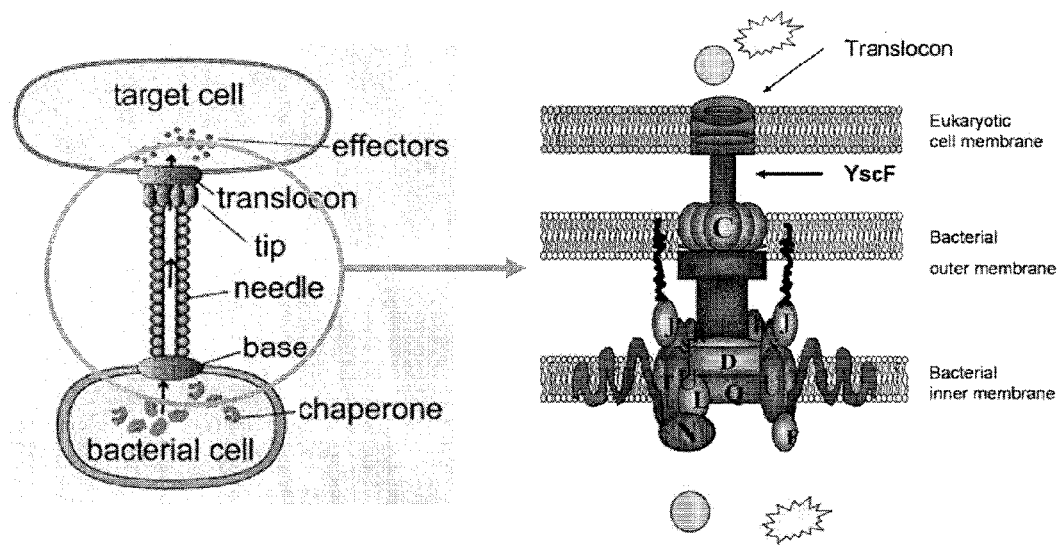
FIGS. 1A and 1B are illustrations depicting an aspect of the disclosure.

As described herein, the term "YscF" may refer to the YscF protein originating from any of *Y. pestis, Y. pseudotuberculosis*, and *Y. enterocolitica*, unless otherwise specified. The YscF proteins of *Y. pestis, Y. enterocolitica*, and *Y pseudotuberculosis* have substantially similar sequences. One aspect of the YscF type III secretion needle complex is illustrated in FIG. 1A. A needle complex is shown engaging a bacterial cell with a eukaryotic host (right, and circled at left). The needle complex is made up of several such YscF proteins (B).

In other embodiments, the Type III needle protein may comprise an effective fragment of the YscF protein (frYscF). As used herein, the terms "frYscF" or "YscF fragment," refers to any segment of the YscF protein that comprises a portion, but less than the entire sequence, of the wild type YscF protein (SEQ ID NO:1). In some embodiments, the YscF fragment may constitute a contiguous or non-contiguous segment of wtYscF. As used herein, the tem). "effective fragment of YscF" may refer to a fragment of the YscF protein that will function to enhance an immune response.

Figure 1B:
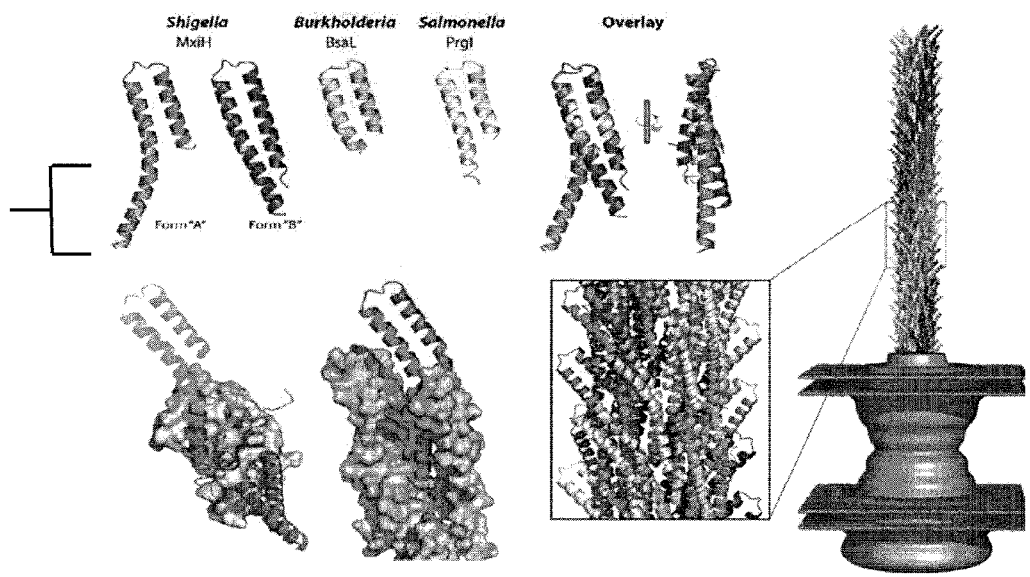
Figure 3:
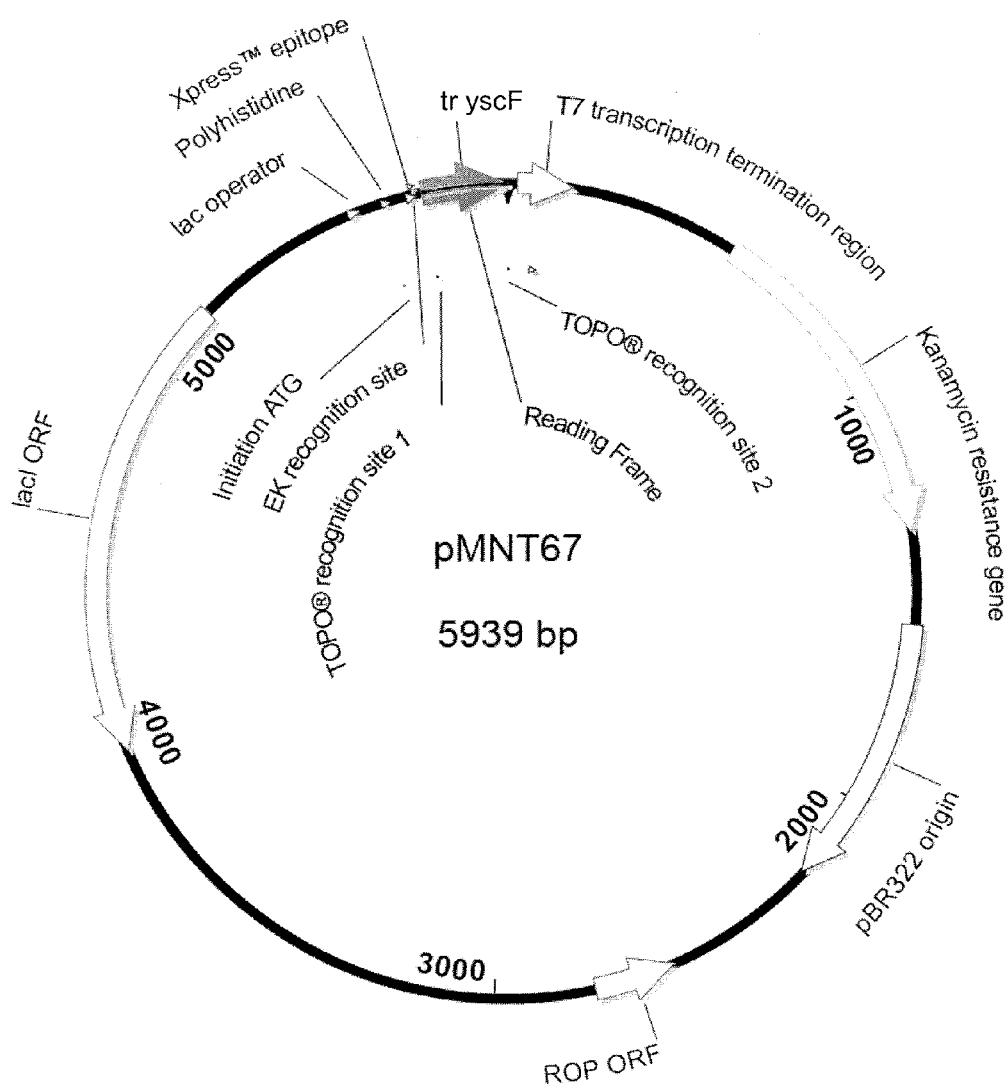
FIG. 3 is a map of the pMNT67 plasmid for use in some embodiments.

In still other embodiments, the Type III needle protein may comprise a truncated YscF protein (trYscF) (SEQ ID NO:2). An N-terminally truncated YscF (trYscF) for use in some embodiments contains 65 amino acids (SEQ ID NO:2). It will be appreciated that trYscF differs from YscF (SEQ ID NO:1) in that the first twenty-two N-terminal amino acids have been truncated, leaving only the C-terminal 3/4 of the protein. The deleted segment is indicated by brackets in MxiH, the *Shigella* homolog of YscF. See FIG. 1B on left. In the resulting trYscF protein, amino acids 23-26 (PDNP) map to the turn between the two alpha helices of wild type YscF. A minor epitope lies within this region between the two alpha helices, based on the MxiH crystal structure. YscF thus has a concealed pathogen associated molecular pattern (PAMP) that is exposed upon truncation of the N-terminus.

In embodiments, the antigenic composition may comprise wtYscF (SEQ ID NO:1), frYscF, trYscF (SEQ ID NO:2), or YscF homologs as isolated or recombinant proteins. In some embodiments, the composition may comprise wtYscF, frYscF, trYscF, or YscF homologs as separate proteins, combined with antigens or other adjuvants, or as parts of recombinant fusion proteins.

In embodiments, wtYscF (SEQ ID NO:1), frYscF, trYscF (SEQ ID NO:2), or YscF homologs, may comprise a substantially similar protein sequence. Generally, polypeptide sequence variants of the invention will have at least 60 percent, 65 percent, 70 percent, 75 percent, 76 percent, 77 percent, 78 percent, 79 percent, 80 percent, 81 percent, 82 percent, 83 percent, 84 percent, 85 percent, 86 percent, 87 percent, 88 percent, 89 percent, 90 percent, 91 percent, 92 percent, 93 percent, 94 percent, 95 percent, 96 percent, 97 percent, 98 percent, or 99 percent sequence identity to the wtYscF (SEQ ID NO:1), frYscF, trYscF (SEQ ID NO:2) or YscF homologs, wherein the percent sequence identity is based on the entire sequence and may be determined by GAP 10 analysis using default parameters, or other suitable sequence comparison tool. GAP uses the algorithm of Needleman and Wunsch (1970) to find the alignment of two complete sequences that maximizes the number of matches and minimizes the number of gaps.

In embodiments, the antigen for use in an antigenic composition may be a *Yersinia* pathogen. In certain embodiments, the antigen may be a *Yersinia pestis* pathogen. In certain embodiments, for example, the *Yersinia* needle tip associated protein, LcrV, or the F1 antigen, or combinations of these, may be used as the antigen. In some embodiments, whole live or attenuated *Yersinia* cells may be used as antigens.

Other bacterial species possess pathogenesis-related type III secretion systems with homologs to YscF from *Yersinia*. The YscF homologs PrgI, MxiH, and SsaG, from pathogenic *Salmonella, Shigella*, and *Salmonella* Spi2, respectively, have been demonstrated to form a needle structure that protrudes from the surface of bacterial cells. (Blocker et al., 2001; Kubori, 2000). In embodiments, YscF and trYscF homologs from bacterial species and genera related to *Yersinia pestis* with type III secretion systems may be used as antigens. In some embodiments, for example, the YscF homologs PrgI (SEQ ID NO:7), MxiH (SEQ ID NO:9), and/or SsaG (SEQ ID NO:11) may be used as antigens in the antigenic composition. In other embodiments, fragments or truncated forms of these or related antigens may be used, including, for example, trPrgI (SEQ ID NO:8), trMxiH (SEQ ID NO:10), and trSsaG (SEQ ID NO:12). Combinations of these may also be used in certain embodiments. In still other embodiments, YscF homologs, fragments or truncated forms thereof, may be used as adjuvants in the antigenic composition.

The term "effective adjuvanting amount," as used herein, is defined as an amount of YscF (SEQ ID NO:1), frYscF, trYscF (SEQ ID NO:2), YscF homolog, or fragments or truncated forms thereof, that will function as an adjuvant to enhance an immune response. Immunogenicity of particular antigen and antigen-adjuvant compositions may be determined by methods known to those of skill in the art, including measuring induced proinflammatory cytokines, measuring antigen- or adjuvant-specific antibody production, or measuring activation of inflammatory pathways, including the NF-κB pathway.

In various embodiments, the antigenic composition may further comprise a diluent, a carrier, or an excipient. Suitable diluents, carriers, and excipients are known to those of skill in the art.

In an additional embodiment, a method is disclosed for inducing an enhanced immune response using an antigenic composition comprising an antigen and an effective adjuvanting amount of YscF protein. In some embodiments, the YscF protein may be a fragment of YscF protein (frYscF), or a truncated YscF protein (trYscF) (SEQ ID NO:2). In some embodiments, the antigen for use in the method may comprise a *Yersinia* antigen, such as a pathogenic antigen from *Yersinia pestis*. In certain embodiments, the antigen may comprise LcrV or the F1 antigen, or combinations thereof. In other embodiments, the antigen used in the method for inducing an enhanced immune response may comprise PrgI (SEQ ID NO:7), MxiH (SEQ ID NO:9), SsaG (SEQ ID NO:11), fragments or truncated forms thereof, or combinations thereof.

In some embodiments, YscF (SEQ ID NO:1), frYscF, trYscF (SEQ ID NO:2), YscF homolog, fragments or truncated forms thereof, or combinations thereof, may be administered as an effective adjuvant in, for example, mammalian cell culture, or ex vivo cell preparations. In other embodiments, YscF (SEQ ID NO:1), frYscF, trYscF (SEQ ID NO:2), YscF homologs, fragments or truncated forms thereof, or combinations thereof, may be administered as an adjuvant to enhance an immune response in an animal, for example, a human or non-human primate, mouse, rat, cow, goat, sheep, horse, cat, dog, or other mammal.

In other embodiments, a process for producing a composition is disclosed, wherein the process comprises providing a host cell with an expression vector, the expression vector encoding either YscF (SEQ ID NO:1), frYscF, or trYscF (SEQ ID NO:2), the host cell expressing the YscF, frYscF, or trYscF. In embodiments, the YscF, frYscF, or trYscF may be mixed with a suitable carrier, diluent, or excipient. In some embodiments, the process may comprise mixing PrgI, MxiH, SsaG, with a suitable carrier, diluent, or excipient. In other embodiments, fragments, or truncated forms of PrgI, MxiH, SsaG, or combinations of these, may be mixed with a carrier, diluent, or excipient. In still other embodiments, the composition produced by the process may comprise mixing LcrV, the F1 antigen, fragments or truncated forms thereof, or combinations of these with a suitable carrier, diluent, or excipient.

In embodiments, YscF (SEQ ID NO:1), frYscF, trYscF (SEQ ID NO:2), a YscF homolog, or fragments or truncated forms thereof, may be isolated or obtained using recombinant methods known to those of skill in the art. In one aspect of the invention, truncated YscF, as disclosed herein, may be expressed by cloning a portion of the YscF subunit into a suitable expression vector using methods known in the art, where the portion of the gene lacks the 66 bp N-terminal region. A plasmid bearing the cloned YscF, YscF fragment, or truncated YscF may be used to transform a bacterial host, such as *E. coli*, and transformants selected using a suitable selection medium. Culture and lysis of successfully transformed host cells may be used to release the YscF protein, YscF fragment or truncated YscF protein, which then may be purified according to known methods. Other suitable systems may also be used, including eukaryotic or other prokaryotic systems, for expressing wtYscF, YscF fragment, or truncated YscF. Related homologs of YscF, or fragments or truncated forms thereof, as discussed herein, may be expressed using similar methods.

In addition to the nucleic acid molecular sequences disclosed herein, it is understood that substantially similar nucleic acid sequences, encoding for substantially similar or the same products, are further disclosed. Generally, nucleic acid molecular sequence variants will have at least 46 percent, 48 percent, 50 percent, 52 percent, 53 percent, 55 percent, 60 percent, 65 percent, 70 percent, 75 percent, 76 percent, 77 percent, 78 percent, 79 percent, 80 percent, 85 percent, 86 percent, 87 percent, 88 percent, 89 percent, 90 percent, 91 percent, 92 percent, 93 percent, 94 percent, 95 percent, 96 percent, 97 percent, 98 percent or 99 percent sequence identity to the nucleotide sequence encoding wtYscF, frYscF, trYscF, YscF homolog, or fragments of truncated forms thereof, wherein the percent sequence identity is based on the entire sequence, and is determined using methods known in the art.

For example, as known in the art, the degeneracy of the genetic code and the "wobble" hypothesis allows for nucleotide substitutions to occur, with the protein encoded retaining a substantially similar or identical structure, function, and/or immunogenic effect in various model systems, because some amino acids can be encoded by more than one codon. Similarly, some amino acid substitutions may not significantly alter the structure, function, and/or immunogenic properties of the protein. Accordingly, nucleotide substitutions in the nucleic acids, or amino acid substitutions in the isolated or recombinant wtYscF, frYscF, trYscF, or homologs thereof, which encode for or constitute proteins having substantially the same structure, function or immunogenic properties are encompassed herein.

In embodiments, YscF (SEQ ID NO:1), frYscF, trYscF (SEQ ID NO:2), or a YscF homolog, is used in a method for manufacturing a medicament. In some embodiments, the YscF protein, YscF fragment, truncated YscF, or YscF homolog is used as an effective adjuvant to increase the immunogenicity of an antigen in an immune response against *Yersinia* or related species.

In embodiments, a vaccine composition of the type having an adjuvant and an antigen is disclosed, wherein the improvement may comprise using YscF (SEQ ID NO:1), frYscF, trYscF (SEQ ID NO:2), or YscF homolog, as an adjuvant in the vaccine composition. In other embodiments, a method for manufacturing such a vaccine is disclosed, wherein the improvement may comprise adding wtYscF protein (SEQ ID NO:1), YscF fragment, truncated YscF (SEQ ID NO:2), or a YscF homolog, as an adjuvant, to a *Yersinia* antigen, in the vaccine composition.

In embodiments, a composition is disclosed, wherein the composition comprises a *Yersinia* antigen and a means for increasing the immunogenicity of the antigen. In some embodiments, the means for increasing the immunogenicity of the antigen may be provided by including YscF (SEQ ID NO:1), frYscF, trYscF (SEQ ID NO:2), a YscF homolog, fragments or truncated forms thereof, or combinations thereof, as effective adjuvants with the *Yersinia* antigen.

It is possible that the N-terminus of YscF is a necessary constituent of the type III secretion needle for evading detection by the eukaryotic immune system. Candidate epitopes of antigens for use in some embodiments may be identified by structural analysis of the native protein or homologous proteins, revealing potential surface-accessible epitopes. A surface-accessible epitope is expected to have improved immunogenicity. Epitopes of YscF for use in some embodiments may be further identified and verified by covalently binding a series of overlapping peptides to a membrane to expose immunogenic regions of the protein, and immunoblotting with YscF antibodies. Based on these analyses, in preference to targeting YscF protein epitopes in a fully assembled needle structure, a truncated forms of YscF (SEQ ID NO:2), which includes its C-terminal sequence that shares some similarities with flagellin, as well as the unassembled wild type YscF protein (SEQ ID NO:1), was developed. The N-terminally truncated YscF (trYscF) (SEQ ID NO:2) lacks the dominant, major epitope, exposing the minor epitope, and may permit a stronger, protective antibody response. Treatment of THP-1 cells with YscF homologs, fragments, or truncated forms thereof, may have similar effects.

In some embodiments, an antigenic composition is provided, comprising a Type III needle protein, wherein the Type III needle protein comprises the amino acid consensus sequence XYZP (SEQ ID NO:26), where X represents either proline or asparagine; Y represents either aspartic acid or serine; Z represents either aspartic acid or asparagine; and P represents proline. In certain embodiments, the Type III needle protein may comprise the amino acid consensus sequence XYZP, where X represents proline; Y represents aspartic acid; Z represents asparagine; and P represents proline.

In embodiments, YscF, truncated YscF, a YscF fragment, YscF homolog, fragments or truncated forms thereof, or combinations thereof, may also be effective adjuvants against pathogens other than *Yersinia*. In some embodiments, YscF, truncated YscF, a YscF fragment, YscF homolog, fragments or truncated forms thereof, or combinations thereof, may be effective adjuvants against other bacterial species, or non-bacterial pathogens.

While not being bound to any particular theory, treatment of human THP-1 macrophage cells with wild-type YscF, truncated YscF, or a YscF fragment, may operate by activation of the NF-κB pathway. A truncated YscF protein appears to stimulate macrophages to activate the NF-κB pathway and subsequent production of proinflammatory cytokines. See, e.g., Examples 1 and 5-9. TrYscF may also activate pathways other than the NF-κB pathway; for example, trYscF may stimulate macrophages to produce proinflammatory cytokines via an inflammasome. Proinflammatory cytokines that may be associated with YscF, trYscF, frYscF, or YscF homolog exposure in vitro and in-vivo include, for example, IL-1β, IL-2, IL-4, IL-12, IL-6, IL-8, IL-10, IFN-γ, GM-CSF and TNF-α.

Flagellin, a strongly immunogenic bacterial antigen, is recognized by Toll-like receptor 5 (TLR5) (Hayashi et al., 2001). TLR5 stimulation induces NF-κB that, in turn, moves into the nucleus and induces the production of cytokines and nitric oxide. Specifically, nitric oxide production requires an interaction between flagellin and a heterodimer of TLR5 and TLR4 (Mizel et al., 2003). The nature of proinflammatory stimulation in the macrophage can be studied by examining the activation state of proteins important in cytokine activation pathways, such as the NF-κB pathway. Specifically, IKKα, IKKβ, NF-κB p65, and IκBα play important roles in the NF-κB pathway (Ghosh and Karin, 2002). Comparing the different levels of proteins in the NF-κB pathway is one method of determining if the induction of proinflammatory cytokines observed in in vivo and in vitro studies with trYscF (SEQ ID NO:2) is dependent on TLR activation. NF-κB is present in the cytosol in an inactivated form prior to activation by some form of PRR stimulation. When NF-κB is in an inactivated form in the cytosol, it is found in a complex with IκB proteins (IκBα or IκBα/β/ε) (Viatour et al., 2005). IκB proteins act as inhibitors of NF-κB. When IκBα is phosphorylated (at Ser32 and Ser36), NF-κB is released and IκBα is degraded by ubiquitin-mediated proteasome-dependent degradation (Scheidereit, 2006). NF-κB is then free to translocate into the nucleus and induce the production of a series of proinflammatory cytokines. In this case, the absence or lack of detection of IκBα lysate samples from in vitro experiments would indicate activation of NF-κB.

IκB phosphorylation is regulated by activation of the IκB kinase, or IKK. The IKK complex is composed of three subunits (id.). IKKα and IKKβ mentioned above are the catalytic subunits of the IKK complex. IKK is activated by phosphorylation of IKKα (Ser176 and Ser180) and IKKβ (Ser177 and Ser181) (id.). Detection of higher levels of phosphorylated IKKα and IKKβ could also indicate NF-κB activation. The NF-κB family of proteins includes the p65/RelA protein (Ghosh and Karin, 2002). P65, along with p50, are translocated into the nucleus to induce transcription of genes once in their activated form (free from the complex with IκB proteins). Prior to translocation, p65/RelA is phosphorylated at Ser536, Ser276, and Ser468 (Viatour et al., 2005). Phosphorylation at Ser276 enhances transcription activity while phosphorylation at Ser468 inhibits p65 activity. Phosphorylation at Ser536 is important for activation, regulation, transcriptional activity and nuclear localization (Ghosh and Karin, 2002). Therefore, detection of Ser536-phosphorylated p65 is potentially a good method of assessing the levels of p65 translocation into the nucleus.

The invention is further described in the following illustrative examples. Concepts described in any specific heading are generally applicable in other sections throughout the application.

EXAMPLES

Example 1

YscF Overview

Truncated YscF (SEQ ID NO:2) significantly increased proinflammatory cytokines, in vivo, in trYscF-immunized mice or, in vitro, in trYscF-treated mouse macrophages, compared to wild type YscF (SEQ ID NO:1). C57BL/6N mice immunized with trYscF (SEQ ID NO:2) produced serum antibodies specific to the surface-accessible minor epitope of trYscF. In addition, human THP-1 macrophage cells treated, in vitro, with trYscF stimulated higher levels of proinflammatory cytokine production than THP-1 cells treated with either wtYscF or flagellin. These cytokines included IL-6, IL-8, IL-10, GM-CSF and TNF-α, but treatment with trYscF did not trigger IL-2 or IL-4 release.

Both wtYscF (SEQ ID NO:1) and trYscF (SEQ ID NO:2) induced the NF-κB pathway in THP-1 cells, in vitro, and in primary mouse peritoneal macrophages cells from C57BL/6N mice, ex vivo, suggesting that a TLR-mediated pathway may be activated when wtYscF and trYscF come into contact with eukaryotic cells. Cell lysates from HeLa cells infected with *Y. pestis* in the presence of a 1:10 dilution of mouse anti-trYscF sera reduced YopE translocation, indicating at least partial neutralization of the T3SS needle, in vitro.

B6 mice were vaccinated to evaluate the ability of wtYscF (SEQ ID NO:1) or trYscF (SEQ ID NO:2) to induce heterologous protection against *Y. pestis* infection. Including wtYscF or trYscF with the LcrV antigen increased LcrV-mediated protection. Truncated forms of PrgI (SEQ ID NO:8), MxiH (SEQ ID NO:10), and SsaG (SEQ ID NO:12) also induced cytokine expression. Truncated YscF, PrgI and SsaG proteins strongly induced THP-1 cells containing an AP-1 and MyD88-responsive SEAP reporter gene. Full-length proteins were weaker inducers of the SEAP reporter, but still induced the reporter to about double the activity of the un-induced cells, demonstrating that reporter induction by the needle proteins is either MyD88 or AP-1 dependent. TLR expression was induced in HEK293 cells in the presence of purified YscF and trYscF and neutralizing antibody against either TLR1 or TLR6, suggesting that YscF/trYscF are sensed by TLR2 and TLR6, and induce a MyD88 pathway, resulting in pro-inflammatory cytokine expression.

Example 2

Epitope Mapping

The YscF subunit was examined to improve the immunogenicity of the YscF-based antigenic composition. Structural analysis of YscF revealed that some epitopes of the needle protein were likely to be concealed in a fully-assembled needle. Furthermore, analysis of YscF suggested a partial resemblance to a highly immunogenic bacterial protein, flagellin. Using a series of overlapping peptides covalently bound to a PepSpot membrane (JPT Peptide Technologies GmbH), immunogenic regions of YscF were determined by immunoblotting the membranes with rabbit and mouse antibodies to YscF. The amino acid sequences for these overlapping peptides map to the N-terminus of YscF, revealing a potential strong epitope. Based on the structure of the YscF homolog, MxiH (*Shigella flexneri*) (Deane et al., 2006), a second epitope may be involved in LcrV binding at the tip of the needle, though there is currently no evidence of a YscF epitope that interacts with LcrV. A minor YscF epitope was also detected. This minor epitope is predicted to be located in a turn between the two alpha-helices in the MxiH structure that are potentially surface accessible to antibodies (Kenjale et al., 2005).

Using the MxiH structure in conjunction with the location of major and minor epitopes allowed the design of a modified YscF subunit that was surface accessible to antibodies. A truncated YscF (SEQ ID NO:2), which included the surface-accessible minor epitope region, was constructed by removing the N-terminal portion of the protein containing the major epitope. The removal of the major epitope region not only increases recognition of the minor epitope by the antibodies of the innate immune system to produce YscF-specific antibodies, but also induces immunogenicity of the protein as indicated by significantly elevated levels of proinflammatory cytokines in trYscF-immunized mice or trYscF-treated macrophage cell culture, when compared to wild type YscF. These experimental results indicated that YscF protein, especially the truncated form of the protein, can be used as an immunogenic adjuvant.

Example 3

Generation of trYscF

PCR primers were designed to clone a fragment of YscF missing the 66-bp region encoding for the N-terminus of YscF into an expression vector, pET200 (Invitrogen, Carlsbad, Calif.). The primers used were TrncYscFStartMT (5'-CACCCTCAAGAAGCCAGCAGACGATG-CAAACAAAGCGG-3') (SEQ ID NO:3) and TrnctYscFStopMT (5'-TTATGGGAACTTCTGTAGGAT-GCCTTGCATTAA-3') (SEQ ID NO:4). The resulting PCR fragment was cloned into pET200 TOPO® (Invitrogen). The resulting plasmid, pMNT67 (FIGS. 2A through 2L and 3), was used to transform *E. coli* BL21 cells (EMD4Biosciences (Novagen), Gibbstown, N.J.) for overexpression of his-tagged trYscF. SEQ ID NO:5 shows the nucleic acid sequence of the pMNT67 plasmid construct according to certain embodiments. Cells were then recovered by centrifugation (18,000×g for 15 min), resuspended in 1×PBS, and lysed using a French Press pressure cell at 20,000 psi. Slurry recovered from French pressing was centrifuged (3,000×g for 15 minutes) twice and the supernatant was used for further protein purification. TrYscF (SEQ ID NO:2) was purified using Talon resin (Clontech, Mountain View, Calif.) following the manufacturer's instructions. Purified protein was concentrated using Centricon® Plus-70 (Millipore, Billerica, Mass.) filters. Concentrated protein was dialyzed using Slide-A-Lyzer® dialysis cassettes (Pierce).

TrYscF samples were separated by SDS-PAGE and stained using Coomassie blue (Imperial Blue stain, Pierce) or transferred to western blots to test for purity. Samples were boiled for 8 minutes in 2×SDS sample buffer prior to loading on 15% SDS-PAGE gels. Gels were either stained with Imperial Blue, or proteins were transferred to Immobilon-P membranes (Millipore) in carbonate buffer. Immunoblots were probed with mouse anti-YscF (lab stock) or rabbit anti-YscF antibody (lab stock), washed and then probed with goat anti-mouse or goat anti-rabbit alkaline-phosphatase conjugated secondary antibody. Immunoblots were developed using nitroblue tetrazolium and 5-bromo-4-chloro-3-indolyl-phosphate.

Example 4

Immunization of Mice with Truncated YscF Results in a Decrease in Mean Time to Death in Mouse Models of Plague Work was conducted on the basis that trYscF (missing the dominant epitope) would drive the immune response towards the minor surface accessible epitope. Six to eight week old female C57BL/6N mice (Harlan, Madison, Wis.) were immunized with either wild type YscF (SEQ ID NO:1) or trYscF (SEQ ID NO:2). Negative control mice were mock immunized with phosphate-buffered saline (1×PBS). Protein samples were all purified and in PBS. Mice were immunized intraperitoneally (i.p.) with 100 µl doses; the primary dose contained 40 µg of either YscF or trYscF, and two boosts containing 20 µg of protein were administered at two and four weeks post-primary immunization. YscF and trYscF were emulsified with complete Freund's adjuvant (CFA) for the primary immunization and with incomplete Freund's adjuvant (IFA) for the boosts. Mock-treated mice were vaccinated with PBS plus CFA (for the primary vaccine) or IFA (for boosters). C57BL/6N mice were infected with *Y. pestis* (Table 2) 2 weeks after the final immunization. A 10 ml culture of *Y. pestis* was grown overnight at 26° C., subcultured to an $OD_{620}$ of 0.1 the next morning, grown to an $OD_{620}$ of 1.0, centrifuged (18,000×g for 15 minutes) and resuspended in PBS. The bacterial suspension was diluted into three doses of $1 \times 10^3$, $1 \times 10^2$, and $1 \times 10^1$ CFUs for each of the three different infectious dose groups. 50 µl of each dose was plated to determine actual CFUs and 50 µl of each dose was used to infect mice. Mice were challenged intravenously (i.v.) via the retro-orbital sinus with $10^1$ to $10^3$ CFU of *Y. pestis* KIM5 in PBS. Plates were counted in order to ensure that mice were infected with the proper infectious dose. Mice were monitored for 21 days post-infection. All mouse studies were approved by UND's IACUC. Survivors were euthanized by $CO_2$ inhalation, according to the guidelines of the Panel on Euthanasia of the American Veterinary Medical Association.

It was found that C57BL/6N mice immunized with trYscF (SEQ ID NO:2) had a decreased mean time to death after infection with *Y. pestis*, compared to mock immunized mice or mice immunized with wild type YscF (SEQ ID NO:1).

Experiments were conducted to determine if trYscF was contributing to the decreased mean time to death or if another factor contributed to this phenomenon. First, the purity of trYscF protein that was used to immunize mice was verified. Second, serum from mice was analyzed to ensure that mice developed antibodies to trYscF. Protein samples probed by mouse sera (pre vaccination or post vaccination and pre infection) on blots verified the presence of antibodies to trYscF in mice immunized with this protein. The trYscF specific antibody titer was determined to be 1:50,000. These results indicate that the lower mean time to death was not due to a lack in antibody production to the antigen, or the presence of arbitrary proteins in the mixture.

Example 5

Serum Cytokine Levels are Elevated in Mice Immunized with Truncated YscF

Figure 4:
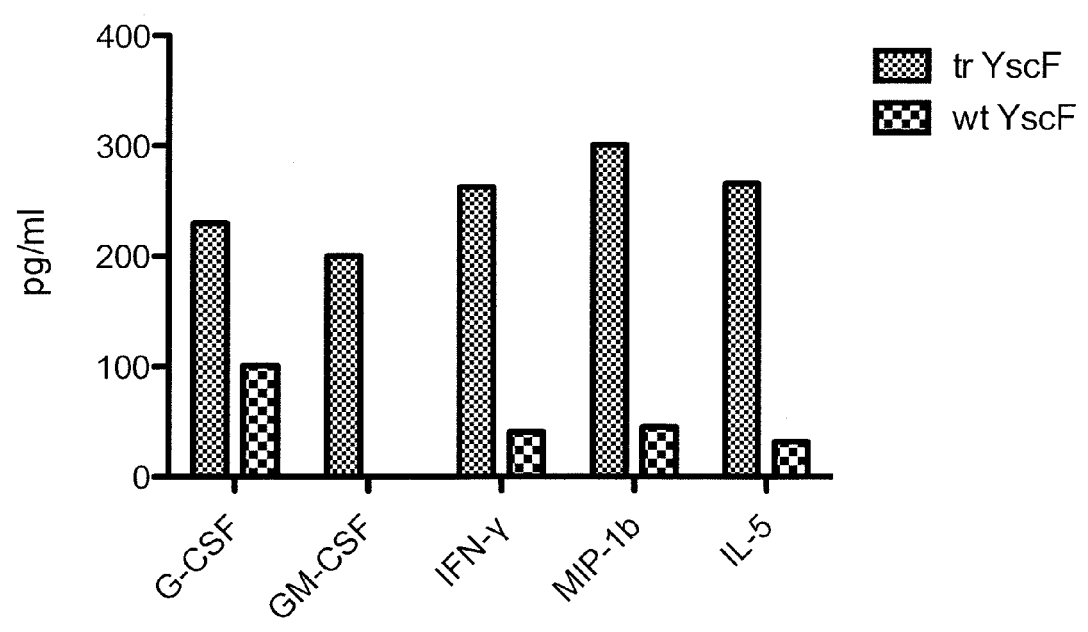
Figure 5:
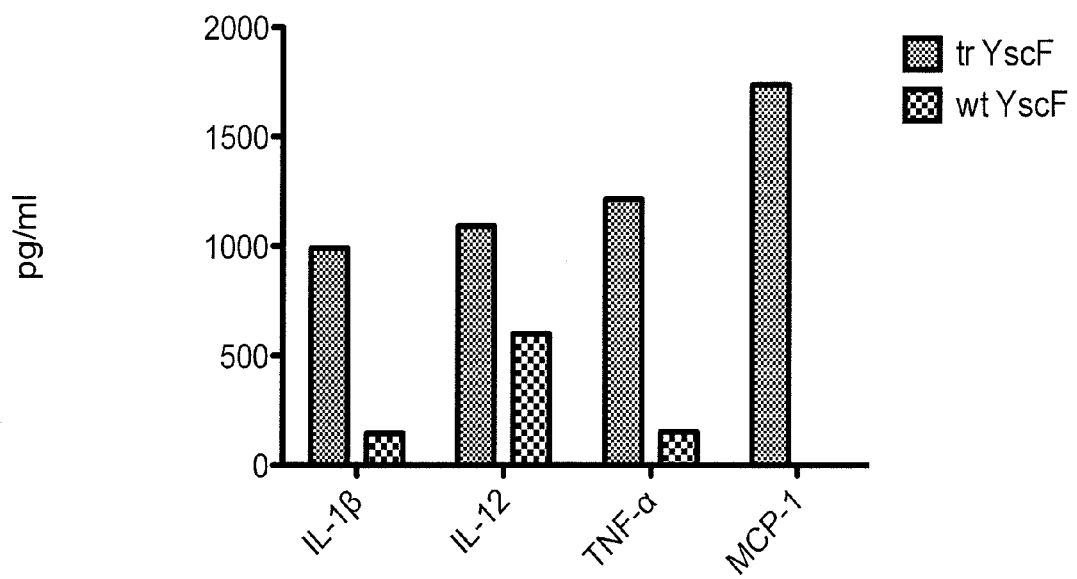
FIG. 5 is a histogram showing pooled mouse serum IL-1b, IL-12(p40), TNF-α and MCP-1 levels in mice vaccinated with YscF or trYscF.
Figure 6:
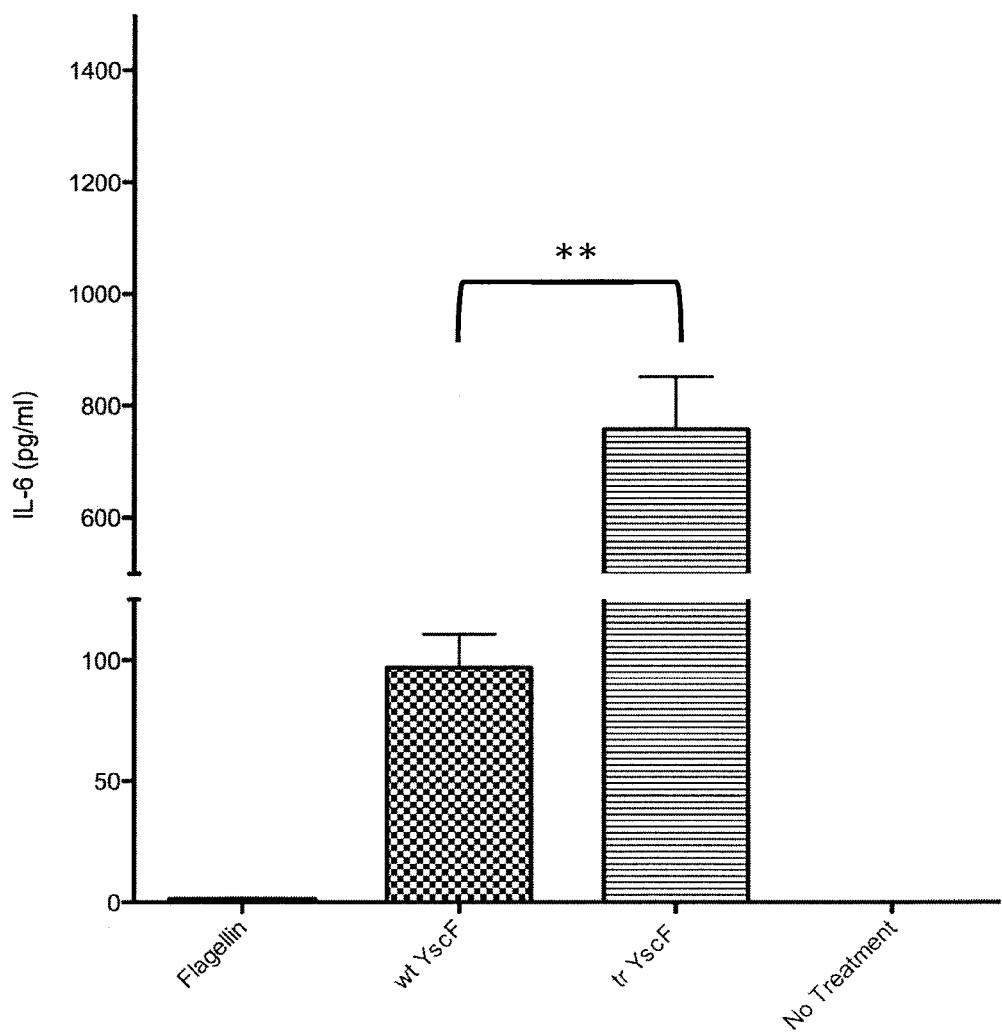
FIG. 6 is a histogram showing IL-6 levels in THP-1 cell supernatants of cells treated with YscF or trYscF.
Figure 7:
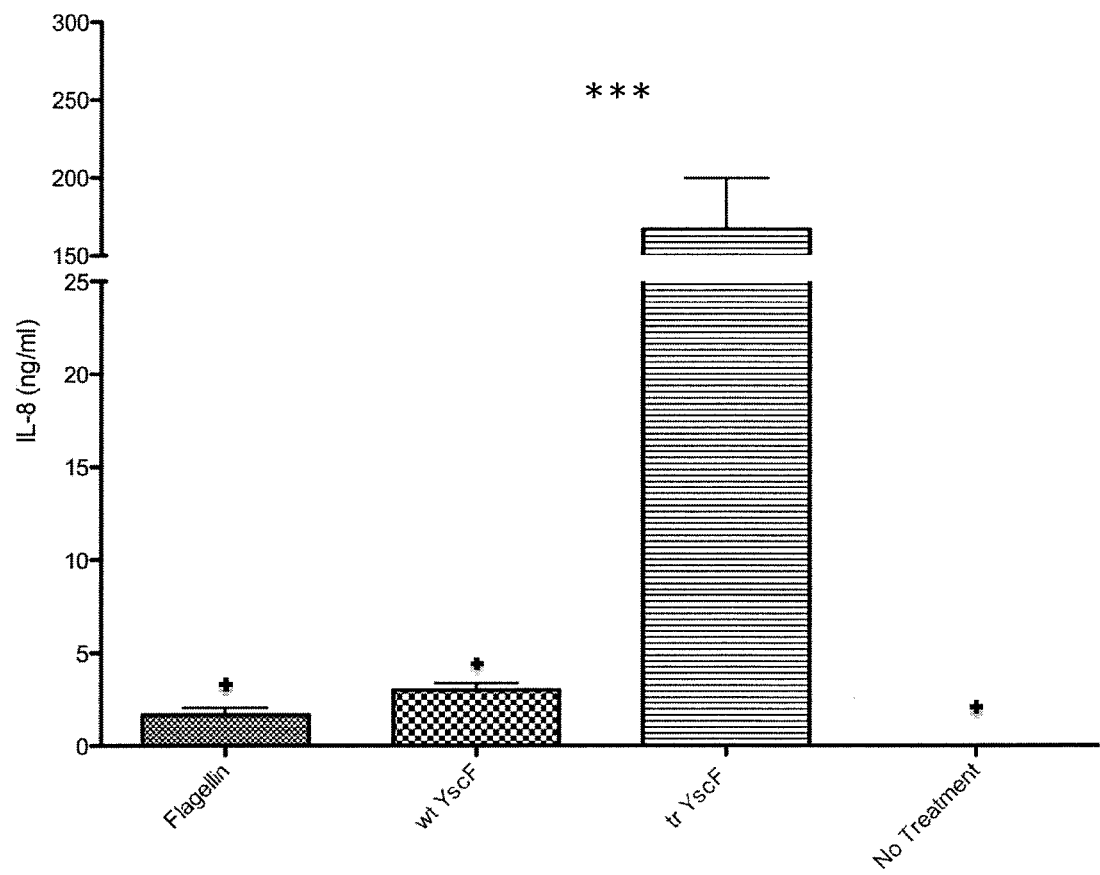
FIG. 7 is a histogram showing IL-8 levels in THP-1 cell supernatants of cells treated with YscF or trYscF.
Figure 8:
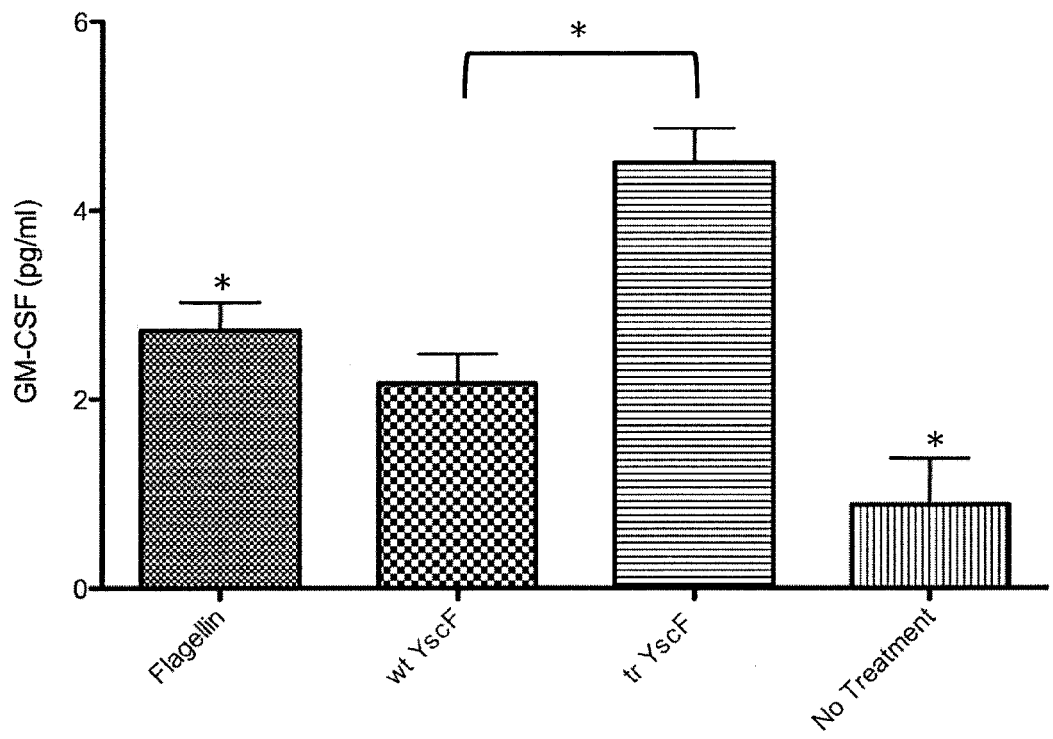
FIG. 8 is a histogram showing GM-CSF levels in THP-1 cell supernatants of cells treated with YscF or trYscF.
Figure 9:
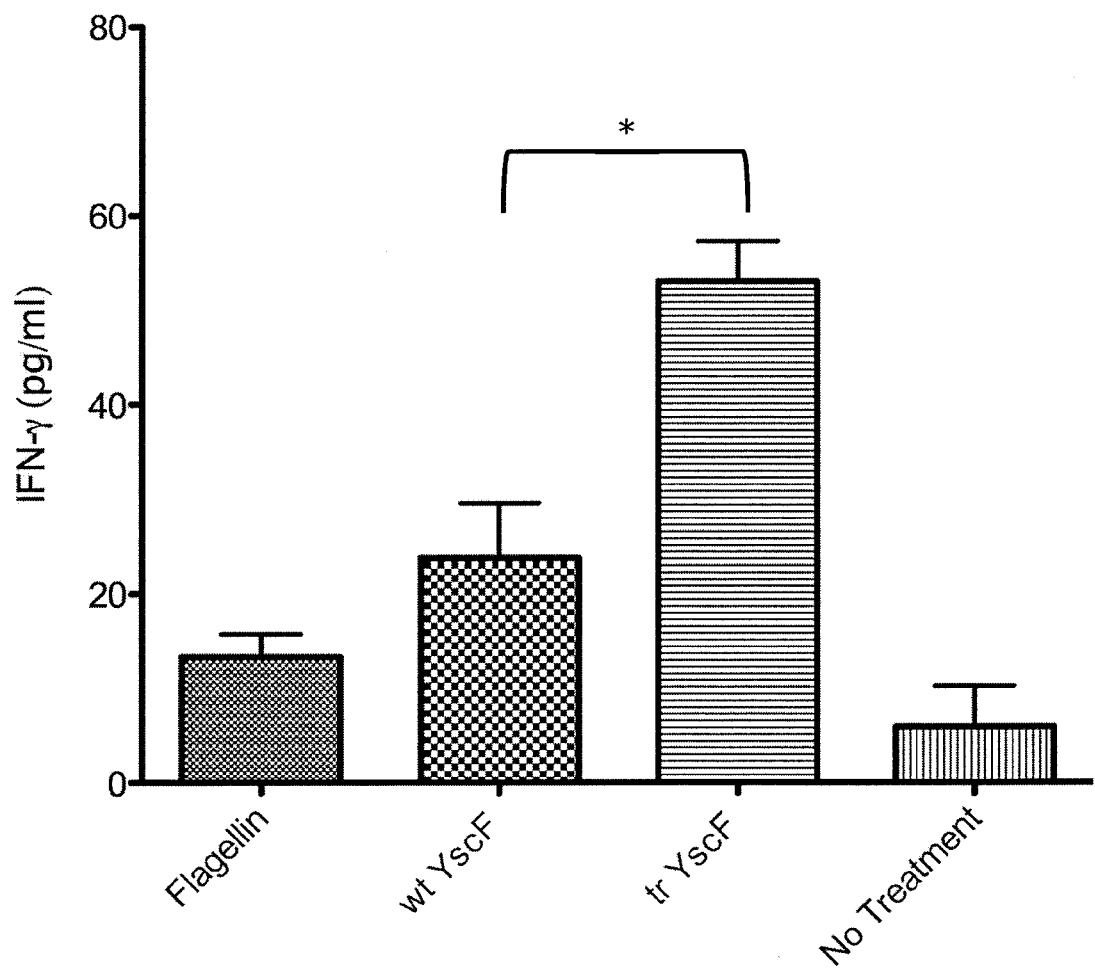
FIG. 9 is a histogram showing IFN-γ levels in THP-1 cell supernatants of cells treated with YscF or trYscF.
Figure 10:
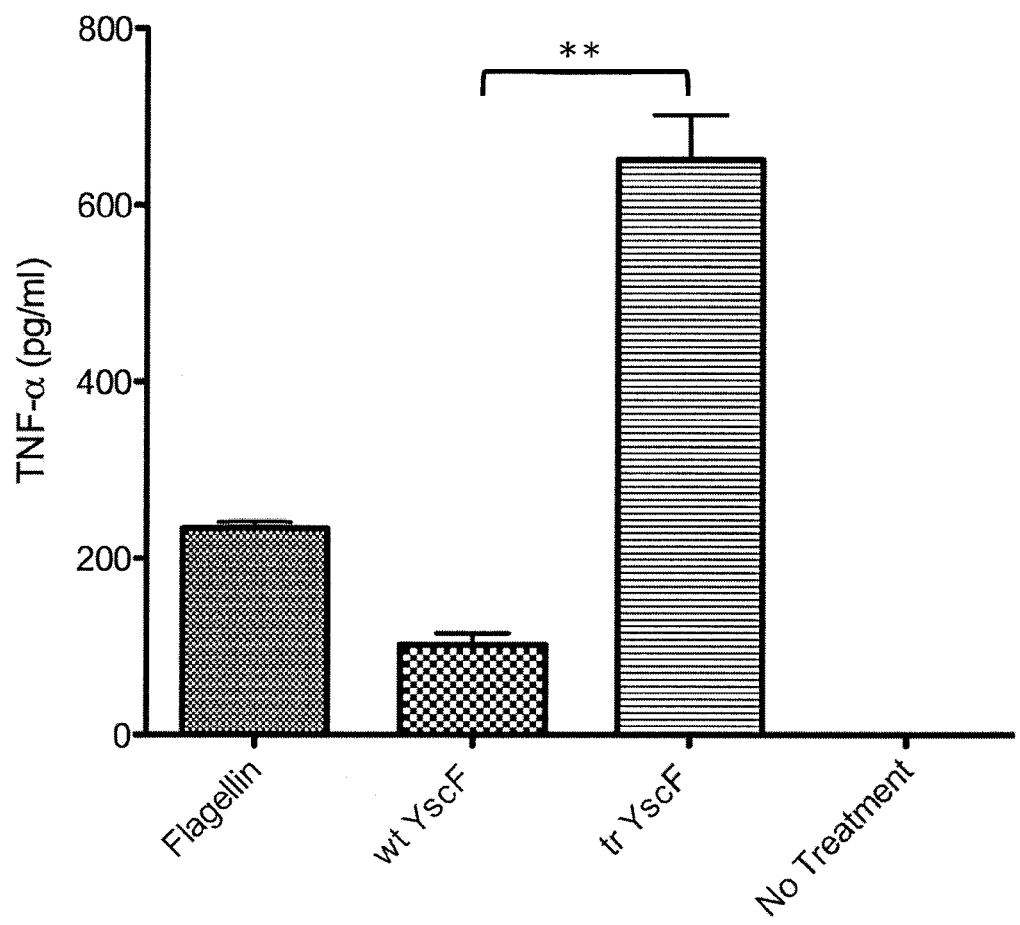
FIG. 10 is a histogram showing TNF-α levels in THP-1 cell supernatants of cells treated with YscF or trYscF.
Figure 11:
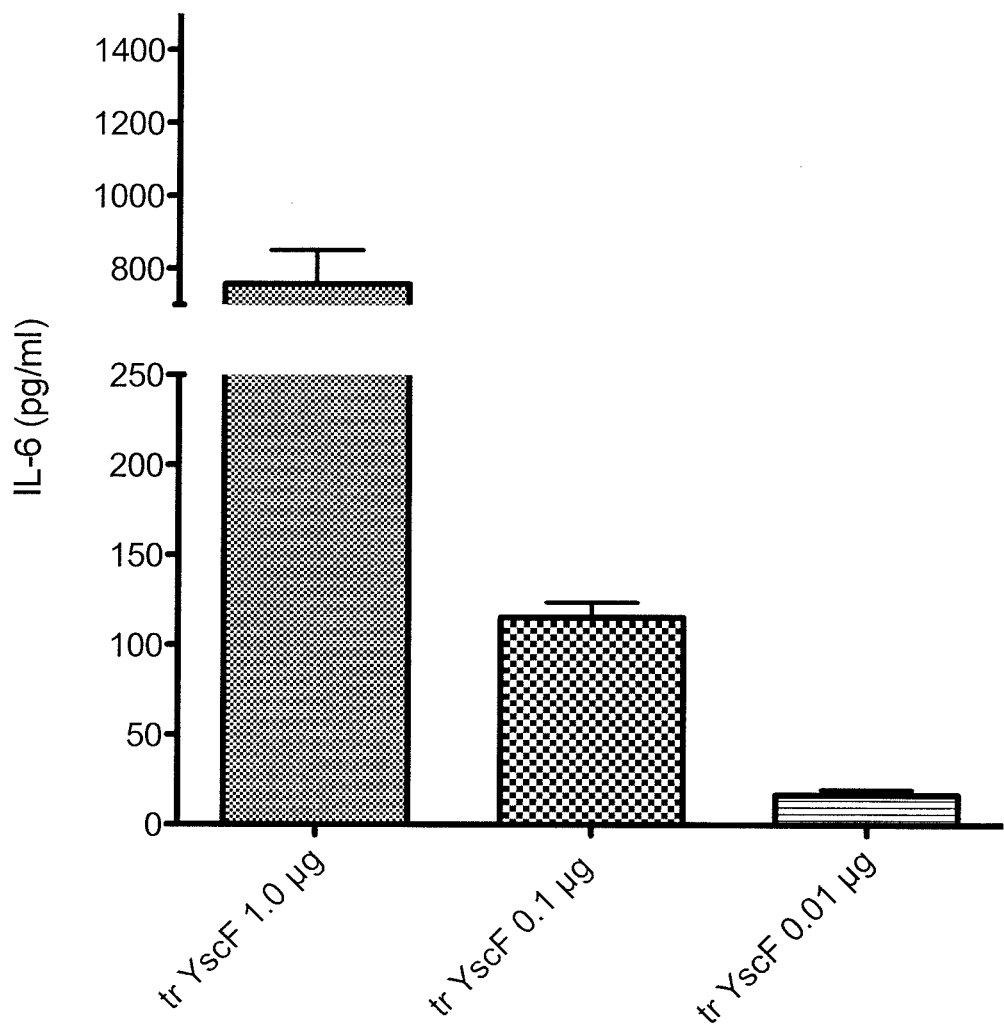
FIG. 11 is a histogram showing IL-6 levels in THP-1 cell supernatants of cells treated with varying doses of trYscF.
Figure 12:
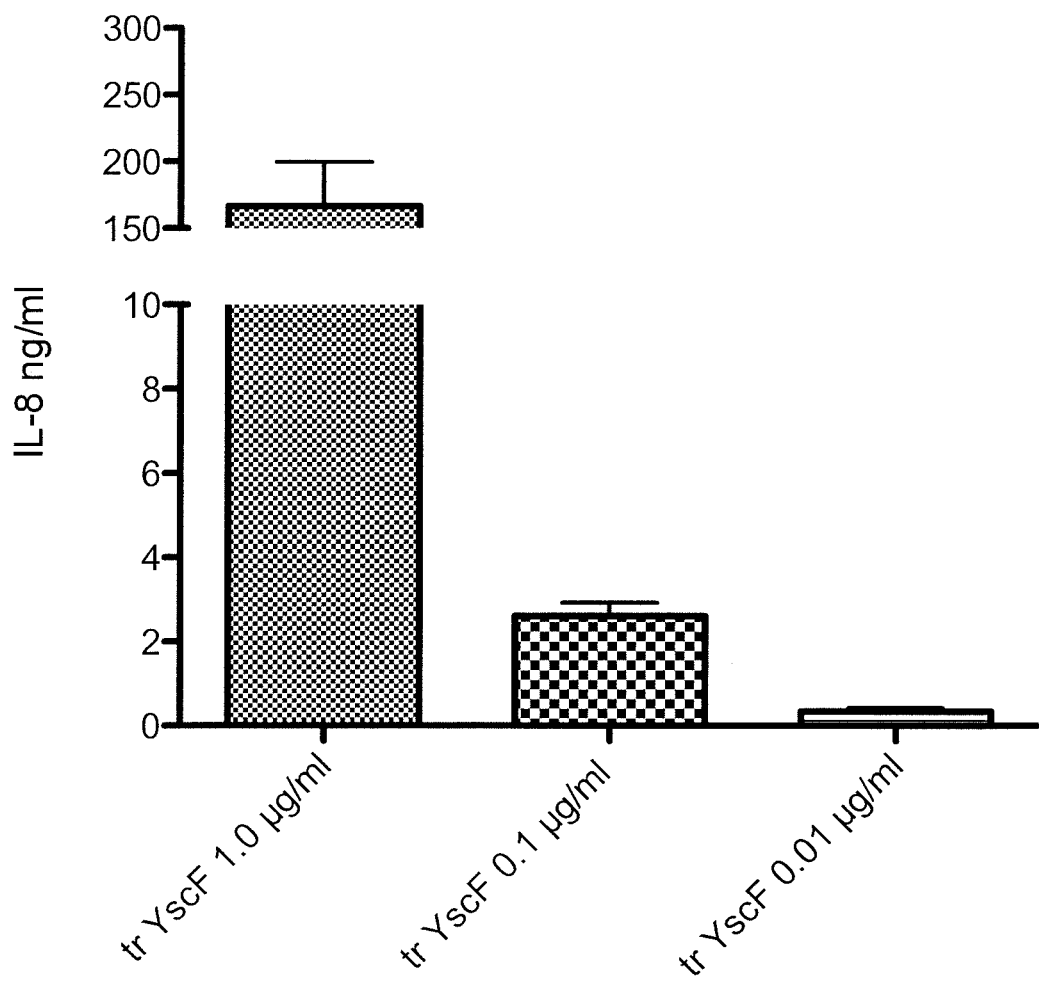
FIG. 12 is a histogram showing IL-8 levels in THP-1 cell supernatants of cells treated with varying doses of trYscF.
Figure 13:
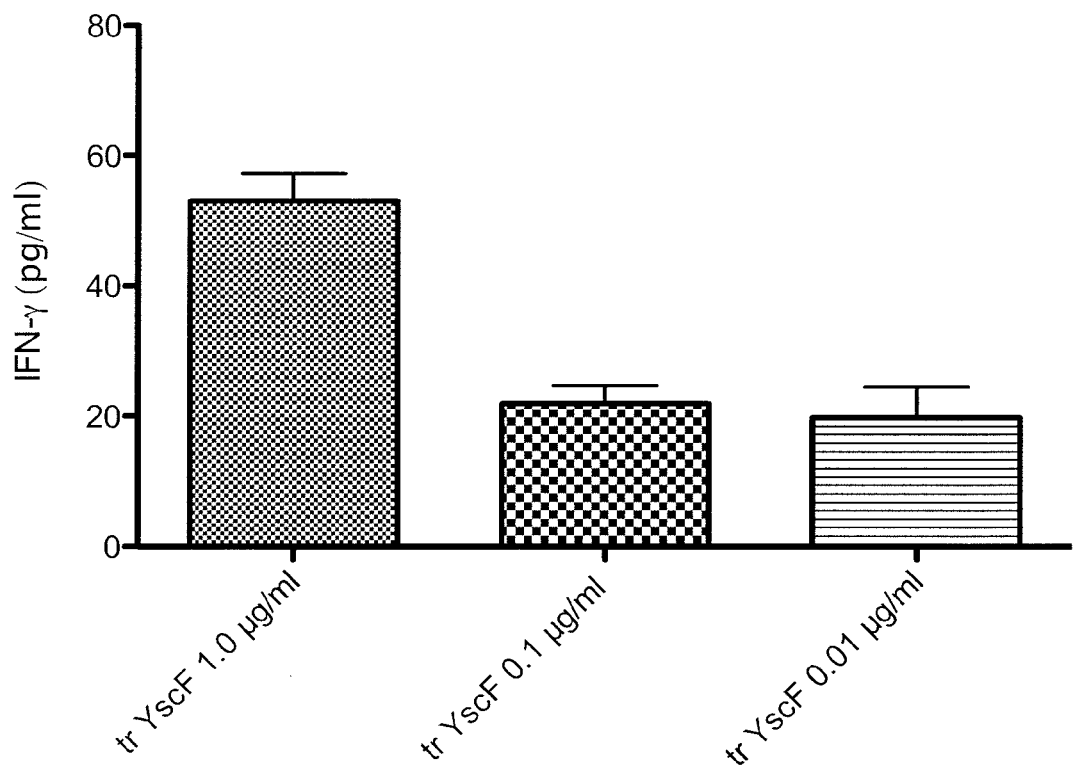
FIG. 13 is a histogram showing IFN-γ levels in THP-1 cell supernatants of cells treated with varying doses of trYscF.

The mouse survival results from immunization studies led to an investigation into the mechanism behind the lower mean time to death seen in trYscF treated mice. Serum samples were obtained two weeks post vaccination, pooled, and subsequently analyzed in order to study the cytokine profiles of immunized mice. See FIGS. 4 and 5. Proinflammatory cytokine levels, including IL-1β, IL-12, and TNF-α, were significantly higher in mice immunized with trYscF (SEQ ID NO:2) than mice immunized with wtYscF (SEQ ID NO:1). FIG. 5. Since there was a chance of contaminants, such as endotoxins, being present from the *E. coli* that was used to overexpress the protein, trYscF samples were tested for the presence of endotoxin. A limulus amebocyte lysate (LAL) assay of protein samples showed the amount of endotoxin in trYscF or YscF samples to be negligible. Specifically, trYscF samples were determined to have an endotoxin level of 0.06-0.125 EU/ml. Wild type YscF was determined to have an endotoxin level of 0.25-0.5 EU/ml. Therefore, not only were endotoxin levels far below the endotoxin limit, but the endotoxin level for wild type YscF samples was higher than found in trYscF samples. Furthermore, mice in all three groups (trYscF, YscF, and mock vaccinated) appeared healthy and active post-vaccination/pre-infection and there were no significant differences in average weight between the mouse groups. Examinations of coats, fur, skin, and nose coloration indicated that mice were equally healthy in all immunization groups. Mice ate normally and drank water regularly during this period. High levels of proinflammatory cytokines cannot be attributed to LPS contamination of vaccine samples.

Example 6

Antiserum from Mice Immunized with Truncated YscF Mapped to the Minor Surface Accessible Epitope In order to determine the specificity of antiserum from mice immunized with trYscF, pooled serum from mice immunized with trYscF (SEQ ID NO:2) was used to probe a PepSpot blot identical to those used for the original epitope mapping. Spots that were detected corresponded to the minor epitope found previously, which are predicted to be located in a surface accessible region. These results indicate that trYscF-specific antibodies were produced in immunized mice and that elimination of the major epitope does drive the immune response against the minor epitope.

Example 7

THP-1 Cells Treated with Truncated YscF Produce Significantly Higher Levels of Proinflammatory Cytokines Compared to Cells Treated with Wild Type YscF In order to obtain preliminary knowledge regarding the mechanism behind the elevated proinflammatory cytokine levels in serum from in vivo immunizations with trYscF, a human macrophage like immortal cell line was used for a stimulation assay. THP-1 cells were incubated for 24 h, in 96-well plates, with flagellin ((1 μg/ml); positive control), wild type YscF (1 μg/ml) (SEQ ID NO:1), trYscF (1 μg/ml, 0.1 μg/ml, and 0.01 μg/ml) (SEQ ID NO:2), or left untreated (negative control). Experiments were repeated three times and samples were taken from cell culture supernatants in triplicate. Dilutions of 1:10 were also made for trYscF samples. A BioPlex multiplex assay was run using samples from the cell stimulation experiments. Results indicated that cells stimulated with trYscF produce higher levels of IL-6, IL-8, IL-10, IFN-γ, GM-CSF and TNF-α compared to cells treated with wild type YscF, but treatment with trYscF did not trigger IL-2 or IL-4 release. See FIGS. 6-10. Furthermore, these cytokine levels were higher in cells treated with trYscF when compared to stimulation with the positive control, flagellin. Additionally, there was a dose-dependent response to trYscF observed for IL-6, IL-10, and TNF-α production for the concentrations used. See FIGS. 11-14. Adding lower concentrations of trYscF resulted in relatively lower production of IL-6, IL-10, and TNF-α. This, in part, indicates that trYscF is responsible for the observed increase in cytokine levels. These data suggest that YscF and trYscF induce cytokine production in macrophages. Interestingly, trYscF seems to be a more potent inducer than YscF. This result suggests that a sequence required for cytokine induction is blocked by the N-terminus of YscF, or that the N-terminus of YscF has a negative effect on the interaction of YscF with a putative cellular receptor. These results also suggest that pathogen recognition receptors may be involved in cytokine induction.

In addition, treatment of human THP-1 macrophage cells with wild type YscF and trYscF induced the NF-κB pathway. TrYscF stimulated macrophages, activating the NF-κB pathway and subsequent production of proinflammatory cytokines. Although the levels of cytokine production were different in most cases between cells treated with wtYscF versus cells treated with trYscF, immunoblot analysis of cell lysates do not necessarily indicate that there is a difference between levels of NF-κB activation between wtYscF and trYscF stimulation.

Example 8

Figure 15:
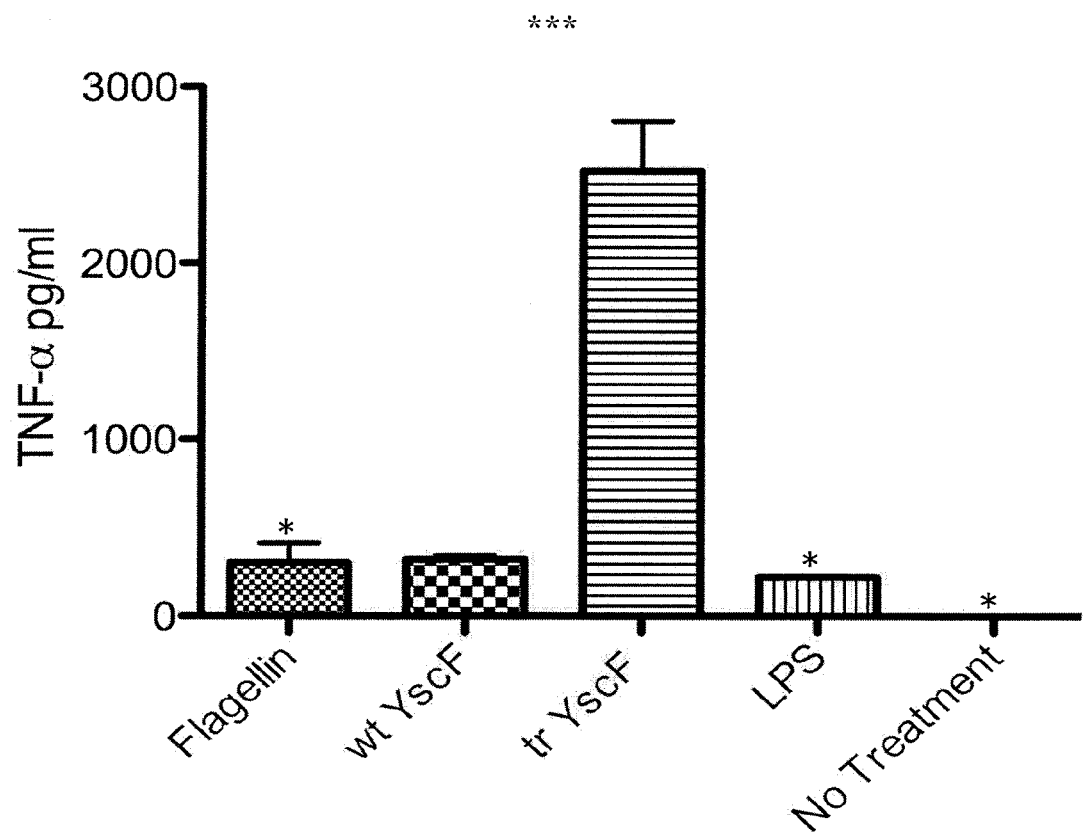
FIG. 15 is a histogram showing TNF-α levels in supernatant samples from primary mouse macrophage cells treated with YscF or trYscF

Mouse Primary Peritoneal Macrophage Cells Treated with Truncated YscF and Wild Type YscF Primary mouse macrophage peritoneal cells were isolated from C57BL/6N mice from a peritoneal lavage. These macrophage cells were immediately seeded into a 96-well plate at a concentration of $8 \times 10^5$ cells/ml. Cells were incubated with 1 μg/ml of flagellin, wild type YscF (SEQ ID NO:1), trYscF (SEQ ID NO:2), LPS, or left untreated. See FIG. 15. After 24 hours, supernatants were removed from cell samples. Results from a mouse TNF-α ELISA of supernatants show that incubating primary mouse macrophages with either YscF or trYscF results in production of TNF-α, confirming induction of TNF-α in an ex vivo situation. FIG. 15. TNF-α production was significantly higher with trYscF treatment than with wtYscF. Furthermore, NF-κB was found to be activated in cells treated with trYscF or YscF.

Example 9

Human TNF-α ELISA on THP-1 Cell Supernatants

Figure 16:
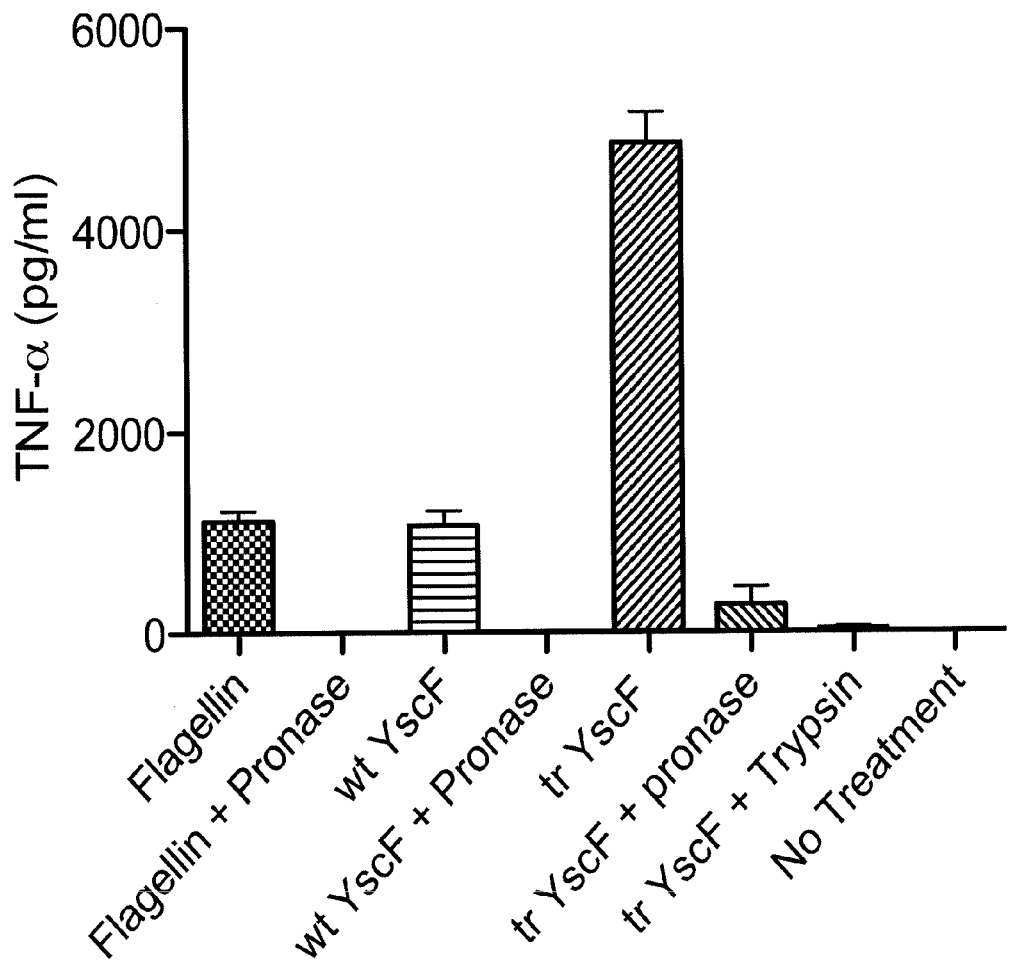
FIG. 16 is a histogram showing TNF-α levels in THP-1 cell supernatants, following treatment with digested protein.

Since induction of TNF-α from THP-1 by YscF and trYscF was found to be robust in the BioPlex study, and since production of TNF-α was observed in a dose-dependent manner (i.e., eliminating the presence of the protein resulted in loss of TNF-α production), TNF-α production was used to further investigate trYscF stimulation activity. Flagellin, wild type YscF (SEQ ID NO:1), trYscF (SEQ ID NO:2), and LPS were treated with proteases to demonstrate that the presence of intact protein was required for the production of proinflammatory cytokines by THP-1 cells. Protein samples (YscF, trYscF and Flagellin) were treated with pronase or trypsin. Protease-treated and untreated samples were used to stimulate THP-1 cells. THP-1 cells were seeded in a 96-well plate at $8 \times 10^5$ cells/ml, as done for the BioPlex assay. Protein samples were prepared and used at 1 μg/ml. Cells were then incubated for 24 h after addition of protein and the supernatants were removed and used to measure TNF-α production by ELISA. The same pattern of TNF-α production was observed as seen in the BioPlex assays. FIG. 16. Differences in concentration between BioPlex assays and ELISAs were expected, since the TNF-α concentration was determined using a different methodology. However, the same pattern of TNF-α production was seen in cells treated with YscF and trYscF. FIG. 16. Treatment with YscF resulted in a significantly lower concentration of TNF-α than trYscF (987 pg/ml versus 4328 pg/ml respectively). As seen previously, treatment of THP-1 cells with a positive control for TLR stimulation, flagellin, resulted in lower production of TNF-α than trYscF, as well. Furthermore, treatment of protein samples with proteases resulted in either diminished or considerably decreased amounts of TNF-α production. See FIG. 16. There was also a significant difference in TNF-α levels between all protein treatments and digested protein counterparts (P<0.001). Taken together, these results indicate that trYscF and YscF activate THP-1 cells to produce TNF-α. Furthermore, the observed stimulation of macrophages and production of TNF-α can conclusively be attributed to the presence of protein in the samples, since degrading the protein results in reduced to virtually no production of TNF-α.

Example 10

Mouse Anti-Truncated YscF Antibody and Yops Translocation

As previously noted, vaccination of C57BL/6N mice with trYscF alone did not provide protection from challenge with *Y. pestis*. However, analysis of serum from mice immunized with trYscF showed that mice developed an antibody response to trYscF. See Example 4. Furthermore, the antibody response was directed towards the minor epitope on YscF. See Examples 4 and 6. This would suggest that antibody against trYscF would be able to recognize and bind to YscF subunits in a fully polymerized needle. Although trYscF immunization did not offer protection against plague, in vivo, experiments were conducted to determine if antibody against trYscF could neutralize the T3SS needle in vitro. One way to examine this is by conducting a translocation assay using eukaryotic cells as a target for *Y. pestis* Yops translocation. Previous studies have shown that antibodies to wild type YscF are not capable of neutralizing the YscF needle complex, demonstrated by a failure to prevent translocation of Yops (Matson et al., 2005).

Figure 18:
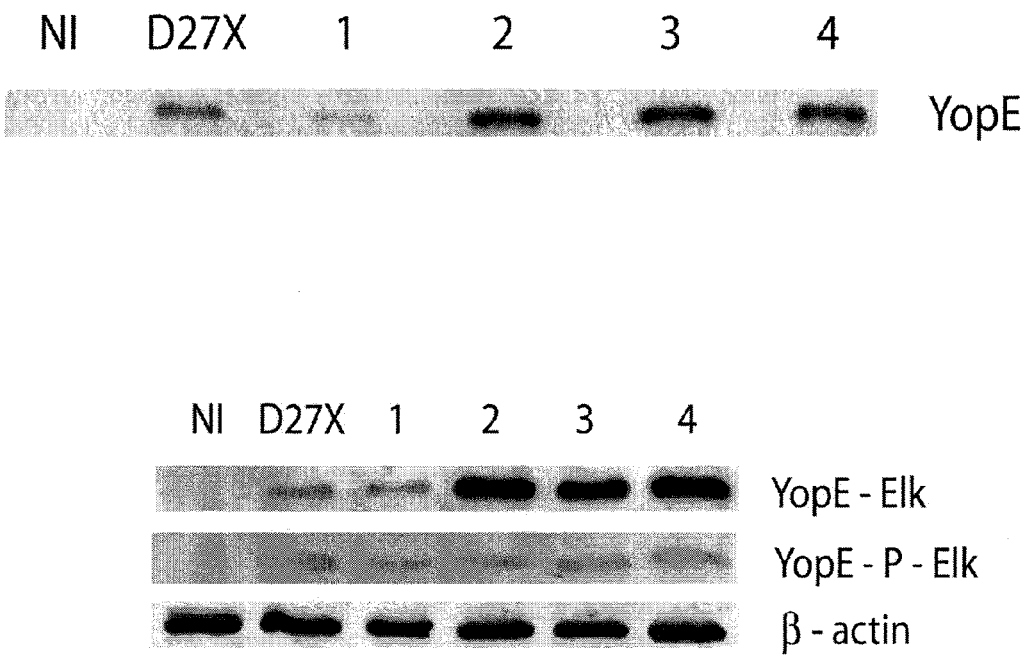
FIG. 18 is an immunoblot of HeLa cell lysates showing the effect of neutralizing antibodies against YscF or trYscF on YopE translocation. Blots were probed with anti-YopE antibody in order to detect Yops translocation into HeLa cells. Blot order: NI (not infected), D27X, column 1 (D27X+1:10 mouse-anti-trYscF), column 2 (D27X+1:25 mouse-anti-trYscF), column 3 (D27X+1:50 mouse-anti-trYscF), and column 4 (D27X+1:100 mouse-anti-trYscF).
Figure 19:
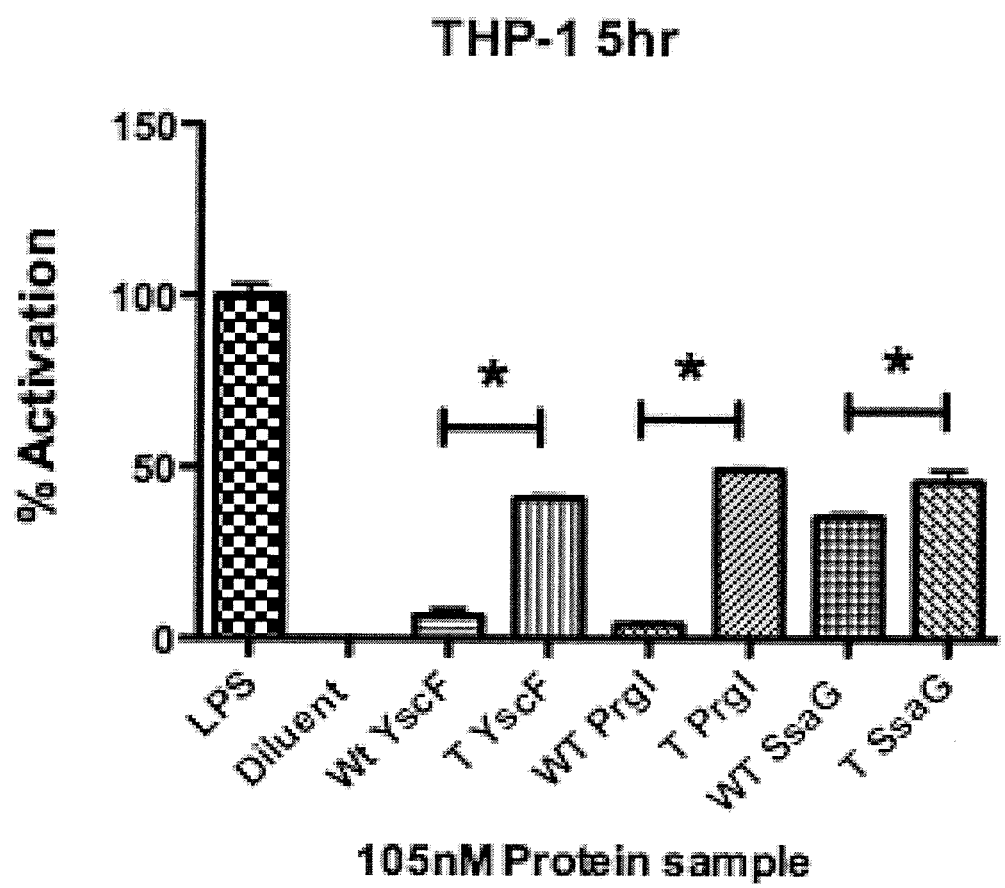
FIG. 19 is a histogram showing induction of TNF-α by trYscF, trPrgI, and trSsaG, in non-activated THP-1 monocytes.
Figure 20:
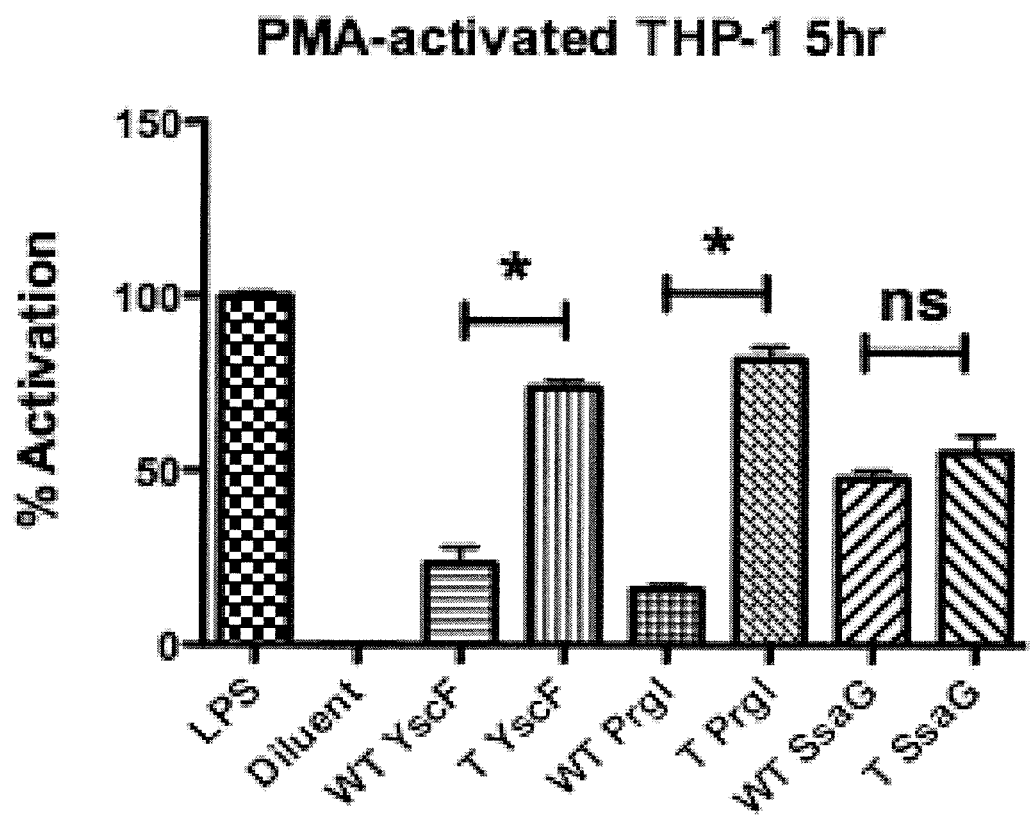
FIG. 20 is a histogram showing induction of TNF-α by trYscF, trPrgI, and trSsaG, in activated THP-1 macrophages.
Figure 21:
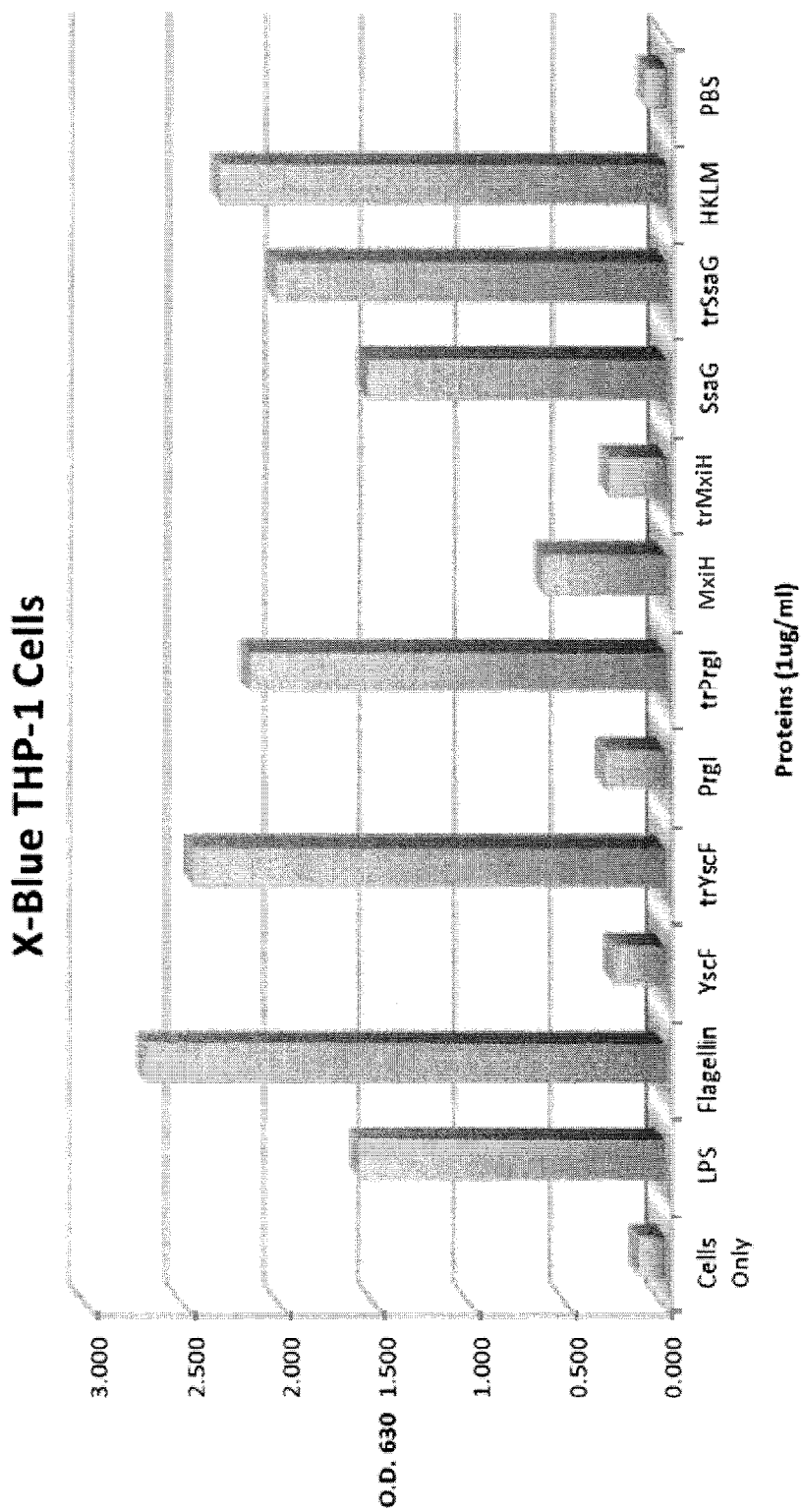
FIG. 21 is a histogram showing induction of SEAP reporter gene expression in THP-1 cells using full length and truncated YscF, PrgI, MxiH, and SsaG proteins in the presence of MyD88.
Figure 22:
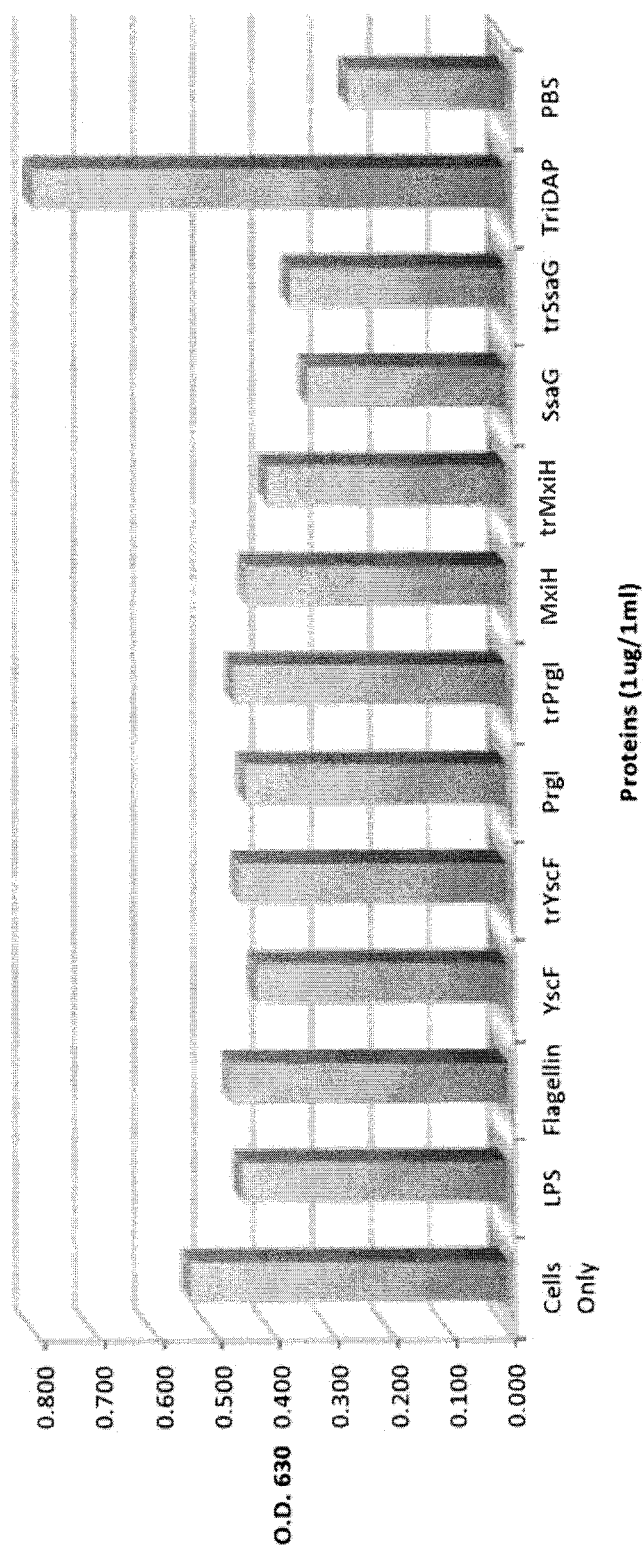
FIG. 22 is a histogram showing induction of SEAP reporter gene expression in THP-1 cells using full length and truncated YscF, PrgI, MxiH, and SsaG proteins in the absence of MyD88.

HeLa cells were infected in the presence or absence of anti-trYscF mouse sera. Mouse sera were diluted to 1:10, 1:25, 1:50 and 1:100 for this study. HeLa cells were incubated with *Y. pestis* containing pYopE-Elk1 at an MOI of 30 in the presence or absence of anti-trYscF antibody. After four hours, cells were observed under a phase contrast microscope for cytotoxicity ("cell rounding"), which is indicative of Yops translocation. Neutralizing antibody can potentially prevent translocation of Yops and therefore, cell rounding. Uninfected cells did not round up after four hours, while the positive control for translocation (*Y. pestis* in the absence of anti-trYscF mouse sera) resulted in cell rounding of most cells. Although cell rounding was prevalent in HeLa cells treated with 1:25 dilution and higher of mouse sera, treatment with a 1:10 dilution of mouse sera resulted in lower observed cell cytotoxicity. Further, HeLa cells were lysed and cell lysates were loaded onto an SDS-PAGE gel and immunoblotted. FIG. 18. Blots were probed with anti-YopE antibody in order to detect Yops translocation into HeLa cells. Blot order: NI (not infected), D27X, 1 (D27X+1:10 mouse-anti-trYscF), 2 (D27X+1:25 mouse-anti-trYscF), 3 (D27X+1:50 mouse-anti-trYscF), 4 (D27X+1:100 mouse-anti-trYscF). As expected, uninfected cells did not show a band for YopE in immunoblots. See FIG. 18. The positive control for Yops translocation, cell lysates from HeLa cells infected with *Y. pestis* alone, resulted in a clear band for YopE. Cell lysates from HeLa cells infected with *Y. pestis* and dilutions of mouse anti-trYscF sera 1:25 and higher also showed the presence of YopE in cell lysate samples. However, cell lysates from HeLa cells infected with *Y. pestis* in the presence of a 1:10 dilution of mouse anti-trYscF sera showed decreased YopE levels in the infected HeLa cells.

Translocation of YopE was also analyzed by probing blots with anti-Elk1 and anti phospho-Elk1 rabbit antibodies. FIG. 18 (lower panel). Technically, Elk1 is only phosphorylated once inside a eukaryotic cell; therefore, the YopE-Elk1 construct would only be expected to be phosphorylated after translocation of YopE into HeLa cells. Interestingly, based on results from Elk1 and phospho-Elk1 immunoblots, at serum dilutions of 1:25 and higher, YopE levels were higher than in lysates of cells infected with *Y. pestis* in the absence of anti-trYscF serum. Furthermore, actin loading control immunoblots show equivalent amounts of samples were loaded in gels. Immunoblots of lysate samples probed with antibody against phospho-Elk1 show limited levels of YopE translocation in instances where serum antibody was absent or at a very low dilution (1:10), compared to bands corresponding to lysate samples from cells treated with 1:25 and higher dilutions of anti-trYscF serum. Taken together, these results suggest that, at high concentrations (for example, a 1:10 dilution), mouse anti-trYscF sera may be able to partially neutralize the type III secretion needle, resulting in either decreased YopE expression or secretion and possibly decreased translocation of Yops. That is, decreased YopE expression is suggestive of a Yops secretion or translocation defect, as Yops expression is linked to secretion. Furthermore, this partial neutralization by anti-trYscF antibody is not seen in connection with higher dilutions of sera. In fact, results suggest that lower concentrations of anti-trYscF antibody may in fact be stimulating secretion and/or translocation of YopE in vitro.

Example 11

Truncated YscF and the NFκ-B Pathway

Figure 17:
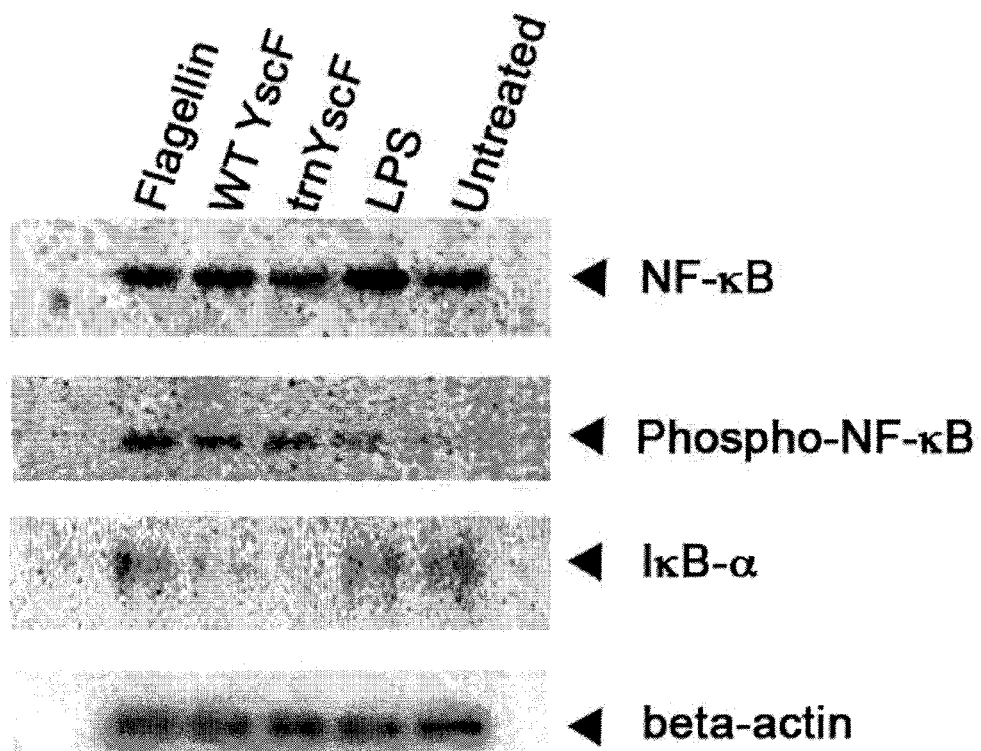
FIG. 17 is a Western blot analysis showing NF-κB activation in THP-1 cells treated with YscF or trYscF.

It has been observed that trYscF induces robust proinflammatory cytokine expression in vivo in mouse immunization models, in vitro in a THP-1 human macrophages, and ex vivo in mouse primary peritoneal macrophage cells. One mechanism that trYscF could be exploiting to stimulate proinflammatory cytokine expression by macrophages is activation of the NF-κB pathway. Evidence of the NF-κB pathway being involved in production of proinflammatory cytokines could possibly associate trYscF stimulation with that of TLR stimulation. In the next set of experiments, THP-1 human macrophage cells were treated with flagellin, wild type YscF (SEQ ID NO:1), trYscF (SEQ ID NO:2), LPS, or no treatment, in 6-well plates. See FIG. 17. After a 24 h incubation, THP-1 cells were lysed. Cell lysates were loaded onto 12% SDS-PAGE gels, and protein constituents were separated by electrophoresis. Proteins were transferred onto Immobilon-P membranes in Tris-Glycine transfer buffer. Blots were probed with antibody against a number of NF-κB pathway mediators including rabbit anti-NF-κB p65, rabbit anti-phospho-NF-κB, rabbit anti-IκBα, rabbit anti-phospho-IκBα, and mouse-anti-β-actin. Blots were then probed with the appropriate secondary antibody; specifically, goat anti-rabbit or anti-mouse conjugated to HRP. Immunoblots were developed for chemiluminesence and signals were collected with the Typhoon™ imaging system. Blots probed with anti-phospho-IκBα antibody did not show any bands. FIG. 17. In vitro, most phosphorylated IκBα is almost completely degraded approximately 15-30 minutes after being phosphorylated (Mathes et al., 2008). Cells treated with flagellin, wtYscF, or trYscF showed lower amounts of IκBα in cell lysate samples, compared to untreated THP-1 cell lysates. See FIG. 17. This indicates that these cells were induced, leading to higher amounts of NF-κB activation, since IκBα is an inhibitor of NE-κB and, once phosphorylated, is degraded, leaving NE-κB free to be phosphorylated, activated, and translocated into the nucleus to induce expression of multiple cytokines and chemokines. Immunoblots indicate that treated and untreated cells contained similar levels of total NF-κB (non-phosphorylated and phosphorylated NE-κB). These bands correspond to both activated and non-activated NF-κB.

It was expected that total levels of NE-κB would be similar in all cell lysates. Interestingly, the Phospho-NF-κB levels appear to be higher in cell lysates from cells treated with flagellin, wtYscF and trYscF, compared to non-treated cells. Phosphorylated NF-κB suggests that the NE-κB pathway is activated. Like the positive control for TLR stimulation, flagellin, the data suggests that wtYscF and trYscF are also stimulating a TLR. Analysis of the NF-κB pathway demonstrates that trYscF and YscF induce the NF-κB pathway. This suggests that a TLR-mediated pathway may be activated when trYscF and YscF come into contact with eukaryotic cells in vitro.

Example 12

Examining the Adjuvant Properties of YscF

Mice were vaccinated to evaluate the ability of YscF (SEQ ID NO:1) or trYscF (SEQ ID NO:2) to induce heterologous protection. The well-characterized protective antigen LcrV from *Yersinia pestis* was used, and vaccinated mice were subsequently challenged with *Y. pestis*. Previously, doses up to $5 \times 10^4$ were used, with no evidence of increased protection using combined LcrV and YscF or trYscF. C57BL/6 mice and BALB/c mice were vaccinated with trYscF, wtYscF, V/trYscF, V/wtYscF. Plasmids pJM119 (encoding YscF), pMNT67 (encoding trYscF), and pMH73 (encoding LcrV) were used to overexpress proteins in *E. coli* line BL21 (DE3). Protein expression was induced, and bacteria were lysed for protein purification. His-tagged metal affinity purification (Talon resin, Clontech was used) of YscF, trYscF, and LcrV, and proteins were quantified using BCA assay. Either Freunds complete (CFA; controls), or Freund's incomplete (IFA; vehicle for testing activity) adjuvant was used for vaccinations. Mice were vaccinated, with primary vaccinations containing 40 ug of each recombinant protein. Booster vaccinations contained 20 ug of each protein. Vaccinated mice were challenged with the following doses of *Y. pestis* KIM5 i.v. The vaccination prot TABLE 1b SEAP reporter expression in HEK293 cells (expressing various human TLRs) using YscF and trYscF, screening 2.

| 293 Cell Line | No Sample | Sample 1 | Sample 2 | +Control |
|---|---|---|---|---|
| hTLR2 | 0.116 | 0.272 | 1.981 | 2.248 |
| hTLR3 | 0.106 | 0.093 | 0.101 | 2.502 |
| hTLR4 (MD2-CD14) | 0.164 | 0.861 | 1.904 | 2.136 |
| hTLR5 | 0.148 | 0.139 | 0.154 | 2.373 |
| hTLR7 | 0.103 | 0.094 | 0.097 | 2.381 |
| hTLR8 | 0.108 | 0.095 | 0.105 | 2.395 |
| hTLR9 | 0.090 | 0.074 | 0.079 | 1.962 |
| NF-κB Control Cells | 0.098 | 0.095 | 0.093 | 2.318 |

Figure 23:
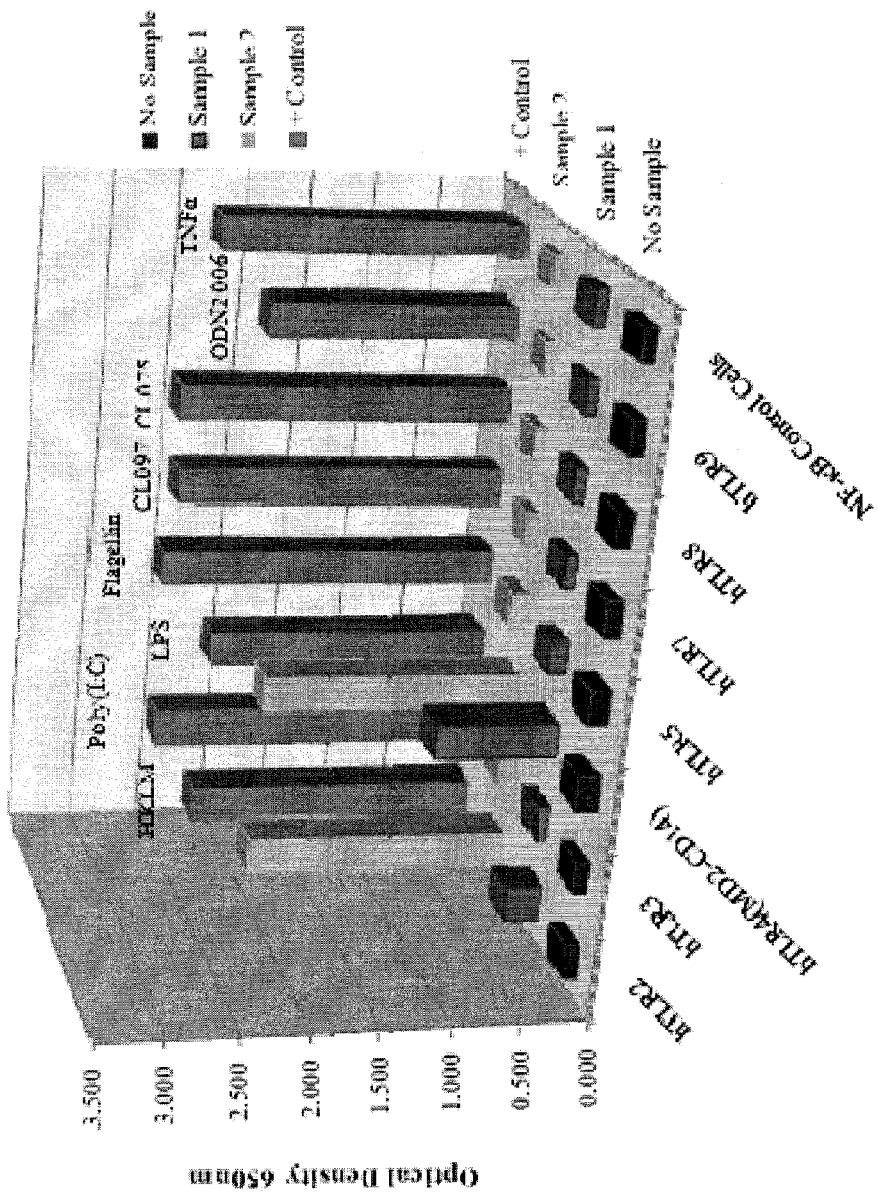
FIG. 23 is a histogram showing induction of SEAP reporter gene expression by YscF and trYscF in HEK293 cells engineered for expression of various TLRs.

FIG. 23 is a histogram illustrating data obtained from screenings 1 and 2 (averaged). YscF and trYscF induced SEAP expression in cell lines expressing either TLR2 (TLR1 and TLR6 are also expressed in this line) or TLR4. Induction in the presence of neutralizing antibody against either TLR1 or TLR6 suggests that YscF/trYscF are sensed by TLR2 and TLR6. These results demonstrate that T3S needle proteins may be sensed by TLR2, likely in conjunction with TLR6, to induce a MyD88 pathway, resulting in pro-inflammatory cytokine expression.

Example 16

Evaluating N-Terminal Deletion Fragments of YscF

Figure 24:
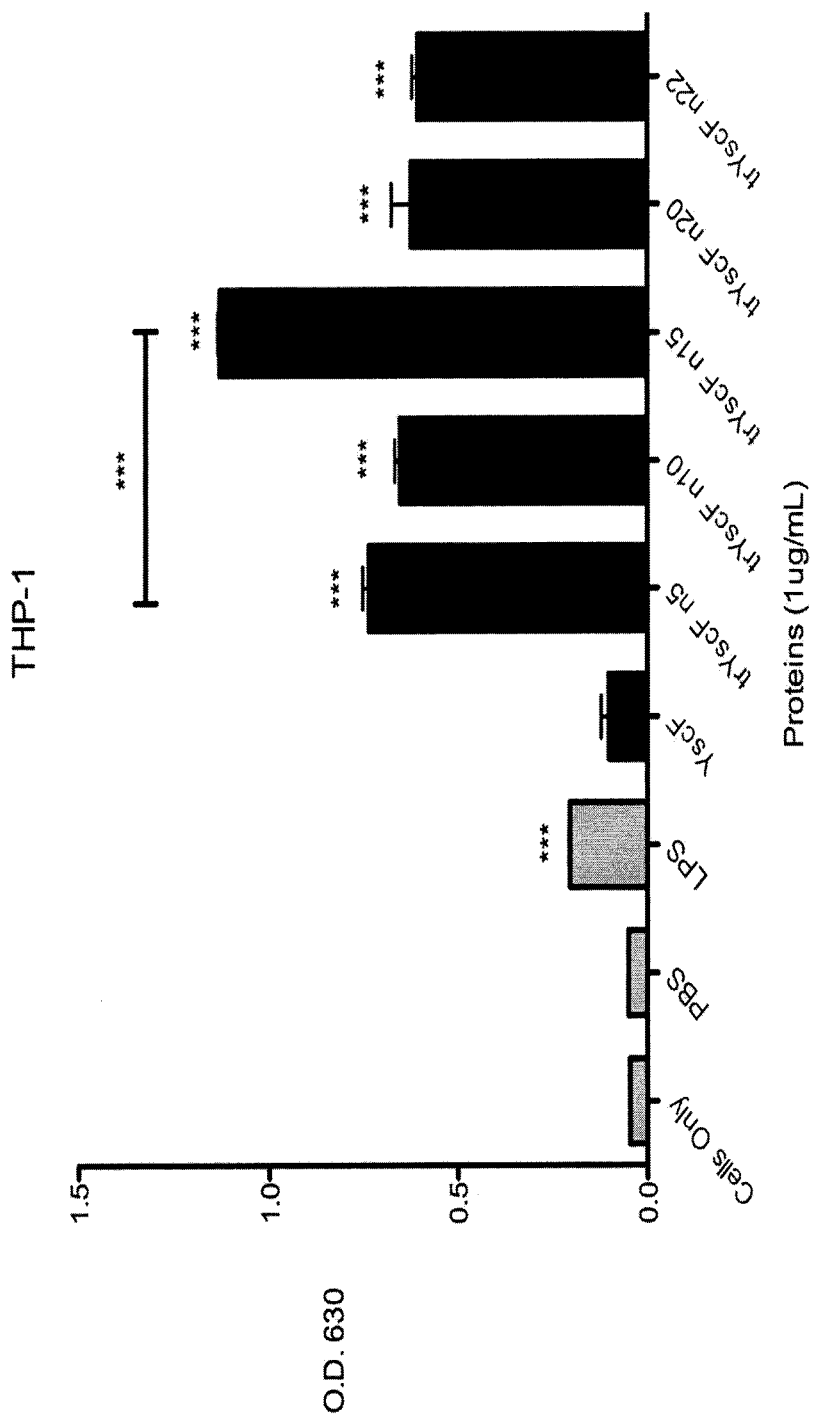
FIG. 24 is a histogram showing induction of SEAP reporter gene expression in THP-1 cells using YscF, and N-terminal deletion fragments, with MyD88 present.
Figure 25:
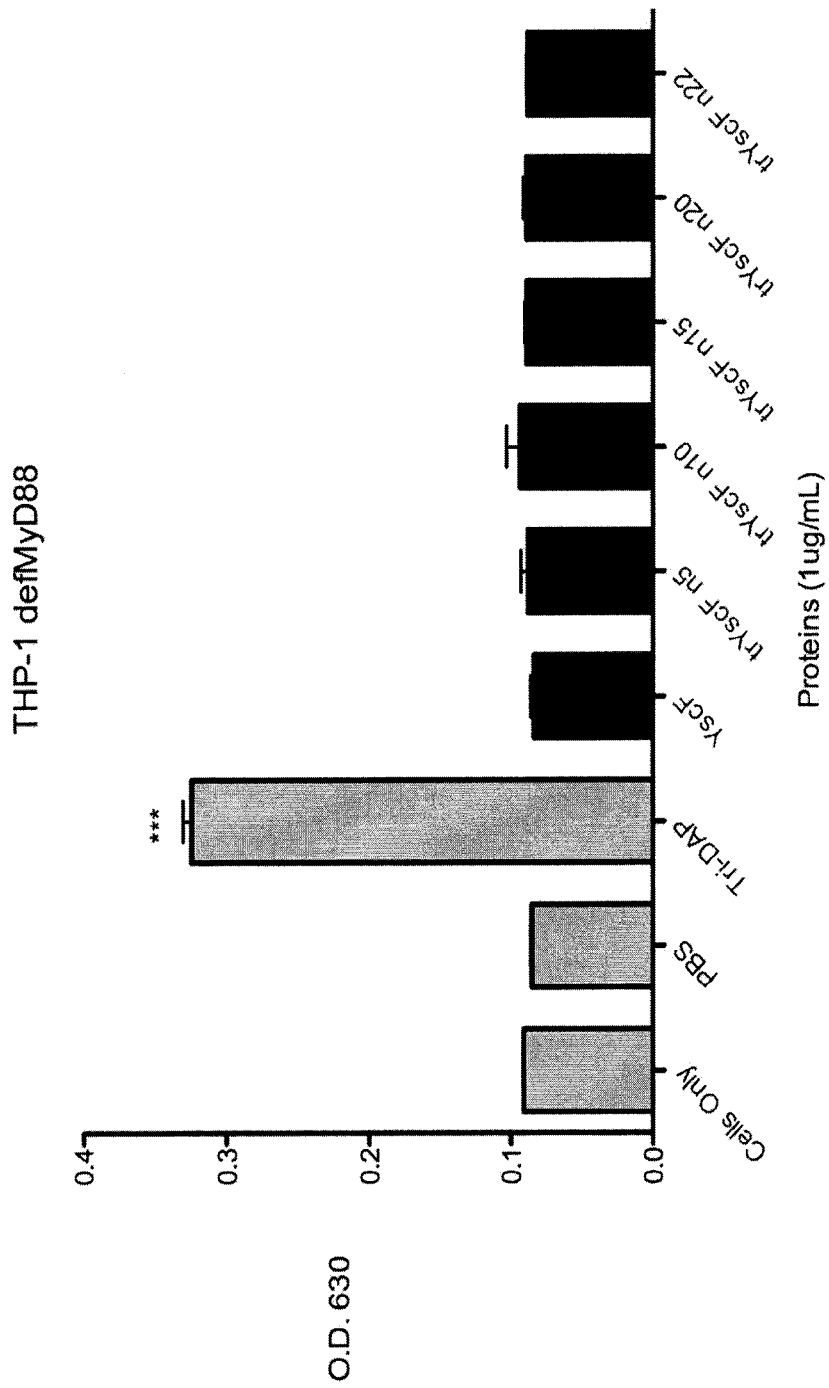
FIG. 25 is a histogram showing induction of SEAP reporter gene expression in THP-1 cells using YscF and N-terminal deletion fragments, in the absence of MyD88.

Various N-terminal YscF deletion fragments were evaluated for their ability to activate the NF-κB pathway in cell lysates of human macrophage (THP-1) cells. Proteins analyzed included YscF (SEQ ID NO:1), the 22-amino acid N-terminal deletion trYscF (trYscF n22) (SEQ ID NO:2), and YscF fragments lacking the first N-terminal 5 (SEQ ID NO:27), 10 (SEQ ID NO:28), 15 (SEQ ID NO:29), or 20 (SEQ ID NO:30) amino acids of YscF (SEQ ID NO:1). See FIGS. 24 and 25. THP-1 XBlue cells containing an AP-1 and MyD88-responsive secreted embryonic alkaline phosphatase (SEAP) reporter gene were used with an LPS, PBS, and cells-only control. See FIG. 25. Additionally, THP-1 cells lacking MyD88 were used to assess MyD88 dependence of SEAP induction, with TriDAP as a positive control for AP-1 (inflammasome) induction. FIG. 25. All constructs were His-tagged.

THP1 Xblue cells responded significantly to all tested N-terminal truncations of YscF. An N-terminal deletion fragment of 15 amino acids (trYscF n15) produced a significantly higher response than the other fragments. See FIG. 24. Asterisks represent significant differences between the PBS control; the bar with asterisks represents a significant difference between the n5 and n15 constructs. Activation caused by truncated YscF proteins is also MyD88-dependent. When MyD88 is absent, all YscF and YscF fragment induction disappears. See FIG. 25.

Example 17

Examining the Adjuvant Properties of frYscF

The adjuvant properties of a YscF fragment may be examined using in-vitro, ex-vivo, or in-vivo methods known to those of skill in the art, including methods described herein. For example, in-vitro treatment of human THP-1 or mouse macrophage cells with frYscF may reveal the ability of selected fragments of the YscF protein to elicit a proinflammatory cytokine response. Other suitable methods for examining the adjuvant properties of a YscF fragment include treating peritoneal or serum macrophage cells obtained from a suitable mammalian host with selected YscF fragments, ex vivo, and measuring NF-κB pathway activity and/or cytokine production, using methods known in the art.

Mice, or other suitable mammalian host models, may be administered frYscF, in vivo, to assess proinflammatory cytokine activation and frYscF-specific antibody production. The adjuvant properties of a YscF fragment may be evaluated, in vivo, for example, by vaccinating mice, or other suitable mammalian hosts, with selected YscF fragments, along with a known or potential antigen, such as the LcrV antigen, and assessing activation of proinflammatory markers, antibody production, or other indicators of an immune response. Similarly, the efficacy of YscF fragments to act as adjuvants in a vaccination protocol may be assessed, for example, by administering selected YscF fragments to mice or other suitable mammalian hosts, along with a suspected or known protective antigen against *Yersinia pestis*, such as LcrV. Survival following exposure of the host to *Y. pestis* may be used as an indicator of the ability of selected YscF fragments to enhance an immune response.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims and their legal equivalents.

REFERENCES

The contents of each of the following references are incorporated herein, in their entirety, by this reference:

Allaoui A., Schulte R., and Cornelis G. R. 1995. Mutational analysis of the *Yersinia enterocolitica* virC operon: characterization of yscE, F, G, I, J, K required for Yop secretion and yscH encoding YopR. Mol. Microbiol. 18:343-55.

Blocker A., Jouihri N., Larquet E., Gounon P., Ebel F., Parsot C., Sansonetti P., and Allaoui A. 2001. Structure and composition of the *Shigella flexneri* "needle complex", a part of its type III secreton. Mol. Microbiol. 39:652-63.

Benner, et al. 1999. Immune Response to *Yersinia* Outer Proteins and Other *Yersinia pestis* Antigens after Experimental Plague Infection in Mice. Infection and Immunity. Vol. 67, No. 4:1922-28

Cole, et al. 2001. A plague o' both your hosts. Nature 413:467-70.

Coligan J. E., Dunn B. M., Speicher D. W., and Wingfield P. T. (ed.). 1998. Current protocols in protein science. John Wiley & Sons, New York.

Cornelis, G. R. 2002. The *Yersinia* Ysc-Yop "type III" weaponry. Nat. Rev. Mol. Cell Biol 3:742-52.

Daniell, S. J., Takahashi N., Wilson R., Friedberg D., Rosenshine I., Booy F. P., Shaw R. K., Knutton S., Frankel G., and Aizawa S. 2001. The filamentous type III secretion translocon of enteropathogenic *Escherichia coli*. Cell Microbiol. 3:865-71.

Davis K. J., Fritz D. L., Pitt M. L., Welkos S. L., Worsham P. L., and Friedlander A. M. 1996. Pathology of experimental pneumonic plague produced by fraction 1-positive and fraction 1-negative *Yersinia pestis* in African green monkeys (*Cercopithecus aethiops*). Arch. Pathol. Lab. Med. 120:156-63.

Deane J. E., Cordes F. S., Roversi P., Johnson S., Kenjale R., Picking W. D., Picking W. L., Lea S. M., Blocker A. 2006. Expression, purification, crystallization and preliminary crystallographic analysis of MxiH, a subunit of the *Shigella flexneri* type III secretion system needle. Acta Crystallogr. Sect. F. Struct. Biol. Cryst. Commun. 62 (Pt 3):302-5.

Drozdov I. G., Anisimov A. P., Samoilova S. V., Yezhov I. N., Yeremin S. A., Karlyshev A. V., Krasilnikova V. M., and Kravchenko V. I. 1995. Virulent non-capsulate *Yersinia pestis* variants constructed by insertion mutagenesis. J. Med. Microbiol. 42:264-8.

Du Y., Galyov E., and Forsberg A. 1995. Genetic analysis of virulence determinants unique to *Yersinia pestis*. Contrib. Microbiol. Immunol. 13:321-4.

Edqvist, et al. 2003. YscP and YscU Regulate Substrate Specificity of the *Yersinia* Type III Secretion System. Journal of Bacteriology Vol. 185, No. 7:2259-66.

Fields, K. A., Nilles M. L., Cowan C., and Straley S. C. 1999. Virulence role of V antigen of *Yersinia pestis* at the bacterial surface. Infection and Immunity 67:5395-408.

Ghosh S., and Karin M. 2002. Missing pieces in the NF-kappaB puzzle. Cell 109 Suppl:S81-96.

Haddix P. L. and Straley S. C. 1992. Structure and regulation of the *Yersinia pestis* yscBCDEF operon. J. Bacteriol. 174: 4820-8.

Håkansson S., Schesser K., Persson C., Galyov E. E., Rosqvist R., Homblé F., and Wolf-Watz H. 1996. The YopB protein of *Yersinia pseudotuberculosis* is essential for the translocation of Yop effector proteins across the target cell plasma membrane and displays a contact-dependent membrane disrupting activity. EMBO Journal 15:5812-5823.

Hayashi F., Smith K. D., Ozinsky A., Hawn T. R., Yi E. C., Goodlett D. R., Eng J. K., Akira S., Underhill D. M., Aderem A. 2001. The innate immune response to bacterial flagellin is mediated by Toll-like receptor 5. Nature 410 (6832):1099-103.

Hill, et al. 2002. Immunological characterisation of sub-units of the *Yersinia* type III secretion apparatus, Abstract at the 8th International Symposium on *Yersinia*, September 4-8, Turku, Finland.

Hoiczyk, E., and Blobel G. 2001. Polymerization of a single protein of the pathogen *Yersinia enterocolitica* into needles punctures eukaryotic cells. Proc. Natl. Acad. Sci. USA 98:4669-74.

Holmström, A., Olsson J., Cherepanov P., Maier E., Nordfelth R., Pettersson J., Benz R., Wolf-Watz H., and Forsberg A. A. 2001. LcrV is a channel size-determining component of the Yop effector translocon of *Yersinia*. Mol. Microbiol. 39:620-632.

Hu, et al. 1998. Structural Organization of Virulence-Associated Plasmids of *Yersinia pestis*, Journal of Bacteriology. Vol. 180, No. 19:5192-202.

Inglesby, et al. 2000. Plague as a biological weapon: medical and public health management. Working Group on Civilian Biodefense. JAMA 283:2281-90.

Kenjale R., Wilson J., Zenk S. F., Saurya S., Picking W. L., Picking W. D., Blocker A. 2005. The needle component of the type III secreton of *Shigella* regulates the activity of the secretion apparatus. J. Biol. Chem. 280(52):42929-37.

Kubori, T., Matsushima Y., Nakamura D., Uralil J., Lara-Tejero M., Sukhan A., Galan J. E., and Aizawa S. I. 1998. Supramolecular structure of the *Salmonella typhimurium* type III protein secretion system. Science 280:602-605.

Kubori T., Sukhan A., Aizawa S. I., and Galan J. E. 2000. Molecular characterization and assembly of the needle complex of the *Salmonella typhimurium* type III protein secretion system. Proc. Natl. Acad. Sci. USA 97:10225-30.

Loquet A., et al. 2012. Atomic model of the type III secretion system needle. Nature 000:1-6.

Mathes E., O'Dea E. L., Hoffmann A., Ghosh G. 2008. NF-kappaB dictates the degradation pathway of IkappaBalpha. EMBO J. 27(9):1357-67.

Matson J. S., Durick K. A., Bradley D. S., Nilles M. L. 2005. Immunization of mice with YscF provides protection from *Yersinia pestis* infections. C. Microbiol. 5:38.

Michiels, et al. 1991. Analysis of virC, an Operon Involved in the Secretion of Yop Proteins by *Yersinia enterocolitica*. J. Bacteriol. 173:4994-5009.

Mizel S. B., et al. 2003. Induction of macrophage nitric oxide production by Gram-negative flagellin involves signaling via heteromeric Toll-like receptor 5/Toll-like receptor 4 complexes. J. Immunol. 170(12):6217-23.

Needleman S. B. and Wunsch CD. 1970. A general method applicable to the search for similarities in the amino acid sequence of two proteins. J. Mol. Biol. 48:443-453.

Nilles, M. L., Fields K. A., and Straley S. C. 1998. The V antigen of *Yersinia pestis* regulates Yop vectorial targeting as well as Yop secretion through effects on YopB and LcrG. J. Bacteriol. 180:3410-3420.

Nordfelth, R., and Wolf-Watz H. 2001. YopB of *Yersinia enterocolitica* is Essential for YopE Translocation. Infect. Immun. 69:3516-8.

Oyston, et al., *Yersinia*: an update, <http://tim.trends.com>, pp. 550-51.

Parkhill, et al. 2001. Genome sequence of *Yersinia pestis*, the causative agent of plague. Nature 413:523-527.

Perry R. D. and Fetherson J. D. 1997. *Yersinia pestis*—etiologic agent of plague. Clinical Microbiology Reviews 10:35-66.

Perry R. D., Straley S. C., Fetherston J. D., Rose D. J., Gregor J., and Blattner F. R. 1998. DNA sequencing and analysis of the low-Ca2+-response plasmid pCD1 of *Yersinia pestis* KIM5. Infection and Immunity 66:4611-4623.

Pettersson, et al. 1999. The V-antigen of *Yersinia* is surface-exposed before target cell contact and involved in virulence protein translocation. Mol. Microbiol. 32:961-976.

Plotkin, et al. 1988. Vaccines, p. 571, W.B. Saunders Co.

Scheidereit C. 2006. IkappaB kinase complexes: gateways to NF-kappaB activation and transcription. Oncogene 25(51):6685-705. Review.

Sekiya, K., Ohishi M., Ogino T., Tamano K., Sasakawa C., and Abe A. 2001. Supermolecular structure of the enteropathogenic *Escherichia coli* type III secretion system and its direct interaction with the EspA-sheath-like structure. Proc. Natl. Acad. Sci. USA 98:11638-43.

Sory M. P. and Cornelis G. R. 1994. Translocation of a hybrid YopE-adenylate cyclase from *Yersinia enterocolitica* into HeLa cells. Mol. Microbiol. 14:583-594.

Tardy F., et al. 1999. *Yersinia enterocolitica* type III secretion-translocation system: channel formation by secreted Yops. EMBO 18:6793-6799.

Titball R. W., Howells A. M., Oyston P. C., and Williamson E. D. 1997. Expression of the *Yersinia pestis* capsular antigen (F1 antigen) on the surface of an aroA mutant of *Salmonella typhimurium* induces high levels of protection against plague. Infect. Immun. 65(5): 1926-30.

Titball, R. W. and Williamson E. D. 2001. Vaccination against bubonic and pneumonic plague. Vaccine 19:4175-84.

Viatour P., Merville M. P., Bours V., Chariot A. 2005. Phosphorylation of NF-kappaB and IkappaB proteins: implications in cancer and inflammation. Trends Biochem. Sci. 30(1):43-52.

Welkos S. and O'Brien A. 1994. Determination of median lethal and infectious doses in animal model systems. Methods Enzymol. 235:29-39.

Welkos, S. L., et al. 1995. Studies on the contribution of the F1 capsule-associated plasmid pFra to the virulence of Yersinia pestis. Contrib. Microbiol. Immunol. 13:299-305.

Williamson E. D. 2001. Plague vaccine research and development, J. App. Microbiol. 91:606-08.

Williamson E. D., et al. 1999. An IgG1 titre to the F1 and V antigens correlates with protection against plague in the mouse model. Clin. Exp. Immunol. 116:107-14.

Wilson, R. K., et al. 2001. Role of EscF, a putative needle complex protein, in the type III protein translocation system of enteropathogenic Escherichia coli. Cell Microbiol. 3:753-62.

8th International Symposium on Yersinia, Sep. 4-8, 2002. Turku, Finland.

Wilson, et al. 2001. Role of EscF, a putative needle complex protein, in the type III protein translocation system of enteropathogenic Escherichia coli, Cell. Microbiol. 3:753-62.

What is claimed is:

1. A composition comprising:
   an antigen and
   an effective adjuvanting amount of recombinant Type III needle protein, wherein the Type III needle protein comprises an effective fragment of YscF protein.

2. The composition of claim 1, wherein the effective fragment of YscF protein comprises SEQ ID NO:27, SEQ ID NO:28, SEQ ID NO:29, or SEQ ID NO:30.

3. The composition of claim 1, wherein the effective fragment of YscF protein comprises a truncated YscF protein (SEQ ID NO:2).

4. The composition of claim 1, further comprising a diluent, carrier, or excipient.

5. The composition of claim 1, wherein the antigen is a *Yersinia* antigen.

6. The composition of claim 5, wherein the antigen is a *Yersinia pestis* pathogen.

7. The composition of claim 6, wherein the antigen comprises LcrV, the F1 antigen, fragments or truncated forms thereof, or a combination thereof.

8. A composition comprising:
   an effective adjuvanting amount of the peptide of SEQ ID NO:2, and
   a *Yersinia* antigen.

9. A method of inducing an enhanced immune response in a subject, the method comprising administering the composition of claim 1 to the subject.

10. The method according to claim 9, wherein the antigen of the composition is a *Yersinia* pathogen.

11. The method according to claim 10, wherein the antigen of the composition is a *Yersinia pestis* pathogen.

12. The method according to claim 11, wherein the antigen of the composition comprises LcrV, the F1 antigen, fragments or truncated forms thereof, or a combination thereof.

13. The method according to claim 9, wherein the antigen of the composition comprises PrgI, MxiH, SsaG, fragments or truncated forms thereof, or a combination thereof.

14. A process for producing the composition of claim 1, the process comprising:
   providing a host cell with an expression vector comprising a polynucleotide encoding a Type III needle protein that comprises an effective fragment of YscF protein;
   expressing the polynucleotide in the host cell to produce the effective fragment of YscF protein; and
   mixing an effective adjuvanting amount of collected effective fragment of YscF protein with antigen so as to produce the composition.

15. The process of claim 14, wherein the polynucleotide encodes SEQ ID NO:27, SEQ ID NO:28, SEQ ID NO:29, or SEQ ID NO:30.

16. The process of claim 14, wherein the polynucleotide encodes SEQ ID NO:2.

17. The process according to claim 14, further comprising mixing a diluent, excipient, or a carrier with the mixture of effective adjuvanting amount of collected effective fragment of YscF protein and antigen.

18. The composition of claim 1, wherein the antigen comprises a *Yersinia* antigen.

19. The composition of claim 18, wherein the effective fragment of YscF protein is selected from the group consisting of SEQ ID NO:2, SEQ ID NO:27, SEQ ID NO:28, SEQ ID NO:29, and SEQ ID NO:30.

20. A method for screening for an immunological response to a *Yersinia* pathogen, the method comprising:
   exposing mammalian cells to a *Yersinia* antigen;
   adding the composition of claim 1 to the mammalian cells exposed to the *Yersinia* antigen; and
   evaluating the immune response of the mammalian cells to the composition.

21. The method of claim 20, wherein the immune response is evaluated by measuring levels of proinflammatory cytokine expression, or measuring an antigen-specific antibody response.

22. A method for vaccinating a subject against *Yersinia* infection, the method comprising:
   administering the composition of claim 1 to the subject.

23. The method of claim 22, wherein the effective fragment of YscF protein is selected from the group consisting of SEQ ID NO:2, SEQ ID NO:27, SEQ ID NO:28, SEQ ID NO:29, and SEQ ID NO:30.

24. A composition comprising:
   an antigen, wherein the antigen comprises LcrV, the F1 antigen, fragments or truncated forms thereof, or a combination thereof;
   a composition comprising an effective adjuvanting amount of the peptide of SEQ ID NO:2, and a *Yersinia* antigen; and
   a suitable diluent, carrier, and/or excipient.

25. A composition comprising:
   an antigen, wherein the antigen comprises PrgI, MxiH, SsaG, fragments or truncated forms thereof, or a combination thereof;
   a composition comprising an effective adjuvanting amount of the peptide of SEQ ID NO:2, and a *Yersinia* antigen; and
   a suitable diluent, carrier, and/or excipient.

* * * * *

SEQUENCE LISTING

```
<160> NUMBER OF SEQ ID NOS: 30

<210> SEQ ID NO 1
<211> LENGTH: 87
<212> TYPE: PRT
<213> ORGANISM: Yersinia pestis
<220> FEATURE:
<221> NAME/KEY: MISC_FEATURE
<223> OTHER INFORMATION: wtYscF amino acid sequence

<400> SEQUENCE: 1

Met Ser Asn Phe Ser Gly Phe Thr Lys Gly Thr Asp Ile Ala Asp Leu
1               5                   10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro
                85

<210> SEQ ID NO 2
<211> LENGTH: 65
<212> TYPE: PRT
<213> ORGANISM: Artificial
<220> FEATURE:
<223> OTHER INFORMATION: trYscF amino acid sequence

<400> SEQUENCE: 2

Leu Lys Lys Pro Ala Asp Asp Ala Asn Lys Ala Val Asn Asp Ser Ile
1               5                   10                  15

Ala Ala Leu Lys Asp Lys Pro Asp Asn Pro Ala Leu Leu Ala Asp Leu
            20                  25                  30

Gln His Ser Ile Asn Lys Trp Ser Val Ile Tyr Asn Ile Asn Ser Thr
        35                  40                  45

Ile Val Arg Ser Met Lys Asp Leu Met Gln Gly Ile Leu Gln Lys Phe
    50                  55                  60

Pro
65

<210> SEQ ID NO 3
<211> LENGTH: 38
<212> TYPE: DNA
<213> ORGANISM: Artificial
<220> FEATURE:
<223> OTHER INFORMATION: TrncYscFStartMT primer
```

```
<400> SEQUENCE: 3
caccctcaag aagccagcag acgatgcaaa caaagcgg                                      38

<210> SEQ ID NO 4
<211> LENGTH: 33
<212> TYPE: DNA
<213> ORGANISM: Artificial
<220> FEATURE:
<223> OTHER INFORMATION: TrnctYscFStopMT primer

<400> SEQUENCE: 4
ttatgggaac ttctgtagga tgccttgcat taa                                           33

<210> SEQ ID NO 5
<211> LENGTH: 5939
<212> TYPE: DNA
<213> ORGANISM: Artificial
<220> FEATURE:
<223> OTHER INFORMATION: pMNT67 plasmid
<220> FEATURE:
<221> NAME/KEY: misc_feature
<222> LOCATION: (1)..(5)
<223> OTHER INFORMATION: TOPO recognition site II
<220> FEATURE:
<221> NAME/KEY: misc_feature
<222> LOCATION: (23)..(151)
<223> OTHER INFORMATION: T7 transcription termination region
<220> FEATURE:
<221> NAME/KEY: misc_feature
<222> LOCATION: (62)..(81)
<223> OTHER INFORMATION: T7 reverse priming site
<220> FEATURE:
<221> NAME/KEY: misc_feature
<222> LOCATION: (551)..(1345)
<223> OTHER INFORMATION: kan
<220> FEATURE:
<221> NAME/KEY: misc_feature
<222> LOCATION: (1565)..(2206)
<223> OTHER INFORMATION: pBR322 Origin
<220> FEATURE:
<221> NAME/KEY: misc_feature
<222> LOCATION: (2574)..(2765)
<223> OTHER INFORMATION: ROP ORF on complementary strand
<220> FEATURE:
<221> NAME/KEY: misc_feature
<222> LOCATION: (4077)..(5168)
<223> OTHER INFORMATION: LacI ORF on complementary strand
<220> FEATURE:
<221> NAME/KEY: misc_feature
<222> LOCATION: (5565)..(5589)
<223> OTHER INFORMATION: Lac operator
<220> FEATURE:
<221> NAME/KEY: misc_feature
<222> LOCATION: (5634)..(5636)
<223> OTHER INFORMATION: Initiation ATG
<220> FEATURE:
<221> NAME/KEY: misc_feature
<222> LOCATION: (5646)..(5663)
<223> OTHER INFORMATION: Polyhistidine
<220> FEATURE:
<221> NAME/KEY: misc_feature
<222> LOCATION: (5703)..(5726)
<223> OTHER INFORMATION: Express epitope
<220> FEATURE:
<221> NAME/KEY: misc_feature
<222> LOCATION: (5712)..(5726)
<223> OTHER INFORMATION: EK recognition site
<220> FEATURE:
<221> NAME/KEY: misc_feature
<222> LOCATION: (5733)..(5737)
<223> OTHER INFORMATION: TOPO recognition site I
<220> FEATURE:
<221> NAME/KEY: CDS
<222> LOCATION: (5742)..(5939)
<223> OTHER INFORMATION: trYscF
```

<400> SEQUENCE: 5

```
aagggcgagc tcaacgatcc ggctgctaac aaagcccgaa aggaagctga gttggctgct      60
gccaccgctg agcataaact agcataaccc cttggggcct ctaaacgggt cttgaggagt     120
tttttgctga aaggaggaac tatatccgga tatcccgcaa gaggcccggc agtaccggca     180
taaccaagcc tatgcctaca gcatccaggg tgacggtgcc gaggatgacg atgagcgcat     240
tgttagattt catacacggt gcctgactgc gttagcaatt taactgtgat aaactaccgc     300
attaaagctt atcgatgata agctgtcaaa catgagaatt aattcttgaa gacgaaaggg     360
cctcgtgata cgcctatttt tataggttaa tgtcatgata ataatggttt cttagacgtc     420
aggtggcact tttcggggaa atgtgcgcgg aacccctatt tgtttatttt tctaaataca     480
ttcaaatatg tatccgctca tgagacaata accctgataa atgcttcaat aatattgaaa     540
aaggaagagt atgattgaac aagatggatt gcacgcaggt tctccggccg cttgggtgga     600
gaggctattc ggctatgact gggcacaact gacaatcggc tgctctgatg ccgccgtgtt     660
ccggctgtca gcgcaggggc gcccggttct ttttgtcaag accgacctgt ccggtgccct     720
gaatgaactg caggacgagg cagcgcggct atcgtggctg gccacgacgg gcgttccttg     780
cgcagctgtg ctcgacgttg tcactgaagc gggaaggac tggctgctat tgggcgaagt     840
gccggggcag gatctcctgt catctcacct tgctcctgcc gagaaagtat ccatcatggc     900
tgatgcaatg cggcggctgc atacgcttga tccggctacc tgcccattcg accaccaagc     960
gaaacatcgc atcgagcggg cacgtactcg gatggaagcc ggtcttgtcg atcaggatga    1020
tctggacgaa gagcatcagg ggctcgcgcc agccgaactg ttcgccaggc tcaaggcgcg    1080
catgcccgac ggcgaggatc tcgtcgtgac acatggcgat gcctgcttgc cgaatatcat    1140
ggtgaaaaat ggccgctttt ctggattcat cgactgtggc cggctgggtg tggcggaccg    1200
ctatcaggac atagcgttgg ctacccgtga tattgctgaa gagcttggcg gcgaatgggc    1260
tgaccgcttc ctcgtgcttt acggtatcgc cgctcccgat tcgcagcgca tcgccttcta    1320
tcgccttctt gacgagttct ctgagcgggg actctggggt tcgaaatgac cgaccaagcg    1380
acgcctaact gtcagaccaa gtttactcat atatacttta gattgattta aaacttcatt    1440
tttaatttaa aaggatctag gtgaagatcc tttttgataa tctcatgacc aaaatccctt    1500
aacgtgagtt tcgttccac tgagcgtcag accccgtaga aaagatcaaa ggatcttctt    1560
gagatccttt ttttctgcgc gtaatctgct gcttgcaaac aaaaaaacca ccgctaccag    1620
cggtggtttg tttgccggat caagagctac caactctttt tccgaaggta actggcttca    1680
gcagagcgca gataccaaat actgtccttc tagtgtagcc gtagttaggc caccacttca    1740
agaactctgt agcaccgcct acatacctcg ctctgctaat cctgttacca gtggctgctg    1800
ccagtggcga taagtcgtgt cttaccgggt tggactcaag acgatagtta ccggataagg    1860
cgcagcggtc gggctgaacg gggggttcgt gcacacagcc cagcttggag cgaacgacct    1920
acaccgaact gagataccta cagcgtgagc tatgagaaag cgccacgctt cccgaaggga    1980
gaaaggcgga caggtatccg gtaagcggca gggtcggaac aggagagcgc acgagggagc    2040
ttccaggggg aaacgcctgg tatctttata gtcctgtcgg gtttcgccac ctctgacttg    2100
agcgtcgatt tttgtgatgc tcgtcagggg ggcggagcct atggaaaaac gccagcaacg    2160
cggccttttt acggttcctg gccttttgct ggccttttgc tcacatgttc tttcctgcgt    2220
tatccctga ttctgtggat aaccgtatta ccgcctttga gtgagctgat accgctcgcc    2280
gcagccgaac gaccgagcgc agcgagtcag tgagcgagga agcggaagag cgcctgatgc    2340
```

```
ggtattttct ccttacgcat ctgtgcggta tttcacaccg caatggtgca ctctcagtac      2400
aatctgctct gatgccgcat agttaagcca gtatacactc cgctatcgct acgtgactgg      2460
gtcatggctg cgccccgaca cccgccaaca cccgctgacg cgccctgacg ggcttgtctg      2520
ctcccggcat ccgcttacag acaagctgtg accgtctccg ggagctgcat gtgtcagagg      2580
ttttcaccgt catcaccgaa acgcgcgagg cagctgcggt aaagctcatc agcgtggtcg      2640
tgaagcgatt cacagatgtc tgcctgttca tccgcgtcca gctcgttgag tttctccaga      2700
agcgttaatg tctggcttct gataaagcgg gccatgttaa gggcggtttt tcctgtttg      2760 gtcactgatg cctccgtgta aggggattt ctgttcatgg gggtaatgat accgatgaaa      2820
cgagagagga tgctcacgat acgggttact gatgatgaac atgcccggtt actggaacgt      2880
tgtgagggta acaactggc ggtatggatg cggcgggacc agagaaaaat cactcagggt      2940
caatgccagc gcttcgttaa tacagatgta ggtgttccac agggtagcca gcagcatcct      3000
gcgatgcaga tccggaacat aatggtgcag ggcgctgact ccgcgtttc cagactttac      3060 gaaacacgga aaccgaagac cattcatgtt gttgctcagg tcgcagacgt tttgcagcag      3120
cagtcgcttc acgttcgctc gcgtatcggt gattcattct gctaaccagt aaggcaaccc      3180
cgccagccta gccgggtcct caacgacagg agcacgatca tgcgcacccg tggccaggac      3240
ccaacgctgc ccgagatgcg ccgcgtgcgg ctgctggaga tggcggacgc gatggatatg      3300
ttctgccaag ggttggtttg cgcattcaca gttctccgca agaattgatt ggctccaatt      3360
cttggagtgg tgaatccgtt agcgaggtgc cgccggcttc cattcaggtc gaggtggccc      3420
ggctccatgc accgcgacgc aacgcgggga ggcagacaag gtatagggcg cgcctacaa      3480 tccatgccaa cccgttccat gtgctcgccg aggcggcata aatcgccgtg acgatcagcg      3540
gtccaatgat cgaagttagg ctggtaagag ccgcagcga tccttgaagc tgtccctgat      3600
ggtcgtcatc tacctgcctg acagcatgg cctgcaacgc gggcatcccg atgccgccgg      3660
aagcgagaag aatcataatg gggaaggcca tccagcctcg cgtcgcgaac gccagcaaga      3720
cgtagcccag cgcgtcggcc gccatgccgg cgataatggc ctgcttctcg ccgaaacgtt      3780
tggtggcggg accagtgacg aaggcttgag cgagggcgtg caagattccg aataccgcaa      3840
gcgacaggcc gatcatcgtc gcgctccagc gaaagcggtc ctcgccgaaa atgacccaga      3900
gcgctgccgg cacctgtcct acgagttgca tgataaagaa gacagtcata agtgcggcga      3960
cgatagtcat gccccgcgcc caccggaagg agctgactgg gttgaaggct ctcaagggca      4020
tcggtcgaga tccggtgcc taatgagtga gctaacttac attaattgcg ttgcgctcac      4080
tgcccgcttt ccagtcggga aacctgtcgt gccagctgca ttaatgaatc ggccaacgcg      4140
cggggagagg cggtttgcgt attgggcgcc agggtggttt ttcttttcac cagtgagacg      4200
ggcaacagct gattgccctt caccgcctgg ccctgagaga gttgcagcaa gcggtccacg      4260
ctggtttgcc ccagcaggcg aaaatcctgt ttgatggtgg ttaacggcgg gatataacat      4320
gagctgtctt cggtatcgtc gtatcccact accgagatat ccgcaccaac gcgcagcccg      4380
gactcggtaa tggcgcgcat tgcgcccagc gccatctgat cgttggcaac cagcatcgca      4440
gtgggaacga tgcctcatt cagcatttgc atggtttgtt gaaaccgga catggcactc      4500 cagtcgcctt cccgttccgc tatcggctga atttgattgc gagtgagata tttatgccag      4560
ccagccagac gcagacgcgc cgagacgaaa cttaatgggc ccgctaacag cgcgatttgc      4620
tggtgaccca atgcgaccag atgctccacg cccagtcgcg taccgtcttc atgggagaaa      4680
ataatactgt tgatgggtgt ctggtcagag acatcaagaa ataacgccgg aacattagtg      4740
```

```
caggcagctt ccacagcaat ggcatcctgg tcatccagcg atagttaat gatcagccca    4800 ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acggcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accatacccca cgccgaaaca    5400 agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta taggggaatt gtgagcggat    5580
aacaattccc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac c ctc aag aag cca gca    5756
                                            Leu Lys Lys Pro Ala
                                              1               5 gac gat gca aac aaa gcg gtt aat gac tcg ata gca gca ttg aaa gat    5804
Asp Asp Ala Asn Lys Ala Val Asn Asp Ser Ile Ala Ala Leu Lys Asp
             10                  15                  20 aag cct gac aac ccg gcg cta ctt gct gac tta caa cat tca att aat    5852
Lys Pro Asp Asn Pro Ala Leu Leu Ala Asp Leu Gln His Ser Ile Asn
         25                  30                  35 aaa tgg tcg gta att tac aat ata aac tca acc ata gtt cgt agc atg    5900
Lys Trp Ser Val Ile Tyr Asn Ile Asn Ser Thr Ile Val Arg Ser Met
     40                  45                  50 aaa gac tta atg caa ggc atc cta cag aag ttc cca taa               5939
Lys Asp Leu Met Gln Gly Ile Leu Gln Lys Phe Pro
 55                  60                  65
```

<210> SEQ ID NO 6
<211> LENGTH: 65
<212> TYPE: PRT
<213> ORGANISM: Artificial
<220> FEATURE:
<223> OTHER INFORMATION: Synthetic Construct

<400> SEQUENCE: 6

```
Leu Lys Lys Pro Ala Asp Asp Ala Asn Lys Ala Val Asn Asp Ser Ile
  1               5                  10                  15

Ala Ala Leu Lys Asp Lys Pro Asp Asn Pro Ala Leu Leu Ala Asp Leu
             20                  25                  30

Gln His Ser Ile Asn Lys Trp Ser Val Ile Tyr Asn Ile Asn Ser Thr
         35                  40                  45

Ile Val Arg Ser Met Lys Asp Leu Met Gln Gly Ile Leu Gln Lys Phe
     50                  55                  60

Pro
 65
```

<210> SEQ ID NO 7
<211> LENGTH: 80
<212> TYPE: PRT
<213> ORGANISM: Salmonella enterica
<220> FEATURE:
<221> NAME/KEY: MISC_FEATURE
<223> OTHER INFORMATION: wtPrgI amino acid sequence

<400> SEQUENCE: 7

Met Ala Thr Pro Trp Ser Gly Tyr Leu Asp Asp Val Ser Ala Lys Phe
1               5                   10                  15

Asp Thr Gly Val Asp Asn Leu Gln Thr Gln Val Thr Glu Ala Leu Asp
            20                  25                  30

Lys Leu Ala Ala Lys Pro Ser Asp Pro Ala Leu Leu Ala Ala Tyr Gln
        35                  40                  45

Ser Lys Leu Ser Glu Tyr Asn Leu Tyr Arg Asn Ala Gln Ser Asn Thr
    50                  55                  60

Val Lys Val Phe Lys Asp Ile Asp Ala Ala Ile Ile Gln Asn Phe Arg
65                  70                  75                  80

<210> SEQ ID NO 8
<211> LENGTH: 63
<212> TYPE: PRT
<213> ORGANISM: Artificial
<220> FEATURE:
<223> OTHER INFORMATION: trPrgI amino acid sequence

<400> SEQUENCE: 8

Thr Gly Val Asp Asn Leu Gln Thr Gln Val Thr Glu Ala Leu Asp Lys
1               5                   10                  15

Leu Ala Ala Lys Pro Ser Asp Pro Ala Leu Leu Ala Ala Tyr Gln Ser
            20                  25                  30

Lys Leu Ser Glu Tyr Asn Leu Tyr Arg Asn Ala Gln Ser Asn Thr Val
        35                  40                  45

Lys Val Phe Lys Asp Ile Asp Ala Ala Ile Ile Gln Asn Phe Arg
    50                  55                  60

<210> SEQ ID NO 9
<211> LENGTH: 83
<212> TYPE: PRT
<213> ORGANISM: Shigella flexneri
<220> FEATURE:
<221> NAME/KEY: MISC_FEATURE
<223> OTHER INFORMATION: wtMxiH amino acid sequence

<400> SEQUENCE: 9

Met Ser Val Thr Val Pro Asn Asp Asp Trp Thr Leu Ser Ser Leu Ser
1               5                   10                  15

Glu Thr Phe Asp Asp Gly Thr Gln Thr Leu Gln Gly Glu Leu Thr Leu
            20                  25                  30

Ala Leu Asp Lys Leu Ala Lys Asn Pro Ser Asn Pro Gln Leu Leu Ala
        35                  40                  45

Glu Tyr Gln Ser Lys Leu Ser Glu Tyr Thr Leu Tyr Arg Asn Ala Gln
    50                  55                  60

Ser Asn Thr Val Lys Val Ile Lys Asp Val Asp Ala Ala Ile Ile Gln
65                  70                  75                  80

Asn Phe Arg

-continued

```
<210> SEQ ID NO 10
<211> LENGTH: 65
<212> TYPE: PRT
<213> ORGANISM: Artificial
<220> FEATURE:
<223> OTHER INFORMATION: trMxiH amino acid sequence

<400> SEQUENCE: 10

Phe Asp Asp Gly Thr Gln Thr Leu Gln Gly Glu Leu Thr Leu Ala Leu
1               5                   10                  15

Asp Lys Leu Ala Lys Asn Pro Ser Pro Gln Leu Leu Ala Glu Tyr
            20                  25                  30

Gln Ser Lys Leu Ser Glu Tyr Thr Leu Tyr Arg Asn Ala Gln Ser Asn
            35                  40                  45

Thr Val Lys Val Ile Lys Asp Val Asp Ala Ala Ile Ile Gln Asn Phe
        50                  55                  60

Arg
65

<210> SEQ ID NO 11
<211> LENGTH: 71
<212> TYPE: PRT
<213> ORGANISM: Salmonella sp.
<220> FEATURE:
<221> NAME/KEY: MISC_FEATURE
<223> OTHER INFORMATION: wtSsaG amino acid sequence

<400> SEQUENCE: 11

Met Asp Ile Ala Gln Leu Val Asp Met Leu Ser His Met Ala His Gln
1               5                   10                  15

Ala Gly Gln Ala Ile Asn Asp Lys Met Asn Gly Asn Asp Leu Leu Asn
            20                  25                  30

Pro Glu Ser Met Ile Lys Ala Gln Phe Ala Leu Gln Gln Tyr Ser Thr
            35                  40                  45

Phe Ile Asn Tyr Glu Ser Ser Leu Ile Lys Met Ile Lys Asp Met Leu
        50                  55                  60

Ser Gly Ile Ile Ala Lys Ile
65                  70

<210> SEQ ID NO 12
<211> LENGTH: 98
<212> TYPE: PRT
<213> ORGANISM: Artificial
<220> FEATURE:
<223> OTHER INFORMATION: His6-trSsaG amino acid sequence

<400> SEQUENCE: 12

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Leu Ser His Met Ala His Gln Ala Gly Gln Ala Ile
            35                  40                  45

Asn Asp Lys Met Asn Gly Asn Asp Leu Leu Asn Pro Glu Ser Met Ile
        50                  55                  60

Lys Ala Gln Phe Ala Leu Gln Gln Tyr Ser Thr Phe Ile Asn Tyr Glu
65                  70                  75                  80

Ser Ser Leu Ile Lys Met Ile Lys Asp Met Leu Ser Gly Ile Ile Ala
                85                  90                  95

Lys Ile
```

-continued

```
<210> SEQ ID NO 13
<211> LENGTH: 102
<212> TYPE: PRT
<213> ORGANISM: Artificial
<220> FEATURE:
<223> OTHER INFORMATION: His6-trYscF amino acid sequence

<400> SEQUENCE: 13

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Thr Leu Lys Lys Pro Ala Asp Ala Asn Lys Ala
        35                  40                  45

Val Asn Asp Ser Ile Ala Ala Leu Lys Asp Lys Pro Asp Asn Pro Ala
    50                  55                  60

Leu Leu Ala Asp Leu Gln His Ser Ile Asn Lys Trp Ser Val Ile Tyr
65                  70                  75                  80

Asn Ile Asn Ser Thr Ile Val Arg Ser Met Lys Asp Leu Met Gln Gly
                85                  90                  95

Ile Leu Gln Lys Phe Pro
            100

<210> SEQ ID NO 14
<211> LENGTH: 309
<212> TYPE: DNA
<213> ORGANISM: Artificial
<220> FEATURE:
<223> OTHER INFORMATION: His6-tr-yscF coding sequence (pET200)

<400> SEQUENCE: 14
atgcggggtt ctcatcatca tcatcatcat ggtatggcta gcatgactgg tggacagcaa      60
atgggtcggg atctgtacga cgatgacgat aaggatcatc ccttcaccac gctcaagaag     120
ccagcagacg atgcaaacaa agcggttaat gactcgatag cagcattgaa agataagcct     180
gacaacccgg cgctacttgc tgacttacaa cattcaatta ataaatggtc ggtaatttac     240
aatataaact caaccatagt tcgtagcatg aaagacttaa tgcaaggcat cctacagaag     300
ttcccataa                                                              309

<210> SEQ ID NO 15
<211> LENGTH: 243
<212> TYPE: DNA
<213> ORGANISM: Salmonella enterica
<220> FEATURE:
<221> NAME/KEY: misc_feature
<223> OTHER INFORMATION: wt-prgI coding sequence

<400> SEQUENCE: 15
atggcaacac cttggtcagg ctatctggat gacgtctcag caaaatttga tacgggcgtt      60
gataatctac aaacgcaggt aacagaggcg ctggataaat agcagcaaa accctccgat     120 ccggcgctac tggcggcgta tcagagtaag ctctcggaat ataacttgta ccgtaacgcg     180
caatcgaaca cggtaaaagt ctttaaggat attgatgctg ccattattca gaacttccgt     240
taa                                                                    243

<210> SEQ ID NO 16
<211> LENGTH: 247
<212> TYPE: DNA
<213> ORGANISM: Artificial
```

```
<220> FEATURE:
<223> OTHER INFORMATION: prgI DNA construct (pET200)

<400> SEQUENCE: 16
caccatggca acaccttggt caggctatct ggatgacgtc tcagcaaaat ttgatacggg      60
cgttgataat ctacaaacgc aggtaacaga ggcgctggat aaattagcag caaaaccctc     120
cgatccggcg ctactggcgg cgtatcagag taagctctcg aatataact tgtaccgtaa      180 cgcgcaatcg aacacggtaa aagtctttaa ggatattgat gctgccatta ttcagaactt     240
ccgttaa                                                              247

<210> SEQ ID NO 17
<211> LENGTH: 21
<212> TYPE: DNA
<213> ORGANISM: Artificial
<220> FEATURE:
<223> OTHER INFORMATION: wtPrgI forward primer

<400> SEQUENCE: 17
caccatggca acaccttggt c                                               21

<210> SEQ ID NO 18
<211> LENGTH: 26
<212> TYPE: DNA
<213> ORGANISM: Artificial
<220> FEATURE:
<223> OTHER INFORMATION: wtPrgI reverse primer

<400> SEQUENCE: 18
ttaacggaag ttctgaataa tggcag                                          26

<210> SEQ ID NO 19
<211> LENGTH: 116
<212> TYPE: PRT
<213> ORGANISM: Artificial
<220> FEATURE:
<223> OTHER INFORMATION: His6-PrgI amino acid sequence

<400> SEQUENCE: 19

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Met Ala Thr Pro Trp Ser Gly Tyr Leu Asp Asp Val
        35                  40                  45

Ser Ala Lys Phe Asp Thr Gly Val Asp Asn Leu Gln Thr Gln Val Thr
    50                  55                  60

Glu Ala Leu Asp Lys Leu Ala Ala Lys Pro Ser Asp Pro Ala Leu Leu
65                  70                  75                  80

Ala Ala Tyr Gln Ser Lys Leu Ser Glu Tyr Asn Leu Tyr Arg Asn Ala
                85                  90                  95

Gln Ser Asn Thr Val Lys Val Phe Lys Asp Ile Asp Ala Ala Ile Ile
            100                 105                 110

Gln Asn Phe Arg
        115

<210> SEQ ID NO 20
<211> LENGTH: 252
<212> TYPE: DNA
<213> ORGANISM: Shigella flexneri
```

<220> FEATURE:
<221> NAME/KEY: misc_feature
<223> OTHER INFORMATION: wt-mxiH coding sequence

<400> SEQUENCE: 20

```
atgagtgtta cagtaccgaa tgatgattgg acattgagtt cattatctga aacttttgat    60
gatggaactc aaacattaca aggtgaacta acattggcac tagataaatt agctaaaaat   120
ccttcgaatc cacagttgct ggctgaatac caaagtaaat tatctgaata tacattatat   180
aggaacgcgc aatccaatac agtgaaagtg attaaggatg ttgatgctgc aattattcaa   240
aacttcagat aa                                                       252
```

<210> SEQ ID NO 21
<211> LENGTH: 198
<212> TYPE: DNA
<213> ORGANISM: Artificial
<220> FEATURE:
<223> OTHER INFORMATION: tr-mxiH coding sequence (pET200)

<400> SEQUENCE: 21

```
tttgatgatg gaactcaaac attacaaggt gaactaacat tggcactaga taaattagct    60
aaaaatcctt cgaatccaca gttgctggct gaataccaaa gtaaattatc tgaatataca   120
ttatatagga acgcgcaatc caatacagtg aaagtgatta aggatgttga tgctgcaatt   180
attcaaaact tcagataa                                                 198
```

<210> SEQ ID NO 22
<211> LENGTH: 216
<212> TYPE: DNA
<213> ORGANISM: Salmonella sp.
<220> FEATURE:
<221> NAME/KEY: misc_feature
<223> OTHER INFORMATION: wt-ssaG coding sequence

<400> SEQUENCE: 22

```
atggatattg cacaattagt ggatatgctc tcccacatgg cgcaccaggc aggccaggcc    60
attaatgaca aaatgaatgg taatgatttg ctcaacccag aatcgatgat aaagcgcaa    120
tttgccttac agcagtattc tacatttatt aattacgaaa gttcactgat caaaatgatc   180
aaggatatgc ttagtggaat cattgctaaa atctga                             216
```

<210> SEQ ID NO 23
<211> LENGTH: 107
<212> TYPE: PRT
<213> ORGANISM: Artificial
<220> FEATURE:
<223> OTHER INFORMATION: His6-SsaG amino acid sequence

<400> SEQUENCE: 23

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Met Asp Ile Ala Gln Leu Val Asp Met Leu Ser His
        35                  40                  45

Met Ala His Gln Ala Gly Gln Ala Ile Asn Asp Lys Met Asn Gly Asn
    50                  55                  60

Asp Leu Leu Asn Pro Glu Ser Met Ile Lys Ala Gln Phe Ala Leu Gln
65                  70                  75                  80
```

-continued

```
Gln Tyr Ser Thr Phe Ile Asn Tyr Glu Ser Ser Leu Ile Lys Met Ile
                85                  90                  95

Lys Asp Met Leu Ser Gly Ile Ile Ala Lys Ile
            100                 105

<210> SEQ ID NO 24
<211> LENGTH: 324
<212> TYPE: DNA
<213> ORGANISM: Artificial
<220> FEATURE:
<223> OTHER INFORMATION: His6-SsaG coding sequence

<400> SEQUENCE: 24
atgcggggtt ctcatcatca tcatcatcat ggtatggcta gcatgactgg tggacagcaa      60
atgggtcggg atctgtacga cgatgacgat aaggatcatc ccttcaccat ggatattgca     120
caattagtgg atatgctctc ccacatggcg caccaggcag gccaggccat taatgacaaa     180
atgaatggta atgatttgct caacccagaa tcgatgatta aagcgcaatt tgccttacag     240
cagtattcta catttattaa ttacgaaagt tcactgatca aatgatcaa ggatatgctt      300 agtggaatca ttgctaaaat ctga                                            324

<210> SEQ ID NO 25
<211> LENGTH: 297
<212> TYPE: DNA
<213> ORGANISM: Artificial
<220> FEATURE:
<223> OTHER INFORMATION: His6-tr-ssaG DNA construct

<400> SEQUENCE: 25
atgcggggtt ctcatcatca tcatcatcat ggtatggcta gcatgactgg tggacagcaa      60
atgggtcggg atctgtacga cgatgacgat aaggatcatc ccttcaccct ctcccacatg     120
gcgcaccagg caggccaggc cattaatgac aaaatgaatg gtaatgattt gctcaaccca     180
gaatcgatga ttaaagcgca atttgcctta cagcagtatt ctacatttat taattacgaa     240
agttcactga tcaaaatgat caaggatatg cttagtggaa tcattgctaa aatctga        297

<210> SEQ ID NO 26
<211> LENGTH: 4
<212> TYPE: PRT
<213> ORGANISM: Artificial
<220> FEATURE:
<223> OTHER INFORMATION: Type III Needle Protein Minor Epitope
<220> FEATURE:
<221> NAME/KEY: MISC_FEATURE
<222> LOCATION: (1)..(1)
<223> OTHER INFORMATION: Proline or Asparagine
<220> FEATURE:
<221> NAME/KEY: MISC_FEATURE
<222> LOCATION: (2)..(2)
<223> OTHER INFORMATION: Aspartic acid or Serine
<220> FEATURE:
<221> NAME/KEY: MISC_FEATURE
<222> LOCATION: (3)..(3)
<223> OTHER INFORMATION: Aspartic acid or Asparagine

<400> SEQUENCE: 26

Xaa Xaa Xaa Pro
1

<210> SEQ ID NO 27
<211> LENGTH: 82
<212> TYPE: PRT
<213> ORGANISM: Artificial
```

<220> FEATURE:
<223> OTHER INFORMATION: N-terminal del5 YscF fragment

<400> SEQUENCE: 27

Gly Phe Thr Lys Gly Thr Asp Ile Ala Asp Leu Asp Ala Val Ala Gln
1               5                   10                  15

Thr Leu Lys Lys Pro Ala Asp Ala Asn Lys Ala Val Asn Asp Ser
            20                  25                  30

Ile Ala Ala Leu Lys Asp Lys Pro Asp Asn Pro Ala Leu Leu Ala Asp
        35                  40                  45

Leu Gln His Ser Ile Asn Lys Trp Ser Val Ile Tyr Asn Ile Asn Ser
    50                  55                  60

Thr Ile Val Arg Ser Met Lys Asp Leu Met Gln Gly Ile Leu Gln Lys
65                  70                  75                  80

Phe Pro

<210> SEQ ID NO 28
<211> LENGTH: 77
<212> TYPE: PRT
<213> ORGANISM: Artificial
<220> FEATURE:
<223> OTHER INFORMATION: N-terminal del10 YscF fragment

<400> SEQUENCE: 28

Thr Asp Ile Ala Asp Leu Asp Ala Val Ala Gln Thr Leu Lys Lys Pro
1               5                   10                  15

Ala Asp Asp Ala Asn Lys Ala Val Asn Asp Ser Ile Ala Ala Leu Lys
            20                  25                  30

Asp Lys Pro Asp Asn Pro Ala Leu Leu Ala Asp Leu Gln His Ser Ile
        35                  40                  45

Asn Lys Trp Ser Val Ile Tyr Asn Ile Asn Ser Thr Ile Val Arg Ser
    50                  55                  60

Met Lys Asp Leu Met Gln Gly Ile Leu Gln Lys Phe Pro
65                  70                  75

<210> SEQ ID NO 29
<211> LENGTH: 72
<212> TYPE: PRT
<213> ORGANISM: Artificial
<220> FEATURE:
<223> OTHER INFORMATION: N-terminal del15 YscF fragment

<400> SEQUENCE: 29

Leu Asp Ala Val Ala Gln Thr Leu Lys Lys Pro Ala Asp Asp Ala Asn
1               5                   10                  15

Lys Ala Val Asn Asp Ser Ile Ala Ala Leu Lys Asp Lys Pro Asp Asn
            20                  25                  30

Pro Ala Leu Leu Ala Asp Leu Gln His Ser Ile Asn Lys Trp Ser Val
        35                  40                  45

Ile Tyr Asn Ile Asn Ser Thr Ile Val Arg Ser Met Lys Asp Leu Met
    50                  55                  60

Gln Gly Ile Leu Gln Lys Phe Pro
65                  70

<210> SEQ ID NO 30
<211> LENGTH: 67
<212> TYPE: PRT
<213> ORGANISM: Artificial
<220> FEATURE:
<223> OTHER INFORMATION: N-terminal del20 YscF fragment

```
<400> SEQUENCE: 30

Gln Thr Leu Lys Lys Pro Ala Asp Asp Ala Asn Lys Ala Val Asn Asp
1               5                   10                  15

Ser Ile Ala Ala Leu Lys Asp Lys Pro Asp Asn Pro Ala Leu Leu Ala
            20                  25                  30

Asp Leu Gln His Ser Ile Asn Lys Trp Ser Val Ile Tyr Asn Ile Asn
            35                  40                  45

Ser Thr Ile Val Arg Ser Met Lys Asp Leu Met Gln Gly Ile Leu Gln
        50                  55                  60

Lys Phe Pro
65
```